(12) United States Patent
Marzano et al.

(10) Patent No.: US 12,218,458 B2
(45) Date of Patent: *Feb. 4, 2025

(54) HIGH-VOLTAGE ELECTRICAL INSULATION FOR USE IN ACTIVE IMPLANTABLE MEDICAL DEVICES CIRCUIT BOARD CONNECTORS

(71) Applicant: Greatbatch Ltd., Clarence, NY (US)

(72) Inventors: Thomas Marzano, East Amherst, NY (US); Keith W. Seitz, Clarence Center, NY (US); Christine A. Frysz, Orchard Park, NY (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/376,687

(22) Filed: Oct. 4, 2023

(65) Prior Publication Data
US 2024/0039206 A1 Feb. 1, 2024

Related U.S. Application Data

(63) Continuation-in-part of application No. 17/561,048, filed on Dec. 23, 2021, which is a continuation of
(Continued)

(51) Int. Cl.
*H01R 13/52* (2006.01)
*A61N 1/375* (2006.01)
(Continued)

(52) U.S. Cl.
CPC ....... *H01R 13/5224* (2013.01); *A61N 1/3754* (2013.01); *H01G 4/35* (2013.01);
(Continued)

(58) Field of Classification Search
None
See application file for complete search history.

(56) References Cited

U.S. PATENT DOCUMENTS 2,685,073 A 7/1954 Damon
3,200,355 A 8/1965 Dahlen
(Continued)

OTHER PUBLICATIONS

European Search Report, 12170625.3, dated Oct. 4, 2012.
(Continued)

*Primary Examiner* — James Harvey
(74) *Attorney, Agent, or Firm* — Michael F. Scalise

(57) ABSTRACT

A circuit board for an active implantable medical device (AIMD) has a circuit board land connected to at least one electrical circuit. A hermetic feedthrough terminal pin connector for the AIMD includes an electrical insulator hermetically sealed to an opening of an electrically conductive ferrule. A terminal pin of the feedthrough extends outwardly beyond the insulator. A terminal pin connector has an electrically conductive connector housing that is connected to the circuit board land by an electrical connection material. At least one electrically conductive prong supported by the connector housing contacts and compresses against the feedthrough terminal pin to thereby make a removable electrical connection between the circuit board and the terminal pin. An insulative material loaded with electrically insulative nanoparticles coats at least a portion of the sidewall of the connector housing and the electrical connection material connecting the connector housing to the circuit board land.

28 Claims, 59 Drawing Sheets

Related U.S. Application Data application No. 16/809,676, filed on Mar. 5, 2020, now Pat. No. 11,211,741.

(60) Provisional application No. 63/414,102, filed on Oct. 7, 2022.

(51) Int. Cl.
    *H01G 4/35*      (2006.01)
    *H01R 13/426*    (2006.01)
    *H01R 13/719*    (2011.01)

(52) U.S. Cl.
    CPC ......... *H01R 13/426* (2013.01); *H01R 13/521* (2013.01); *H01R 13/719* (2013.01); *Y10T 29/49204* (2015.01)

(56) References Cited

U.S. PATENT DOCUMENTS

| | | |
|---|---|---|
| 3,621,445 A | 11/1971 | Horecky et al. |
| 4,187,605 A | 2/1980 | Selvin et al. |
| 4,421,378 A | 12/1983 | Sanford et al. |
| 4,424,551 A | 1/1984 | Stevenson et al. |
| 4,666,222 A | 5/1987 | Gallusser et al. |
| 4,767,342 A | 8/1988 | Sato |
| 4,824,380 A | 4/1989 | Matthews |
| 5,055,055 A | 10/1991 | Bakker |
| 5,103,818 A | 4/1992 | Maston et al. |
| 5,168,876 A * | 12/1992 | Quedens ............ A61B 5/288 600/376 |
| 5,333,095 A | 7/1994 | Stevenson et al. |
| 5,376,012 A | 12/1994 | Clark |
| 5,591,039 A | 1/1997 | Matthews |
| 5,893,779 A | 4/1999 | Bianca et al. |
| 6,059,600 A | 5/2000 | Vanbesien |
| 6,183,301 B1 | 2/2001 | Paagman |
| 6,224,404 B1 | 5/2001 | Sauer |
| 6,443,749 B2 | 9/2002 | Brownell et al. |
| 6,632,107 B1 | 10/2003 | Vanbesien |
| 6,643,903 B2 | 11/2003 | Stevenson et al. |
| 6,765,779 B2 | 7/2004 | Stevenson et al. |
| 6,765,780 B2 | 7/2004 | Brendel et al. |
| 6,852,925 B2 | 2/2005 | Wolf et al. |
| 6,932,658 B2 | 8/2005 | Liang |
| 7,035,076 B1 | 4/2006 | Stevenson |
| 7,038,900 B2 | 5/2006 | Stevenson et al. |
| 7,068,081 B2 | 6/2006 | Naffziger et al. |
| 7,167,749 B2 | 1/2007 | Biggs et al. |
| 7,172,467 B1 | 2/2007 | Yohn et al. |
| 7,195,523 B2 | 3/2007 | Naviaux |
| 7,249,981 B2 | 7/2007 | Chen |
| 7,295,123 B2 | 11/2007 | Engelberg et al. |
| 7,391,601 B1 | 6/2008 | Imani |
| 7,630,768 B1 | 12/2009 | Coffed et al. |
| 7,751,893 B2 | 7/2010 | Biggs et al. |
| 7,794,256 B1 | 9/2010 | Sochor |
| 7,812,691 B1 | 10/2010 | Fisk et al. |
| 7,822,477 B2 | 10/2010 | Rey et al. |
| 7,917,219 B2 | 3/2011 | Stevenson et al. |
| 7,931,507 B2 | 4/2011 | Yu et al. |
| 8,065,009 B2 | 11/2011 | Biggs |
| 8,096,838 B2 | 1/2012 | Dilmaghanian |
| 8,103,348 B1 | 1/2012 | Coffed et al. |
| 8,112,152 B2 | 2/2012 | Taylor et al. |
| 8,179,658 B2 | 5/2012 | Stevenson et al. |
| 8,195,295 B2 | 6/2012 | Stevenson et al. |
| 8,422,195 B2 | 4/2013 | Stevenson |
| 8,433,410 B2 | 4/2013 | Dabney et al. |
| 8,437,855 B2 | 5/2013 | Sjostedt et al. |
| 8,468,664 B2 | 6/2013 | Brendel et al. |
| 8,543,209 B2 | 9/2013 | Tyers et al. |
| 8,577,453 B1 | 11/2013 | Stevenson et al. |
| 8,642,887 B1 | 2/2014 | Li et al. |
| 8,653,384 B2 | 2/2014 | Tang et al. |
| 8,659,870 B2 | 2/2014 | Brendel et al. |
| 8,855,785 B1 | 10/2014 | Johnson et al. |
| 8,868,189 B2 | 10/2014 | Stevenson et al. |
| 8,900,008 B2 | 12/2014 | Day et al. |
| 8,938,309 B2 | 1/2015 | Marzano et al. |
| 9,014,808 B2 | 4/2015 | Dabney et al. |
| 9,064,640 B2 | 6/2015 | Brendel et al. |
| 9,065,224 B2 | 6/2015 | Marzano et al. |
| 9,108,066 B2 | 8/2015 | Woods et al. |
| 9,223,253 B2 | 12/2015 | Lior et al. |
| 9,352,150 B2 | 5/2016 | Stevenson et al. |
| 9,427,596 B2 | 8/2016 | Brendel et al. |
| 9,463,329 B2 | 10/2016 | Frysz et al. |
| 9,511,220 B2 | 12/2016 | Marzano et al. |
| 9,692,173 B2 | 6/2017 | Marzano et al. |
| 9,757,558 B2 | 9/2017 | Stevenson et al. |
| 9,764,129 B2 | 9/2017 | Stevenson et al. |
| 9,806,443 B1 | 10/2017 | Thackston |
| RE46,699 E | 2/2018 | Woods et al. |
| 9,889,306 B2 | 2/2018 | Stevenson et al. |
| 9,895,534 B2 | 2/2018 | Stevenson et al. |
| 9,931,514 B2 | 4/2018 | Frysz et al. |
| 9,937,354 B2 | 4/2018 | Barry et al. |
| RE46,837 E | 5/2018 | Tyers et al. |
| 9,993,650 B2 | 6/2018 | Seitz et al. |
| 10,080,889 B2 | 9/2018 | Marzano et al. |
| 10,092,749 B2 | 10/2018 | Stevenson et al. |
| 10,099,051 B2 | 10/2018 | Stevenson et al. |
| 10,124,164 B2 | 11/2018 | Stevenson et al. |
| 10,249,415 B2 | 4/2019 | Seitz et al. |
| 10,272,252 B2 | 4/2019 | Seitz et al. |
| 10,272,253 B2 | 4/2019 | Seitz et al. |
| 10,350,421 B2 | 7/2019 | Stevenson et al. |
| 10,376,688 B2 | 8/2019 | Chen et al. |
| 2001/0033478 A1 * | 10/2001 | Ortiz ................ H01R 13/6599 361/818 |
| 2003/0139096 A1 | 7/2003 | Stevenson et al. |
| 2006/0089682 A1 * | 4/2006 | Kronich ............ A61N 1/3754 607/32 |
| 2006/0167522 A1 | 7/2006 | Malinowski |
| 2006/0221543 A1 | 10/2006 | Stevenson et al. |
| 2007/0134985 A1 | 6/2007 | Frysz et al. |
| 2007/0203530 A1 | 8/2007 | Hubing et al. |
| 2007/0260282 A1 | 11/2007 | Taylor et al. |
| 2009/0068863 A1 | 3/2009 | Walter |
| 2009/0259265 A1 | 10/2009 | Stevenson et al. |
| 2010/0192355 A1 | 8/2010 | Zhao et al. |
| 2011/0106189 A1 | 5/2011 | Seeley et al. |
| 2011/0303458 A1 | 12/2011 | Sutay et al. |
| 2012/0309237 A1 | 12/2012 | Marzano et al. |
| 2013/0274820 A1 | 10/2013 | Malinowski et al. |
| 2014/0272457 A1 | 9/2014 | Watada |
| 2015/0245468 A1 | 8/2015 | Barry et al. |
| 2015/0295349 A1 | 10/2015 | Marzano et al. |
| 2017/0266451 A1 | 9/2017 | Lim et al. |
| 2019/0356097 A1 | 11/2019 | Landwehr et al. |
| 2022/0115806 A1 | 4/2022 | Marzano et al. |

OTHER PUBLICATIONS

Stevenson, Bob, "Dissipation Factor Testing is Inadequate for Medical Implant EMI Filters and Other High Frequency MLC Capacitor Applications", 23rd Capacitor and Resistor Technology Symposium, CARTS 2003, Mar. 31-Apr. 3, 2003, Chaparral Suites Resort, Scottsdale, Arizona.

Extended European Search Report, Application No. 23202461.2, dated Sep. 2, 2024.

* cited by examiner

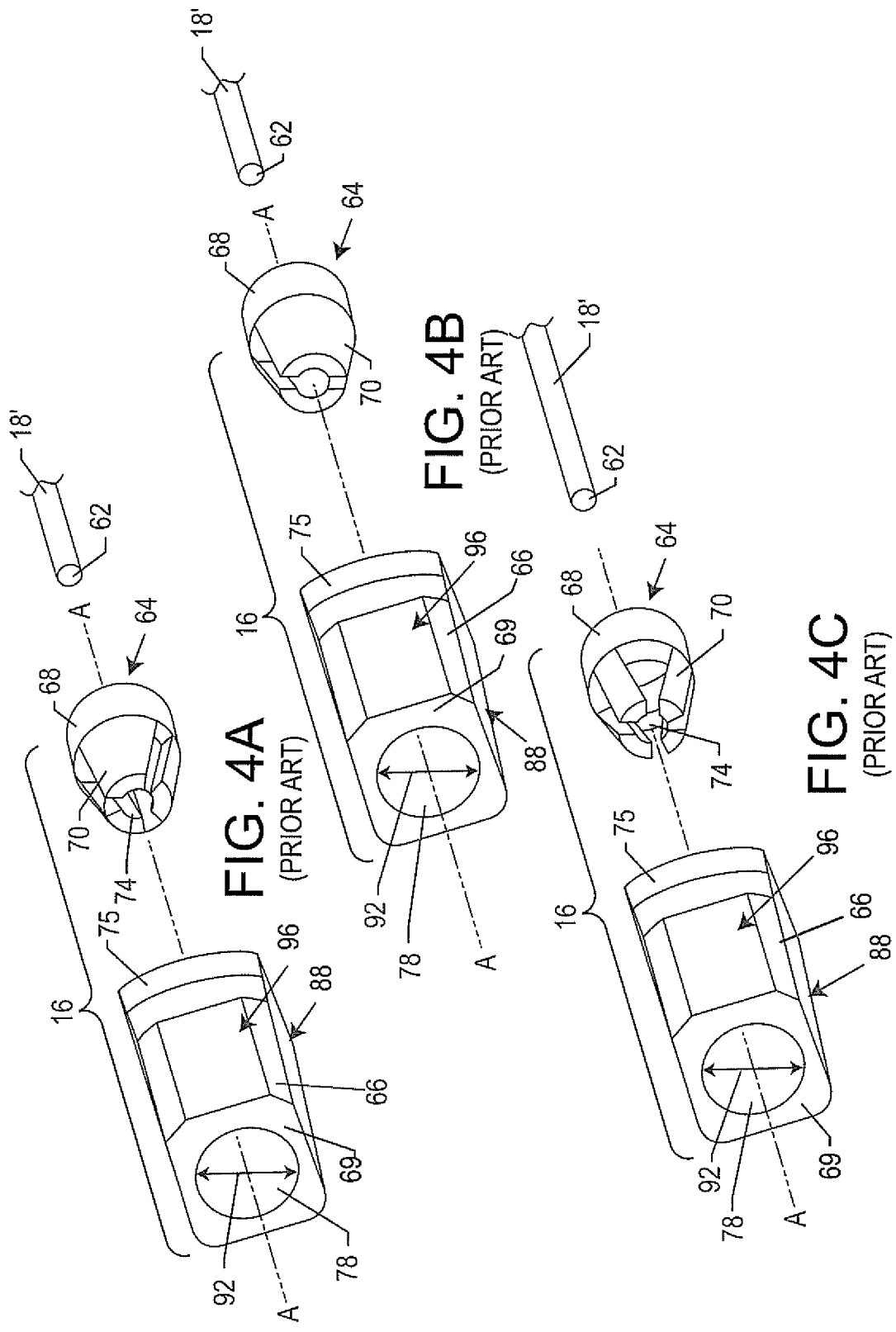

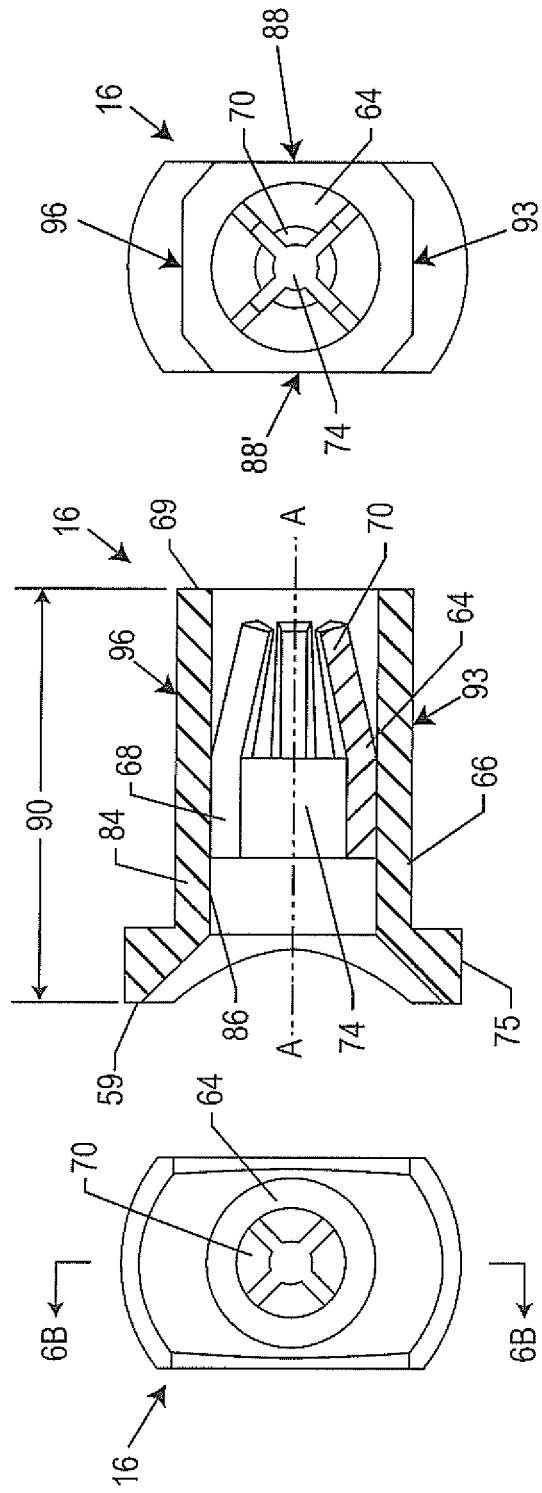

(TOP VIEW OF DEVICE SIDE)

| Element No. | Description | Symbol |
|---|---|---|
| 360 | No polymer insulating material in this location | |
| 353 | Uncured (flowable) insulating nanoparticle filled polymer insulating material | ▼ |
| 359 | Location for placing uncured (flowable) insulating nanoparticle filled polymer insulating material | |
| 379 | Cured (solid) insulating nanoparticle filled polymer insulating material | ▼ |
| 354 | Uncured (flowable) polymer insulating material without insulating nanoparticle fill | |
| 358 | Location for placing uncured (flowable) polymer insulating material without insulating nanoparticle fill | |
| 378 | Cured (solid) polymer insulating material without insulating nanoparticle fill | ▼ |

FIG. 34

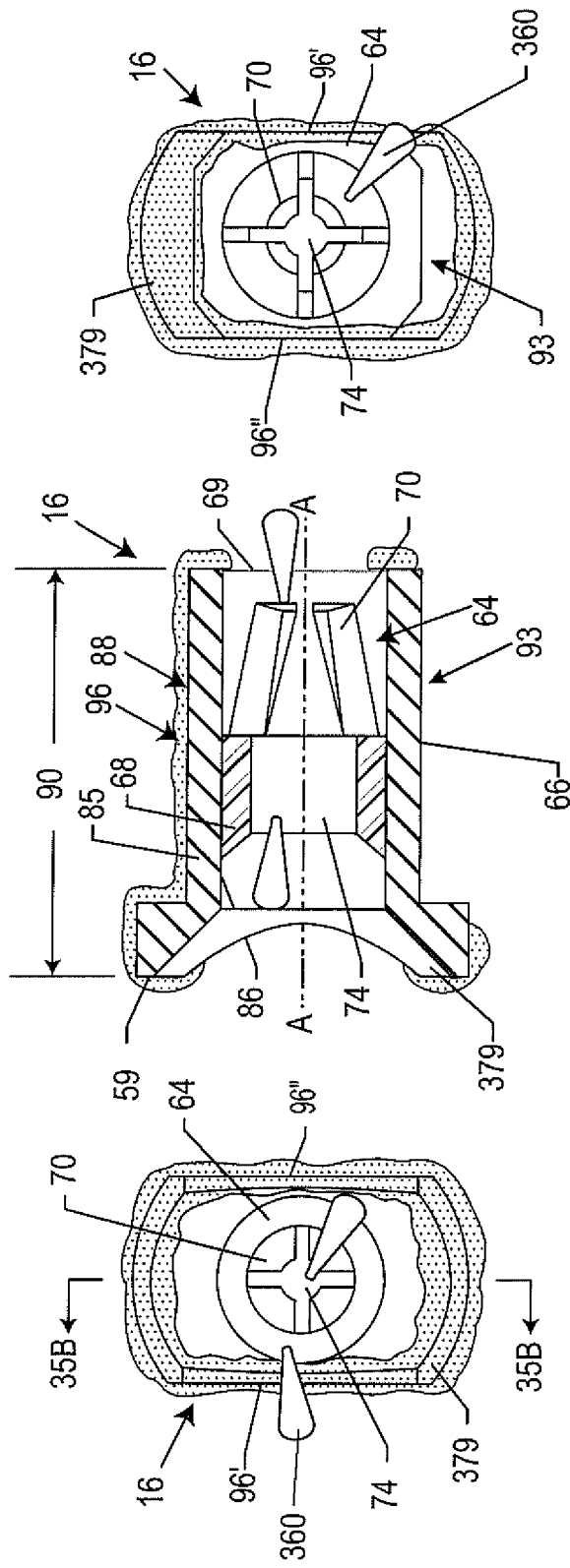
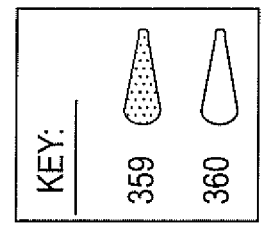
FIG. 35A   FIG. 35B   FIG. 35C

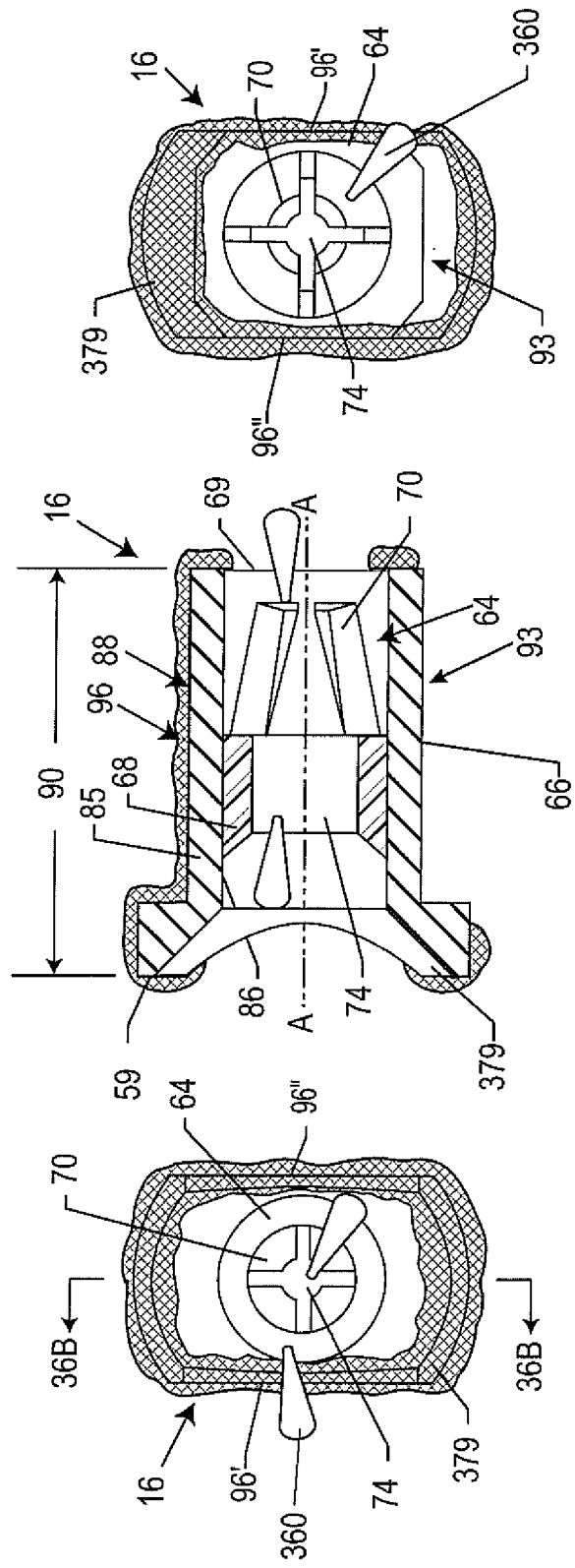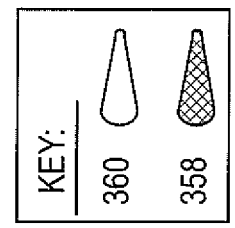
FIG. 36C
FIG. 36B
FIG. 36A

US 12,218,458 B2

HIGH-VOLTAGE ELECTRICAL INSULATION FOR USE IN ACTIVE IMPLANTABLE MEDICAL DEVICES CIRCUIT BOARD CONNECTORS

CROSS-REFERENCE TO RELATED APPLICATIONS

This application is a continuation-in-part application claiming priority to U.S. patent application Ser. No. 17/561, 048, filed on Dec. 23, 2021, now U.S. Pat. No. 12,149,021, which claims priority to U.S. patent application Ser. No. 16/809,676, filed on Mar. 5, 2020, now U.S. Pat. No. 11,211,741; and claims priority to U.S. provisional application Ser. No. 63/414,102, filed on Oct. 7, 2022; the contents of which are fully incorporated herein by these references.

FIELD OF THE INVENTION

The present invention generally relates to high voltage insulation for active implantable medical device (AIMD) circuit board connectors, including various types of insulation and the novel addition of nano-scale metal oxide insulating powders to the insulating materials. In general, the present invention teaches increasing the high-voltage dielectric breakdown strength of the AIMD circuit board connectors and their related subassemblies.

BACKGROUND OF THE INVENTION

Feedthrough assemblies are generally well known by those skilled in the art of active implantable medical devices (AIMDs). AIMDs use feedthroughs in connecting electrical signals through the AIMD casing (also known as a housing, a can or a case) of a device or an electronic instrument. For example, in an implantable medical device, such as a cardiac pacemaker, defibrillator, or neurostimulator, the feedthrough assembly comprises one or more conductive terminal pins supported by an insulator structure for passage of electrical signals from the exterior to the interior of the medical device. The conductive terminals are fixed into place using a metallization and a gold braze process, which provide a hermetic seal between the terminal pin(s) and insulator material of the feedthrough. Similarly, the insulator structure is fixed into place to a ferrule or an opening of the AIMD case using the metallization and gold braze processes.

Conventionally, the terminal pin distal ends are electrically connected directly within the AIMD to circuit boards inside the casing or to an AIMD header block outside the casing. Electrical connection can be permanently made in accordance with the prior art. As an example, the terminal pin distal end may be electrically connected directly to an electrical circuit board residing within the device by using a soldering or welding attachment process. This connection is readily achievable utilizing platinum or platinum alloy based terminal pins of the prior art.

Alternatively, the terminal pin distal end may instead have a removable electrical connection by using a circuit board connector as taught by U.S. Pat. No. 11,211,741, assigned to the present Applicant. Regardless of the electrical connection made, however, there is a need for increasing the high-voltage dielectric breakdown strength of AIMD circuit board connectors and other related subassemblies that may be exposed to high-voltage stress.

AIMD active electronic circuit boards are extremely complex because they contain not only digital circuits, but also biological sensing circuits (analogue circuits). Modern AIMDs may have over 4,500 programmable functions and extensive memory storage capability, where doctors can retrieve waveforms after a cardiac event. When an AIMD active electronic circuit board is built, it is placed on a large test console where computers thoroughly check every function of the circuit board. The active electronic circuit board of an AIMD is considered defective when any single bit error or logic error is identified. Once an AIMD active electronic circuit board and the battery are installed and the AIMD is hermetically sealed, the AIMD then undergoes final testing. If the AIMD active electronic circuit board is found to be defective at final testing, it is too late to replace the defective circuit board. It is noted that circuit boards come in a multitude of sizes, shapes, and materials.

FIG. 1 is a wire form diagram of a generic human body showing a number of implanted medical devices. Illustrated are the various types of active implantable and external medical devices 12 that are currently in use. Device 12A is a family of external and implantable hearing devices, which include the group of hearing aids, cochlear implants, piezoelectric sound bridge transducers and the like. Device 12B includes the complete family of neurostimulators and brain stimulators. For example, neurostimulators are used to stimulate the Vagus nerve to treat epilepsy, obesity, and depression. Brain stimulators are similar to a pacemaker-like device and include electrodes implanted deep into the brain for sensing the onset of a seizure and also providing electrical stimulation to brain tissue to prevent the seizure from actually happening. The leads that come from a deep brain stimulator are often placed using real time imaging. Frequently, such leads are placed real time during MRI. Device 12C shows a cardiac pacemaker, which is well-known in the art and may have either endocardial or epicardial leads. Implantable pacemakers may also be leadless (meaning without a lead or leads). The family of cardiac pacemakers 12C includes the cardiac resynchronization therapy devices (CRT-P pacemakers) and leadless pacemakers. CRT-P pacemakers are unique in that, they pace both the right and left sides of the heart. The cardiac device family also includes any and all types of biologic monitoring and/or data recording devices and all types of implantable loop recorders (ILR) or other such monitors and records biologic activity, for example, an ILR that records the electrical activity of the heart. Device 12D includes the family of left ventricular assist devices (LVAD's) and artificial hearts. Device 12E includes an entire family of drug pumps, which can be used for dispensing of insulin, chemotherapy drugs, pain medications and the like. Insulin pumps are evolving from passive devices to active devices that have sensors and closed loop systems, which can, for example, monitor blood glucose levels in real time. Such active pump devices tend to be more sensitive to EMI than passive pumps, which have no sense circuitry or externally implanted leads. Device 12F includes a variety of external or implantable bone growth stimulators for rapid healing of fractures. Device 12G includes urinary incontinence devices. Device 12H includes the family of pain relief spinal cord stimulators and anti-tremor stimulators. Device 12H also includes the complete family of neurostimulators used to block pain signals. Device 12I includes the complete families of implantable cardioverter defibrillators (ICD) and congestive heart failure (CHF) devices, including cardio resynchronization therapy devices (CRT-D). A CRT-D, which is a special subcutaneous device for heart failure patients who are also at high risk for sudden cardiac death, can also provide high-voltage defibrillation. The device 12I may have either endocardial or epicardial leads. Device 12J illustrates an externally worn pack, such as, but not limited to, an external insulin pump, an external drug pump, an external neurostimulator, a Holter monitor with skin electrodes or a ventricular assist device power pack.

FIG. 1A illustrates a perspective view of a first casing half 112 with various components internal to an AIMD prior to hermetically sealing a second casing half thereby forming AMID casing 32 of an AIMD 12. Shown is a battery 130, which can be either a primary or a secondary battery. For example, in the case that the AIMD 12 is a cardiac pacemaker, the battery 130 could be a primary battery, while, in the case that the AIMD 12 is a neurostimulator, the battery 130 could be a secondary battery or rechargeable battery. The main AIMD active electronic circuit board 106 is also shown along with at least one microprocessor 131 and various other circuit board components 133. The AIMD active electronic circuit board 106 has a plurality of terminal pin connector housings 66 that have also been mechanically and electrically attached to the AIMD active electronic circuit board 106 and, importantly, to its circuit board inputs and outputs. Circuit boards contain the circuits that provide, for example, pacing pulses to simulate the natural biological signals of the heart, sending pacing pulses from the pacemaker circuit to a terminal pin, and then from the terminal pin to the distal electrodes of an implanted lead in order to treat cardiac arrhythmias (problems with a rate or rhythm of a heartbeat). Circuit boards can also comprise circuits that can sense biological signals received by sense amplifiers within a circuit of a microprocessor 131. Circuit boards may also comprise circuits for telemetry to which one or more RF telemetry pins are connected. In general, RF telemetry antennas would be included in an AIMD header block area (not shown), and the RF telemetry signal would pass from the RF telemetry antenna to the one or more RF telemetry pins, and then from the RF telemetry pin to the microprocessor of the circuit board. Accordingly, an AIMD is thereby enabled to sense, process and adjust a pacing therapy in accordance with specific patient needs and/or to communicate data.

Referring once again to FIG. 1A, one can see that the AIMD active electronic circuit board 106 has been "plugged in" and connected to the hermetic seal terminal pins 18 of the AIMD hermetically seal feedthrough 14. The circuit board is also shown connected to the battery 130. As has been previously disclosed, there may be an internally grounded feedthrough capacitor 24' attached to the AIMD hermetically seal feedthrough 14 (not shown), or instead of a feedthrough capacitor, an EMI filter circuit board 106' (not shown) comprising one of an MLCC, an X2Y attenuator, a flat-thru capacitor or combinations thereof can be used.

FIG. 1B illustrates an AIMD feedthrough connector assembly 10 comprising an AIMD hermetically sealed feedthrough 14 and terminal pin connectors 16, 16gnd. The AIMD hermetically sealed feedthrough 14 of the AIMD feedthrough connector assembly 10 includes active terminal pins 18, 18' that provide for conducting electrical signals to and from body tissue, such as a patient's heart, while hermetically sealing the interior (device side) of the AIMD 12 (not shown) against ingress of patient body fluids that could otherwise disrupt AIMD operation or cause AIMD malfunction. The feedthrough of the AIMD feedthrough connector assembly 10 of FIG. 1 also comprises two ground terminal pins 18'gnd mechanically and electrically connected to the feedthrough ferrule 26.

FIG. 2 is very similar to FIG. 1B, except that the AIMD feedthrough connector assembly 10 now includes an internally grounded feedthrough capacitor 24', as illustrated. Internally grounded feedthroughs are taught by U.S. Pat. No. 5,905,627, the contents of which are fully incorporated herein by this reference. As illustrated, the internally grounded feedthrough capacitor 24' is disposed on the device side of the AIMD feedthrough connector assembly 10. In accordance with the present invention, the embodiment of FIG. 2 contains within the common housing body 94 any configuration of terminal pin connectors 16 (not shown). The common housing body 94 may comprise a metallic structure, a ceramic structure, or a structure comprising a ceramic and a metal. The common housing body 94 may further be an insulated housing body comprising a ceramic structure, or a ceramic structure with metal structures optionally positioned in, on or about the ceramic structure. Referring back to FIG. 2, there is a breakout section comprising a double cross-hatching, which indicates that the common housing body 94 is made of a polymeric insulating material without an insulating nanoparticle fill 378. The insulating material 378 of the common housing body 94 may be any of the conventionally applied insulating materials, including an epoxy, a liquid silicone rubber, a polycarbonate, a polyester, a polyether, a polyurethane, a polyimide, or a polyamide. In an alternative embodiment, the insulating material may be a nanoparticle-filled polymeric insulating material 379.

In the case where the common housing body 94 is metallic, it is contemplated that an insulating material would be contained inside the common housing body 94, the insulating material positioned to thereby electrically insulate each of the terminal pins 18 one from the other. The individual terminal pin connectors 16 are not shown as they are embedded in the common housing body 94. It is contemplated that the common housing body 94 may comprise terminal pin connectors 16 having similar or the same shape and configuration as the terminal pin connectors 16 previously described in FIG. 1B or may comprise any of the connector structures disclosed herein. The common housing body 94 may further comprise any combination of connector structures disclosed, including terminal pin connector 16. As used herein, the term "common housing body" is defined as one connector housing 94 in which two or more connector structures or terminal pin connectors 16 reside.

Referring once again to FIG. 2, as illustrated, the internally grounded feedthrough capacitor 24' is shown vertically aligned with the structure of the ferrule 26. However, the internally grounded feedthrough capacitor 24', including how the internally grounded feedthrough capacitor is attached to the ferrule 26 of hermetically sealed feedthrough 14, is only an example. There are various other ways that feedthrough capacitors may be attached to hermetically sealed feedthroughs. For example, externally grounded feedthrough capacitors attached to AIMD hermetically sealed feedthroughs are well known in the prior art, including U.S. Pat. No. 5,333,095, (otherwise known as the Surface Mount patent); and U.S. Pat. Nos. 5,978,204; 5,905,627 (Internal Ground patents, which would require the addition of at least one internally grounded terminal pin 18'gnd that would be connected to the ferrule 26), the contents of which are fully incorporated herein by these references. Following are additional patents that disclose attachment options for externally grounded feedthrough capacitors to hermetically sealed feedthroughs: U.S. Pat. Nos. 6,643,903; 6,765,779; 7,035,076; 7,917,219; 8,179,658; 8,422,195; 8,433, 410; 8,468,664; 8,543,209; 8,577,453; 8,659,870; 8,653,384; 8,855,785; 8,868,189; 9,014,808; 9,064,640; 9,108,066; 9,352,150; 9,427,596; 9,463,329; 9,757,558; 9,764,129; re-issue 46,699; re-issue 46,837;

9,895,534; 9,889,306; 9,931,514; 9,993,650; 10,080,889; 10,092,749; 10,099,051; 10,124,164; 10,249,415; 10,272,252: 10,272,253 and 10,350,421, the contents of which are also fully incorporated herein by these references.

FIG. 3A is a prior art cross-sectional view illustrating an alternative embodiment to FIG. 1B where an externally grounded feedthrough capacitor 24 has been added to the hermetically sealed feedthrough 14 of a feedthrough capacitor connector assembly 20. Externally grounded feedthrough capacitors 24 are known in the industry as conventionally grounded feedthrough capacitors. The feedthrough capacitor connector assembly 20 further comprises at least one terminal pin connector 16. For identification purposes, the terminal pin distal end 62 is defined as the portion of the terminal pin 18' that inserted through the terminal pin connector 16. Externally grounded feedthrough capacitors or internally grounded feedthrough capacitors could alternatively be used, as disclosed in U.S. Pat. No. 5,905,627 incorporated herein fully by this reference. The feedthrough capacitor connector assembly 20 of FIG. 3A may also optionally incorporate the teachings of a number of other patents, including U.S. Pat. Nos. 4,424,551; 5,333,095; 6,643,903; 6,765,779, and 7,675,780 the contents all of which are fully incorporated herein by these references.

As further shown in FIG. 3A, the filtered feedthrough assembly 22 includes the externally grounded feedthrough capacitor 24 that provides filtering of undesirable EMI signals before they can enter the AIMD casing 32 via the terminal pins 18. The capacitor dielectric 48 may be a monolithic ceramic, such as a multi-layer ceramic capacitor (MLCC), or may alternatively be stacked film, tantalum, or electrolytic capacitors. It is understood that the capacitor dielectric 48 may support a plurality of spaced-apart layers of active electrode plates 50 or first electrode plates in spaced relationship with a plurality of spaced apart layers of ground electrode plates 52 or second electrode plates. Additionally, the capacitor dielectric 48 may be shaped to match the shape of the ferrule 26, or may alternatively have an oval, round, square or rectangular shape that either differs from, approaches, or is essentially similar to the shape of the ferrule 26.

Referring once again to the filtered feedthrough assembly 22 of FIG. 3A, the externally grounded feedthrough capacitor 24 in this embodiment is disposed on the body fluid side. This is a different location compared to the internally grounded feedthrough capacitor 24' of FIG. 2, which is disposed on the device side. The advantage of having the feedthrough capacitor on the device side is that it is inside the hermetically sealed AIMD casing 32 (also known in the prior art as a "housing") and is therefore, not exposed to body fluid. One is referred to U.S. Pat. No. 6,985,347, which describes an EMI filter capacitor assembly that utilizes biocompatible and non-migratable materials to adapt electronic components for direct body fluid exposure, the contents of which are fully incorporated herein by this reference.

Referring again to FIG. 3A, an exemplary electrical schematic is shown. Represented are two terminal pins 18, which is also known as a bipolar AIMD capacitor. It is appreciated that there can be any number of AIMD terminal pins including five active terminal pins as shown in FIG. 1B (and two ground pins). Feedthrough capacitors C1 and C2 act as filters or high frequency diverters, which prevent electromagnetic interference (EMI) originating from the body fluid side (the EMI can undesirably couple to implanted leads or AIMD header block wiring) thereby, protecting such dangerous electromagnetic interference from entering into the device side of the AIMD 12 where the EMI could interfere with a sensitive AIMD active electronic circuit board 106. Feedthrough capacitors are known in the industry as three-terminal devices and because they have extremely low inductance, they provide very broadband filtering up to frequencies of 3 GHz-10 GHz (and even above 10 GHz). Other three-terminal capacitors will be described later in the present application, including flat-thru capacitors and some X2Y attenuator designs. Two-terminal capacitors will also be described, including MLCCs and some X2Y attenuator designs. It is noted that two-terminal capacitors typically do not offer filtering at extremely high frequencies, however, when carefully designed, two-terminal capacitors can be effectively used in AIMDs. It is understood by one skilled in the art that electromagnetic interference could confuse the AIMD and create various life-threatening situations. This is extremely dangerous for cardiac pacemaker dependent patients who rely on pacemakers to keep their hearts beating. If the cardiac pacemaker becomes confused, it could stop stimulating the heart and the patient would die.

FIG. 3B is prior art similar to FIG. 3A with a feedthrough capacitor disposed on the body fluid side of the hermetic terminal subassembly 20. In this case, the terminal pin connectors are different. The one on the left side has a closed end near the lead 18' tip 62, as illustrated. On the right side, lead 18' includes a notch 71, which facilitates a firm grip from prong 70. In this case, the housing is open at the distal end 78, as shown.

FIG. 3C is prior art similar to FIG. 3A, except the feedthrough capacitor 24 is now disposed on the device side, which means it is inside of hermetically sealed casing 32 and no longer needs to be constructed such that it has to be biocompatible. Most feedthrough capacitors in the prior art are disposed on the device side to protect them from harmful body fluids.

FIGS. 4, 4A-4C and 5A-5E illustrate prior art embodiments of the terminal pin connector 16. In these embodiments, the shape of the connector housing 66 of the terminal pin connector 16 may comprise a square or rectangular shape. The exterior of the terminal pin connector 16 has four flat (in other words, planar) surfaces: a top housing planar surface 96, a bottom housing planar surface 93 (not visible), a right sidewall planar surface 88 and a left sidewall planar surface (not visible). At least two planar surfaces are shown in FIG. 4: an exterior sidewall comprising a planar surface 88 and a planar surface 93 in the connector housing 66 (NOTE: the connector housing 66 can alternatively have a completely round shape as shown in FIG. 7C; an oval or hexagonal shape, not shown; a round shape having at least a portion of the perimeter surface being a planar surface 93 as shown in FIGS. 37C and 37D, the planar surface 93 being applicable to an oval shape as well). The terminal pin connector 16 includes an alignment feature 75, the alignment feature of the embodiment of FIG. 4 comprising an inwardly tapering surface, which helps to guide an off-center terminal pin 18 to the center bore diameter 92. As used herein, the term "alignment feature" is defined as an outwardly projecting and/or outwardly protruding flange, edge, rim, collar, or rib on a structure serving to locate, register, guide and/or align a first object for attaching, connecting, or mating to a second object. The alignment feature may either be a continuous, a discontinuous, or a partial projection or protrusion around the circumference or the perimeter of a connector housing 66. The connector housing 66 of FIG. 4 is particularly designed having a square or rectangular shape to intentionally narrow down and/or restrict the width of the terminal pin connectors 16 so that they can be aligned closely together on an AIMD active electronic circuit board 106 (not shown) with very close spacing (otherwise known as close pitched). This is very important particularly for high conductor pathway count in a small component or miniature feedthrough assemblies, which necessitate close pitch conductor pathway spacing requirements. One example of an AIMD 12 having high count or close pitch conductive pathways is a spinal cord neurostimulators, which generally comprise more than 24 terminal pins 18. As defined herein, a square or a rectangular connector housing 66 comprises at least two flat or planar surfaces (similar to or such as the exemplary exterior planar surfaces 88 and 93 of FIG. 4) for close placement when multiple terminal pin connectors 16 are required in a limited space (known as close pitch), and wherein each terminal pin connector 16 is capable of attachment to at least one circuit board electrical connection pad 104, also known as a circuit board land 104, either being directly physically and electrically connected, or electrically connected by an electrical connection material 107.

Referring again to FIG. 5E, it is contemplated that the spring clip 64' is electrically and mechanically connected to the inside diameter of the connector housing 66 of the terminal pin connector 16. The connector housing 66 could be angled inward (chamfered) so that the spring clip 64' compresses while it is being inserted or a tool could be used, similar to a piston ring compressor for the pistons of an automobile. One could also use a shape-memory alloy for any of the configurations just described, such as Nitinol, wherein the insertion could be done at one temperature and then the material would expand when it reaches body temperature. If Nitinol is used, the Nitinol can further be modified as described earlier to impart different spring constants at different points of the spring clip 64'.

Referring to prior art FIGS. 6A to 6C (also see FIGS. 4, 4A-C), the connector housing 66 may comprise a housing sidewall 76 which encompasses a connector housing through-bore 78 along the A-A axis that extends longitudinally therethrough, or at least partially therethrough when the connector housing 66 comprises a blind hole. In the embodiments shown, the connector housing 66 is designed similarly to that of a tube having an opening that extends from a proximal housing end 80 to a distal housing end 82. The connector housing 66 comprises a housing sidewall thickness 84 that extends from a housing interior sidewall surface 86 to a housing exterior sidewall surface 88. In certain embodiments, the terminal pin connector 16 may have a terminal pin connector length 90 ranging from about 0.025 inches to about 0.300 inches and a through-bore diameter 92 that ranges from about 0.01 inches to about 0.030 inches.

As illustrated in prior art FIG. 7A, the housing bottom planar surface 98 (hidden underneath) of the connector housing 66 is designed to establish intimate electrical contact with an electrical connection pad 104 of an AIMD active electronic circuit board 106 of the active implantable medical device 12. As such, the connector housing 66 may be composed of an electrically conductive material or alternatively may be coated with an electrically conductive material, such as an electrically conductive foil, metallization, plating or vapor deposited film as previously disclosed for clip 64. The coating may additionally be used to facilitate joining processes, such as soldering or even welding. The coating may also comprise any one or more of the materials previously disclosed for clip 64.

Alternatively, a portion of the housing exterior surface 96' and a portion of the housing interior sidewall surface 86 of the connector housing 66 may be constructed of an electrically conductive material conducive to the joining processes of soldering and/or welding. The connector housing 66 is designed such that an electrical connection is made between the terminal pin 18 of the AIMD hermetically sealed feedthrough 14 and the AIMD active electronic circuit board 106 of the active implantable medical device 12.

Once again referring to FIG. 7A, the unfiltered or filtered AIMD connector feedthrough assembly 10 or the feedthrough connector capacitor assembly 20 is positioned within the active implantable medical device 12. The housing exterior surface 96' of the connector housing 66 may be electrically joined to an electrical connection pad 104 of the AIMD active electronic circuit board 106 by a laser weld 108' imparted by a joining instrument 108. Alternatively, the housing exterior surface 96' may be electrically connected to an electrical connection pad 104 of the AIMD active electronic circuit board 106 by a solder, using a soldering joining instrument (not shown). In either case, the joining process may be utilized to join at least a portion of the housing exterior surface 96' to the circuit board electrical connection pad 104.

The electrical connection 107' may be a laser weld 108', a solder, a thermal-setting conductive adhesive or even a ball grid array type approach where, before the connector housings 66 of the terminal pin connectors 16 are attached to the circuit board electrical connection pads 104, either a BGA (ball grid array) conductive epoxy or solder bump would be applied and then a robot would place the housing exterior surface 96' of the connector housing 66 of all the terminal pin connectors 16 in place, which, through a bulk reflow operation, the solder would be reflowed or the conductive epoxy would be cured. If a laser weld 108' is made, it is contemplated that the circuit board electrical connection pad 104 (or alternatively, a circuit board land or a circuit trace) would comprise a metallic pad, such as a Kovar pad, whereby, the laser weld 108' would include the melting and joining of the adjacent materials to form a solid mechanical metallurgical bond and a very low resistance and low impedance electrical connection 107'. Referring once again to FIG. 7A, one will note that there is a gold braze 46b that connects and mechanically and hermetically seals the active terminal pins 18 to the insulator 28. The right-hand side terminal pin 18 has a gold braze 46bgnd. In this case, the ground terminal pin 18gnd is shown gold brazed 46bgnd directly to the metallic ferrule 26. Alternatively, the ground terminal pin 18gnd could be a laser weld 108' that directly joins the ground terminal pin 18gnd to the metallic ferrule 26. In the case of a terminal pin laser weld 108' directly to the metallic ferrule 26, the ground terminal pin 18gnd would need to comprise an oxide-resistant material, or at least be coated with an oxide-resistant material once any oxides that form during laser welding are cleaned/removed from the ground terminal pin. The brazing or welding process grounds the terminal pin 18gnd. It is very common in pacemaker and ICD applications that the AIMD casing 32 (also known as a can or housing), which essentially comprises two can halves 112 and 114, can be used as one of the electrodes. For example, for an implantable cardioverter defibrillator, a defibrillation vector can be between the AIMD casing 32 and a distal shocking electrode (not shown), which is placed, for example, in the right ventricle area. To perform this function, the AIMD active electronic circuit board 106 is programmed to apply the ICD shock between a grounded pin, such as 18gnd, such that the pulse polarity is between the AIMD casing 32 and the single distal electrode. In various applications, the grounded pin may not extend into the body fluid side of the AIMD12 as shown, however, in certain neurostimulators or other specialized applications, the grounded pin will extend into the boy fluid side of the AIMD 12.

Referring to FIGS. 7A and 7B, the circuit board electrical connection pad 104 could comprise a large circuit board via hole 109 as shown in FIG. 7C, which could be designed to accept and receive a round connector housing 66 (not shown). The round connector housing 66 would be mechanically and electrically attached to the circuit board via hole 109 by one of a press fit, a solder, an electrically conductive adhesive or other common circuit board via hole connection material and/or process, including crimps, and the like. This embodiment could position the connector housing 66 residing in the circuit board via hole 109 perpendicular to the position illustrated in FIGS. 7A and 7B. As such, the terminal pins 18 and 18gnd could have a 90° bend or other bend angle in order to align with a housing interior sidewall surface 86 such that the bent terminal pins 18 and 18gnd could slide along the housing interior sidewall surface 86 thereby 'plugging into' the circuit board connector housing 66. Using common multilayer circuit board trace techniques, these circuit board via holes 109 that receive connector housings 66 could be staggered in various patterns thereby enabling electrical connection of high count and/or close pitched feedthrough conductors, including uniquely or other non-traditionally positioned feedthrough terminal pins 18, 18gnd, while preserving removability of circuit boards for rework or replacement should a circuit board be deemed defective.

FIG. 8 is prior art illustrating that the AIMD feedthrough connector assembly 10 or feedthrough capacitor connector assembly 20 may be designed for use with a "clam shell" style AIMD casing 32. A "clam shell" type AIMD casing 32 comprises two casing halves 112, 114 that are essentially mirror images of each other, meaning that the two casing halves appear almost identical, but are reversed in the direction perpendicular to the mirror surface. The two casing halves 112, 114 are brought together to form an AIMD casing 32.

Referring once again to prior art FIG. 8, illustrated is that the terminal pin connector 16 is mechanically and electrically attached to the AIMD active electronic circuit board 106. The AIMD hermetically sealed feedthrough 14 is shown with the corresponding terminal pins 18, 18gnd plugged into the terminal pin connector 16. There is also an internally grounded feedthrough capacitor 24' that is disposed on the inside of the AIMD casing 32. In FIG. 8, the internally grounded feedthrough capacitor 24' does not have an external, perimeter or outer metallization layer; instead, the internally grounded feedthrough capacitor 24' is grounded to the terminal pins 18gnd residing at both ends of the ground terminal pins. These ground terminal pins 18gnd are either gold brazed, or laser welded directly to the ferrule 26 and provide a solid mechanical and low impedance RF ground for the internally grounded feedthrough capacitor 24'. This is a convenient way of providing grounds to the AIMD active electronic circuit board 106. In FIG. 8, there are five active terminal pins 18 and the two ground terminal pins each labeled 18gnd.

Referring once again to FIG. 8, illustrated is one casing half 112 of the AIMD casing 32, which can have a multiplicity of shapes, of which only one exemplary shape of many shape possibilities (including customized shapes) is shown. Illustrated is a ferrule 26 fitted into an opening in an AIMD casing 32 such that a laser weld can be made hermetically sealing the AIMD pulse generator. It is noted that the ferrule 26 in FIG. 8 may comprise an H-flange 30 as shown in FIGS. 3, 3B and 3C, which captures the casing half 112, or alternatively, ferrule 26 may comprise an L-flange, an F-flange, an indent flange or a barrel flange, including the flange configuration shown in FIG. 8. It will be appreciated that the ferrule 26 of FIG. 8 is only a non-limiting exemplary configuration, thus ferrule and AIMD casing configurations may vary.

FIG. 9 illustrates prior art embodiments of terminal pin connectors 16, 16' and 16" for use with an AIMD hermetically seal feedthrough 14 having a staggered terminal pin 18 configuration. It is understood by one skilled in the art that terminal pin connectors may be shaped, positioned, oriented, or otherwise mounted to accommodate any terminal pin configuration of an AIMD hermetically sealed feedthrough 14, including one of a staggered terminal pin configuration, a dual in-line terminal pin configuration, or a custom terminal pin configuration. Referring once again to the terminal pin connecters of FIG. 9, terminal pin connector 16 is configured as previously disclosed in the present application. The embodiment of terminal pin connector 16' provides height to the terminal pin connector, thereby having an elevated insertion though-bore with respect to that of the terminal pin connector 16 so that the terminal pin connector 16' suitably aligns with a respective staggered terminal pin. To save weight, terminal pin connector 16' may comprise an optional cutout 188 as illustrated. The embodiment of terminal pin connector 16" essentially embodies the shape of the terminal pin connector 16', except that the terminal pin connector 16" comprises a flat cutoff that is attached to a conductive spacer block 190. The conductive spacer block 190 may be electrically attached to at least one of the circuit board electrical connection pad 104 as shown, a circuit board trace 105 (not shown) or a circuit board land (not shown). It is noted that the alignment feature 75 of the terminal pin connectors 16 of FIG. 9 are disposed so that the alignment feature 75 overhangs the edge of the AIMD active electronic circuit board 106 to facilitate a flat attachment for proper bonding and electrical connection 107' to the circuit board electrical connection pad 104. The circuit board electrical connection pad 104 area is sufficiently large to allow robotic dispensing of solder dots, ball grid arrays and the like.

FIG. 10 illustrates a prior art embodiment of a terminal pin connectors 16" and 16'" suitable for a dual in-line terminal pin 18 configuration. In this case, the terminal pins 18 are vertically aligned one above the other. The hermetically sealed feedthrough 14 of FIG. 10 comprises eight hermetically sealed terminal pins 18 extending through the insulator 28 of the AIMD hermetically sealed feedthrough 14 from a body fluid side to a device side. After the AIMD casing 32 is hermetically sealed by joining can haves 112, 114, the device side of the insulator 28 is inside the AIMD casing 32 and the body fluid side is outside the AIMD casing 32. The terminal pin connectors illustrated in FIG. 10 are staggered to accommodate insertion of each terminal pin of the dual in-line terminal pin configuration into its respective terminal pin connector. The terminal pin connectors can be attached either using a BGA dot or a thermal-setting conductive adhesive dot or an edge electrical connection. In the embodiment of FIG. 10, terminal pin connector 16'" accommodates the shorter terminal pins 18', while terminal pin connectors 16" accommodates the longer terminal pins 18. The short and long terminal pin configuration ensures that only terminal pin 18' are inserted into terminal pin connector 16'" and only terminal pin 18 are inserted into terminal pin connector 16". Additionally, the height of terminal pin connectors 16''' is defined such that terminal pins 18 will not make contact to terminal pin connectors 16'''. Terminal pin connectors 16'' have a separate open spacer block 190', however it is contemplated that terminal pin connectors 16'' can comprise a solid spacer block. Additionally, the terminal pin connectors 16'' may also be a one-piece structure instead of a multi-piece structure as shown. Multi-piece terminal pin connector structures will have an electrical connection 107' as shown. The spacer block 190' is attached to circuit board electrical connection pads 104 (or alternately to circuit traces or circuit board lands not shown) as previously described for terminal pin connector 16. The through-bore of the terminal pin connector 16'' is spatially aligned to line up along the axis of the length of the terminal pins 18 of the hermetic feedthrough 14 so that insertion of the terminal pin distal end can be made. Importantly, during insertion of the AIMD active electronic circuit board 106, terminal pins 18 and 18' should be assembled such that, when the AIMD active electronic circuit board 106 is attached to the terminal pins 18 and 18', the terminal pins will not substantially deflect or bend. Depending on the terminal pin material of construction, either the terminal pins can have an applied force such as by a fixture to prevent deflection and/or bending during the insertion process, or the terminal pins may have a specified material composition and/or properties, as terminal pin materials can then be specifically chosen based on a material's flexural strength, which is the amount of bending force a material can withstand without being substantially deflection or compromisingly bent.

FIG. 11 illustrates a prior art active implantable medical device 12 known as an implantable cardioverter defibrillator (ICD). An ICD has a hermetically sealed metallic AIMD casing 32 generally of titanium. An ICD also comprises an AIMD header block 118 into which therapy delivery leadwires routed to the heart are plugged as shown. Illustrated are ISO international standard industry lead connectors IS-1 and DF-1. An IS-1 lead connector is a low-voltage pacing/sensor lead connector. A DF-1 lead connector is a high-voltage shock lead connector. A first leadwire is shown routed to the right ventricle of the heart, which, in this case has one IS-1 lead connector and two DF-1 lead connectors, the three lead connectors joined together at a yoke integrating these lead connectors into the single lead body illustrated. The first leadwire comprises a coil electrode at the Superior Vena Cava (SVC), and both a coil electrode and a ring electrode in the right ventricle. The second leadwire comprising a ring electrode is shown routed to the right atrium. This embodiment represents a standard dual chamber pacing system with defibrillation capabilities. It is understood that a variety of therapy delivery leadwire configurations are possible as are a multitude of locations that electrodes can be routed transvenously to contact either the myocardium of the heart or that floats in the heart blood pool.

FIG. 12 shows a prior art biphasic characteristic ICD pulse and which occurs very quickly. The ICD pulse exhibits a $V_{MAX}$ at the plus (+) sign along with some overshoot with ringing. Such high-frequency ringing is due to an inductance between the uncharged EMI filter capacitor 24, 24', 24'' and the high-energy storage capacitor (not shown) of the ICD. The plus (+) sign is indicated at the first phase of the biphasic pulse (which, as shown, is positive), while a minus (−) sign is indicated at the second phase of the biphasic pulse (which, as shown, is a negative). In general, the use of plus (+) or minus (−) signs is arbitrary because implanted biphasic ICDs deliver current in two directions. In the first phase, current moves from one implanted electrode along the cells of heart tissue to the other implanted electrode. During the second phase, the current flow reverses direction. As such, in the embodiments of the present application, it is understood that a plus (+) sign assigned, for example, to an active terminal pin or leadwire and a minus (−) sign assigned, for example, to system ground, is also arbitrary due to the fact that biphasic ICDs deliver current in two directions, which means that, when a patient's heart is subjected to a defibrillation cycle, the active terminal pin or leadwire and the system ground change positive (+) and negative (−) polarities when the current direction of the first phase of the pulse reverses direction in the second phase, thereby completing one biphasic defibrillation cycle. It is appreciated that device programming and device architecture can define which terminal pins or leadwire (active or ground) are positive (+) and which are negative (−) at any particular time and in any particular filtered feedthrough embodiment.

Referring now to prior art FIG. 13, one can see that the prongs 70 are captured in a notch 61 of the terminal pin 18. The notch of FIG. 13 illustrates corners that essentially have right angles. As such, the notch 61 enables the prongs 70 to more firmly grip the terminal pin 18. Such a firmer grip of the terminal pin 18 may require increased pull force of a terminal pin connector 16 for removal from the terminal pin 18. In the case of required increased pull force, removal of the terminal pin connector 16 can be facilitated by use of a tool, such as a slender tool inserted into and along the alignment flange 75' into the connector housing through-bore 78 of the connector housing 66 to push prong 70 outwardly from the terminal pin 18 thereby opening the prong 70 and facilitating release from the terminal pin 18. A tool is not illustrated, however, could be a structure similar to a dental pick or other a slender probe that could slide along the terminal pin 18 between the terminal pin and the prong 70, thereby opening the prong 70.

An alternative for releasing the prong 70 from the notch 61 of the terminal pin 18 of FIG. 13 would be to manufacture the prong of a shape-memory alloys such as, but not limited to: Nitinol (a nickel-titanium alloy: TiNi), or a Nitinol-based alloy, a copper-based shape-memory alloy (such as copper-aluminum-nickel alloy: Cu—Al—Ni or copper-zinc-aluminum alloy: Cu—Zn Al) or an iron-based shape-memory alloy (using iron alloyed with, for example, zinc, copper, and gold or an iron-manganese-silicon alloy: Fe—Mn—Si).

FIG. 14A illustrates a prior art spring clip 64''' consisting of one or more waved tines 79. This is best shown in FIG. 14B, which is an enlarged view of the spring clip 64'''. FIG. 14B illustrates the waved tines 79 of the spring clip 64''' having a flat tine end, however, any configuration at the end of the tine may be used, such as curved, pointed or radiused. As previously described, it is very important that the spring rate be adjusted so that a tight grip be formed on the electrical conductor 122 (or leadwire or terminal pin) and at the same time, the elastic limit of the materials of 64''' are not exceeded.

Referring once again to FIG. 14A, the terminal pin connectors 16 are also shown on the body fluid side, but it is contemplated that they could be attached to an AIMD active electronic circuit board 106, or an EMI filter circuit board 106' as implied by the device side portion of FIG. 14A. Regarding the device side portion of FIG. 14A, the circuit boards 106, 106' would reside inside the hermetically sealed casing 32 (not shown) of the AIMD 12 and the terminal pin connector 16 would, therefore, not need to be biocompatible. Accordingly, when disposed on the device side of an AIMD, the terminal pin connectors 16 of FIG.

14A do not need to comprise biocompatible, biostable and non-toxic materials, thus constantan could be effectively used.

FIG. 15 is another prior art embodiment illustrating the terminal pin 18, 18' comprising a compliant termination structure 81 having a spring-like elastically resilient press-in zone that can be inserted or 'press fit' into a conductive plated or terminated circuit board via hole 109 having circuit traces (not shown) routed to them. Such a compliant termination structure 81 can be integrated with the device side portion of a two-part pin 18', while the body fluid side portion of a two-part pin 18 comprises a biocompatible biostable non-toxic terminal pin, thereby providing a unique cost-effective AIMD hermetically sealed feedthrough 14 embodiment.

Referring once again to prior art FIG. 15, illustrated on the left-hand side is a via hole eyelet 194, which can be a formed eyelet (that is, a thin stamped, machined or the like) or, as shown on the right-hand side, an electroplated or metallized via hole 109 of any type known in the prior art can be provided into which a connector housing 66 may be inserted. Alternatively, on the right-hand side, a much heavier duty eyelet 194 can been inserted instead of connector housing 66, which can either be soldered (or otherwise equivalently electrically connected), or, depending on the size, material of construction and circuit board material and/or thickness, can be press-fit into via hole 109. A heavier duty eyelet 194 or a connector housing 66 serves to mitigate stresses imparted during pin insertion 18', thereby inhibiting crack initiation preventing cracking or damaging of delicate AIMD active electronic or EMI filter circuit boards 106, 106'. As such, in accordance with the embodiments of the present application, this heavier eyelet structure 194 or the connector housing 66, may comprise at least a partial flange 75 (not labelled), as illustrated. While FIG. 15 shows a specific embodiment the compliant termination structure 81 of terminal pin 18' engaging the eyelet 194 or connector housing 66, it is understood by one skilled in the art that the shape of the terminal pin compliant termination structure 81 can be of any configuration designed to achieve the required eyelet 194 or connector housing 66 engagement.

FIG. 15A is another prior art embodiment of a compliant termination structure 81'. The compliant termination structure 81' may be monolithically formed when terminal pins 18, 18' are formed (not shown), or alternatively may be separately formed and joined to terminal pins 18, 18' by a weld or a braze (the weld or braze is labelled 144 in FIG. 15A). Similarly, the embodiments of the compliant termination structures 81' of FIGS. 15 and 15A-15D can be monolithically formed when terminal pins 18, 18' are formed, or alternatively may be separately formed and joined to terminal pins 18, 18' by a weld or a braze.

FIG. 15B is another prior art embodiment of a terminal pin 18, 18' with a compliant termination structure 81". In this embodiment, the terminal pin 18, 18' extends through the compliant termination structure 81" and illustrates a first weld or braze 144 and/or a second weld or braze 144' for attachment of the compliant termination structure 81" to terminal pin 18, 18'.

FIG. 15C is yet another prior art embodiment of a terminal pin 18, 18' with a compliant termination structure 81'''. In this case, having inwardly angled prongs.

FIG. 15D is yet another prior art embodiment of a terminal pin 18, 18' with a compliant termination structure 81'''' that has a rounded prong ends that facilitate insertion.

It is noted herein that, when any embodiments of terminal pin connectors 16, terminal pins 18, 18', 18$gnd$ or the compliant termination structures 81' are used on the body fluid side of the AIMD, the embodiments must be made of biocompatible, nontoxic, and biostable materials. Likewise, when any embodiments of terminal pin connectors 16, terminal pins 18, 18', 18$gnd$ or the compliant termination structures 81' are used on the device side, which is the inside of the AIMD, the embodiments do not need to be biocompatible, nontoxic, or biostable. It is also understood that any compliant termination structures disclosed herein including the compliant termination structures of prior art FIGS. 15-15D can be separately manufactured from the terminal pin 18, 18', 18$gnd$ or alternately could be made as part of the terminal pin 18, 18', 18$gnd$ in one monolithic structure. It is also contemplated that any compliant termination structure disclosed herein including the compliant termination structures of FIGS. 15-15D can be integrated into any AIMD terminal pin or AIMD header block electrical conductor or leadwire for insertion into connector housings 66, circuit board eyelets 194, or cavities 180 taught herein.

FIG. 16 illustrates a prior art connector housing 66 of an exemplary terminal pin connector 16 of the present application with an alternative prong 70, as illustrated. It is noted herein that any of the connector housing embodiments of the present application may be used instead of the connector housing 66 shown. The prongs 70 of FIG. 16 are shown in cross-section. It is contemplated that they can be 2, 3, 4 or even "n" number of prongs. Prongs 70 could be laser welded or brazed 144 to clip 64, as indicated, or prongs 70 could alternately be crimped. If disposed on the device side (inside the hermetically sealed AIMD casing 32), then the mechanical and electrical connection of element 144 need not be biocompatible and could comprise solder, thermal-setting conductive adhesives and the like. However, if prongs 70 reside on the body fluid side, then mechanical and electrical would require a laser weld 144.

FIG. 17 is prior art similar to FIG. 16, except in this case, the prongs 70 are now attached to a spring clip 64'. The spring clip 64' provides additional insertion capability to both sides of its structure such that prongs 70 can be inserted into a connector housing 66 as illustrated or into a circuit board via hole 109 or a cavity 181 (not shown) and terminal pin 18, as illustrated (or a two-part terminal pin either 18 or 18' not shown), can be inserted into spring clip 64'. In other words, there would no longer be a need for the mechanical and electrical connection previously labelled in FIG. 16 as element 144. The distal end 62 of the terminal pin 18 is inserted into the spring clip 64', making a robust, alternative mechanical and very low resistance electrical connection 181. When the prongs 70 are inserted inside the connector housing 66, the spring rate and the tolerances are adjusted such that the prongs 70 end up compressed very tightly against the inside diameter of the housing 66. This makes for a very robust alternative mechanical and electrical connection, which can either be on a circuit board or on an AIMD header block.

FIG. 18 illustrates a prior art alternative AIMD hermetically sealed feedthrough 14 comprising co-sintered conductive paste-filled vias 146 formed by co-sintering a conductive paste residing in the via of the insulator 28 at the same time that the insulator 28 is sintered. The co-sintered conductive paste-filled via 146 can be of a substantially pure platinum or a ceramic reinforced metal composite (CRMC). Co-sintered platinum filled vias are described by U.S. Pat. Nos. 8,653,384; 8,938,309; 9,233,253; 9,352,150; 9,511,220; 9,511,220; 9,889,306 and 9,993,650, the contents of which are fully incorporated herein by these references. Co-sintered ceramic reinforced metal composite (CRMC)

conductive vias are described by U.S. Pat. Nos. 10,272,253 and 10,249,415, the contents of which are also fully incorporated herein by these references.

Referring once again to FIG. 18, illustrated are two embodiments, one on the left comprising a cavity 181 formed within a co-sintered conductive paste-filled via 146 into which a compliant terminal pin structure 81 (i.e., a spring-like elastically resilient structure) is inserted; and one on the right comprising a terminal pin 18 co-fired with a co-sintered conductive paste-filled via 146 to which the distal end 62a of terminal pin 18 is electrically connected to a terminal pin connector 16. The compliant termination structure 81 has prongs 70 inserted into the cavity 181.

FIG. 19A illustrates a prior art connector housing 66 and/or a terminal pin connector 16 that can be disposed either on the body fluid side or the device side of a hermetically sealed feedthrough 14. Such connector housings 66 and/or a terminal pin connectors 16 are electrically connected one or more co-sintered conductive paste-filled vias 146, the one or more co-sintered paste filled vias 16 comprising one of a pure platinum co-sintered conductive paste-filled via 146, a pure platinum co-sintered conductive paste-filled via 146 having a CRMC 147 co-sintered layer, or combinations thereof. FIG. 19A illustrates an embodiment where a connector housing 66 comprising an integrally formed post 77 co-sintered within a co-sintered conductive paste-filled via 146 (see the embodiment shown on the body fluid side of the left-hand side of FIG. 19A and the embodiment on the device side of the right-hand side of the co-sintered conductive paste-filled via 146 of FIG. 19A). Alternatively, the connector housing 66 may be brazed or welded for attachment to the co-sintered conductive paste-filled via 146 (see the embodiment shown on the body fluid side of the right-hand side of FIG. 19A and the embodiment on the device side of the left-hand side of the co-sintered conductive paste-filled via 146 of FIG. 19A). FIG. 19A also illustrates that either the connector housings 66 or the electrical conductors 122 can comprise compliant termination structures (see the exemplary clips comprising prongs 70 within connector housings 66 on the device and body fluids sides on the left-hand side of FIG. 19A, and prongs 70 of the compliant termination structure at the distal end of the terminal 18 on the right-hand side of FIG. 19A). When such compliant termination structures are used on the body fluid side, the compliant termination structures would be made of a biocompatible, nontoxic, and biostable material. Likewise, when the compliant termination structure is used on the device side inside the AIMD, the compliant termination structures do not have to comprise a biocompatible, nontoxic, or biostable material.

FIG. 19A illustrates a prior art connector housing 66 and/or a terminal pin connector 16 (FIG. 19B) that can be disposed either on the body fluid side or the device side of a hermetically sealed feedthrough 14. Such connector housings 66 and/or a terminal pin connectors 16 are electrically connected one or more co-sintered conductive paste-filled vias 146, the one or more co-sintered paste filled vias 16 comprising one of a pure platinum co-sintered conductive paste-filled via 146, a pure platinum co-sintered conductive paste-filled via 146 having a CRMC 147 co-sintered layer, or combinations thereof. FIG. 19A illustrates an embodiment where a connector housing 66 comprising an integrally formed post 77 co-sintered within a co-sintered conductive paste-filled via 146 (see the embodiment shown on the body fluid side of the left-hand side of FIG. 19A and the embodiment on the device side of the right-hand side of the co-sintered conductive paste-filled via 146 of FIG. 19A). Alternatively, the connector housing 66 may be brazed or welded for attachment to the co-sintered conductive paste-filled via 146 (see the embodiment shown on the body fluid side of the right-hand side of FIG. 19A and the embodiment on the device side of the left-hand side of the co-sintered conductive paste-filled via 146 of FIG. 19A). FIG. 19A also illustrates that either the connector housings 66 or the electrical conductors 122 can comprise compliant termination structures (see the exemplary clips comprising prongs 70 within connector housings 66 on the device and body fluids sides on the left-hand side of FIG. 19A, and prongs 70 of the compliant termination structure at the distal end of the terminal 18 on the right-hand side of FIG. 19A). When such compliant termination structures are used on the body fluid side, the compliant termination structures would be made of a biocompatible, nontoxic, and biostable material. Likewise, when the compliant termination structure is used on the device side inside the AIMD, the compliant termination structures do not have to comprise a biocompatible, nontoxic, or biostable material.

FIG. 20 illustrates a prior art embodiment similar to FIG. 19B, except the chamfer 150 configuration of the connector housing 66 is different. When the prongs 70 at the distal end 62 of the terminal pin 18 are inserted into the chamfer 150 configuration of the connector housing 66 of FIG. 20, the prongs 70 are mechanically compressed as the prongs 70 slide along the chamfer 150 ultimately electrically engaging the inside diameter of the narrowed through-bore along longitudinal axis A-A.

FIGS. 21 and 22 are prior art taken from FIGS. 51 and 52 of U.S. Pat. No. 10,272,252, the contents of which are fully incorporated herein by this reference. Referring to FIG. 21, one can see that there is an AIMD hermetically sealed feedthrough 14 which may have one-part or two-part terminal pins 18, 18', as has been previously disclosed. Disposed on the device side is an EMI filter circuit board 106'. The EMI filter circuit board 106' may have one or more internal ground electrode plates 156, as illustrated. Circuit board ground electrode plates 156 are more thoroughly described in U.S. Pat. Nos. 8,195,295 and 10,272,252, the contents of which are fully incorporated herein by these references. Referring once again to FIG. 21, the EMI filter circuit board 106' may be disposed against at least one of the device side of the insulator 28 and/or the ferrule 26 or an insulating washer (not shown) may be disposed between the EMI filter circuit board 106' and at least one of the insulator 28 and the ferrule 26. Alternatively, the EMI filter circuit board 106' may be disposed along the terminal pins 18 and 18gnd at some distance from the ferrule 26 or the insulator 28 thereby providing a gap between the EMI filter circuit board 106' and at least one of the insulator 28 and the ferrule 26. As shown in FIG. 21, the EMI filter circuit board 106' is immediately adjacent both the alumina insulator 28 and the ferrule 26, but as has been stated, it need not be adjacent. Rather, it could be spaced away, even at some substantial distance, from one of the insulator 28, the ferrule 26, or both.

Referring once again to prior art FIG. 21, one can see that there is a terminal pin connector 16 associated with each one of the active terminal pins 18 and also the ground terminal pins 18'gnd and 18'gnd'. It is contemplated that, while two ground terminal pins are illustrated, any number (n) of ground terminal pins can be present. As previously described, these terminal pin connectors 16 would be populated on the main AIMD active electronic circuit board 106 (not shown). Accordingly, each one of the active terminal pins 18 would be routed to active traces 162 of the AIMD active electronic circuit board 106. At least one ground terminal pin 18'*gnd* (or 18'*gnd'*) would be routed to an AIMD active electronic circuit board 106 ground electrode plate 52, ground trace or ground plane (not shown). As previously indicated, this is useful for AIMDs 12 that sometimes use the AIMD casing 32 as an electrode. The active pins are terminal pins 18*a* through 18*f*. The left-hand side ground terminal pin 18*gnd* resides in a ferrule counterbore. The ground terminal pin 18*gnd* may alternatively be attached to the device side ferrule surface 26' and may even comprise a nail head feature to facilitate ground terminal pin attachment (not shown). The right-hand side ground terminal pin 18'*gnd'* goes all the way through the hermetically sealed feedthrough 14 such that it can also be connected on the body fluid side. Some of these active terminal pins 18*a*-18*f* may be used to sense biological signals. Others may be used to provide therapeutic pulses or in the case of an implantable cardioverter defibrillator (ICD), pairs of these leads could be used to provide high voltage cardioversion therapy to cardiovert the heart from dangerous rhythms to normal sinus rhythm. Referring once again to FIG. 21, it is contemplated that in an ICD application, terminal pin 18*a* could be routed to a distal shocking electrode, for example, in the right ventricle of the superior vena cava. The AIMD active electronic circuit board 106 could be programmed such that the opposite polarity of the shocking biphasic wave form could be applied to terminal pin 18*gnd*. This is called a 'hot can' wherein, the shocking vector would be between the distal electrode located inside the heart, back to the AIMD casing 32. So, by having terminal pin 18*gnd* connected to the AIMD active electronic circuit board 106 (not shown), this provides for a number of alternatives. Pacing vectors like this are also very important for spinal cord stimulators where sometimes the AIMD casing 32 itself is used as part of the pacing vector.

Referring once again to prior art FIG. 21, one will see that the EMI filter circuit board 106' has a number of filter capacitors 154. As described in U.S. Pat. Nos. 10,272,252 and 8,195,295, these could be MLCCs 154, otherwise known as monolithic multilayer ceramic capacitors, or X2Y attenuators 300 or flat-thru capacitors 400. Each one of these capacitors 154, 300, 400 has one or more active electrode plates that are electrically connected to active terminal pins 18*a* through 18*f*. Referring once again to FIG. 21, this particular embodiment has six (6) poles (6 active terminal pins) with two (2) ground terminals 18'*gnd* and 18'*gnd'*. As illustrated in FIG. 21, the ground terminal pins 18*gnd* and 18*gnd'* are either laser welded 160 or gold brazed 165 to the ferrule 26. Brazing or welding the ground pins 18*gnd* and 18*gnd'* permits penetration through any oxides present on the ferrule 26 thus forming a very low resistance metallurgical electrical connection. This metallurgical electrical connection has been shown to be very stable and generally will not form oxides over time. Further, by using ground pins comprising a suitable oxide-resistant material, such as platinum, a further essentially oxide-free electrical connection can be made to the ground pin. For example, in addition to the already mentioned AIMD components, that is, circuit boards or header blocks, and the electrical components: MLCCs, X2Y attenuators or flat-thru capacitors, the essentially oxide-free electrical connection can be made between the oxide-resistant ground pins 18*gnd* and 18*gnd'* to a ground electrode, a ground circuit trace, a ground via of a circuit board, or to an edge ground metallization of the circuit board or of the electrical components. The essentially oxide-free electrical connection can be a direct electrical connection to the oxide-resistant ground pin, or, alternatively, the electrical connection may be made using an electrical connection material such as a solder, a thermal-setting conductive adhesive or the like. Hence, for the above reasons, all ground terminal pins of the AIMD device can comprise an oxide-resistant, namely an essentially oxide-free, material. For example, the oxide-resistant ground terminal pins 18'*gnd* and 18'*gnd'* can comprise a noble metal. Additionally, the oxide-resistant ground pins 18*gnd* and 18*gnd'* can comprise platinum, gold, tungsten, iridium, palladium, niobium, tantalum, ruthenium, rhodium, silver, osmium, and alloys or combinations thereof. Further, the oxide-resistant ground pins 18'*gnd* and 18'*gnd'* can comprise platinum-based materials including platinum-rhodium, platinum-iridium, platinum-palladium, or platinum-gold, including naturally occurring alloys such as platiniridium (platinum-iridium), iridiosmium and osmiridium (iridium-osmium). It is important to note herein that the oxide-resistant ground pins are hermetic (see 18'*gnd'*) and provide strong mechanical and low resistance electrical attachment to the ferrule 26. Importantly, such attachment of oxide-resistant ground pins 18*gnd* to the ferrule 26 further provides very low impedance connections at high frequencies, which is necessary to divert dangerous electromagnetic interference (EMI) signals. Of significance is that oxide-resistant ground terminal pins 18'*gnd* and 18'*gnd'* can themselves provide for connections having low resistance and low impedance at high frequencies regardless of the metal used to form the ferrule, providing new design opportunities not only for AIMDs, but other types of "smart" medical devices, whether implanted, temporarily implanted, or external the body, for example, sensors, monitors, identification tags, recorders, controller, artificial organs and the like. Such oxide-resistant materials should also be capable of high processing temperatures to sustain oxide formation resistance.

FIG. 22 is prior art taken from section 22-22 of FIG. 21 illustrating the top view of the EMI filter circuit board 106' disposed at, near or distant from the ferrule 26. In this case, each one of the capacitors 154*a*-154*f* is directly connected either through a circuit trace 162, as shown, or a direct solder connection or thermal-setting conductive adhesive connection or the like, from the MLCC 154 active electrode plates to each of the six active terminal pins 18. The ground electrode plates of the MLCCs 154 are connected to via holes which communicate with the at least one internal ground electrode plate 156 of the EMI filter circuit board 106'. In this way, the capacitors are connected both to the active pins and to the effective RF ground, which diverts unwanted high frequency energy from the terminal pins 18 through the filter capacitor to the ground plate and in turn, to the ferrule 26 and then to the AIMD casing 32, which together acts as an overall Faraday shield. This Faraday shield prevents the EMI from entering the AIMD casing 32 and instead causes the dangerous unwanted EMI RF energy to circulate harmlessly as eddy currents in the AIMD casing 32 without penetrating inside the AIMD casing where it could undesirably couple to sensitive AIMD circuitry and cause AIMD malfunction. It is noted herein that certain AIMD malfunctions can be life-threatening to a patient.

Referring once again to FIG. 22, one can see that each of the MLCCs 154 are grounded to a via hole or a circuit trace labeled gnd a-gnd f. These via holes are disposed through the circuit board and contact at least one ground electrode plate 156, which as previously described, is connected to the ferrule 26, thereby, providing a low impedance RF ground.

Referring once again to prior art FIG. 22, the exemplary circuit traces 162 only show one embodiment, in this case, for MLCCs 154. It is contemplated that, for the X2Y attenuators 300, the circuit traces would be modified to make at least two active connections to the X2Y attenuator, which would then have at least one ground connection. For example, MLCCs 154 could also be replaced by flat-thru capacitors 400. In this case, the circuit traces would be different, in that, there would be a third terminal connected to the flat-thru capacitors 400, which would be grounded, and the circuit trace currents would go through the flat-thru capacitor. Such flat-thru capacitors are all more thoroughly disclosed in U.S. Pat. No. 10,272,252, which is incorporated herein by reference.

FIG. 23A is a prior art isometric view of a prior art surface mounted capacitor that is also known by those skilled in the art as an X2Y attenuator 300. The X2Y attenuator was originally invented by the X2Y Attenuator® company. The X2Y attenuators are sold by Knowles/Syfer® and the Knowles/Syfer online catalogs are publicly accessible. In addition, the X2Y Attenuator company has approximately 72 patents assigned to them, some of which have been licensed to Knowles/Syfer. There are many variations to the X2Y attenuator 300 and only one embodiment is shown herein (see FIG. 23A). FIG. 24A illustrates how X2Y attenuator 300 can be attached to the EMI filter circuit board 106' of the present application. It will be understood by one skilled in the art that variations of the X2Y attenuators, including those described in the X2Y patents, could be used by adjusting the circuit board 106' circuit traces and the related physical embodiments disclosed herein. X2Y attenuators are so well known in the prior art that the inventors have not described all of the variations and shapes that are possible so as not to obfuscate the present application.

Referring once again to prior art FIG. 23A, illustrated is an X2Y attenuator 300 having a dielectric body 314 comprising metallized terminations 301 and 302. As will be further described, the metallized terminations 301 and 302 are electrically conductive and solderable and will also accept a thermal-setting conductive adhesive such that these metallized terminations 301 and 302 can be connected to terminal pins 18, 18gnd or to circuit traces 418, 418gnd. Referring once again to FIG. 23A, one will see that there is a ground termination 304, as shown. This ground termination 304 of FIG. 23A comprises a continuous metallization band centrally located all of the way around the surface mounted X2Y attenuator, however, it is appreciated that the ground metallization 304 about the surface mounted X2Y attenuator could also be discontinuous. A ground connection 306 is made such that electromagnetic interference (EMI) signals from conductors attached to the metallized terminations 301 and 302 can be capacitively decoupled at the ground connection 306 to a system ground (not shown), which, for an AIMD application, can comprise the ferrule 26 or the flange 30 of the ferrule 26, which is designed to be electrically connected to the overall AIMD casing 32 of the AIMD 12. As previously disclosed, this overall AIMD casing 32 adds an electromagnetic shield or Faraday cage to which undesirable high-frequency EMI signals may be diverted or decoupled (filtered).

FIG. 23B is taken from section 23B-23B of prior art FIG. 23A. The sections illustrated in FIG. 23B represent different depths of the X2Y attenuator of FIG. 23A showing various layers through section 23B-23B. Referring back to FIG. 23A, the X2Y attenuator 300 has a dielectric body 314 as indicated. The dielectric body 314 may be a ceramic dielectric, such as a barium titanate, a strontium titanate or the like. In low capacitance values, the dielectric body 314 could even be an alumina ceramic or any type of ceramic structure. The dielectric body 314 may also comprise various insulative films, such as mylar (otherwise known as a stack-fill capacitor), Kapton® or many other types of film capacitors. It will also be appreciated that the dielectric body 314 could comprise a tantalum capacitor or an electrolytic capacitor. Referring now to FIG. 23B, one can see the active electrode plate 308 in the illustration at the top of FIG. 23B is associated with capacitance area Ca. The active electrode plate 308 is a conductive layer, which is connected to the metallized termination 301. The conductive layer shown in the middle illustration of FIG. 23B is a ground electrode plate 310 configured to be connected to the metallization termination 304. It is noted herein that the metallization terminations 304 and 306 of the X2Y attenuator of FIG. 23A can be continuous as shown or discontinuous (not shown). The conductive layer shown at the bottom of FIG. 23B is an active electrode plate 312, which is connected to metallization termination 302 and is associated with capacitance area Cb. It is the overlap of the active electrode plate 308 with ground electrode plate 310 that forms the capacitance Ca. Likewise, it is the overlap of active electrode plate 312 with the ground electrode plate 310 that forms the capacitance area Cb. As will be shown, by selectively eliminating the ground electrode plate, an electrode plate stack up may comprise ten, twenty, thirty or even hundreds of conductive layers. In so doing, one can form and/or tailor a capacitance between the capacitance Ca and the capacitance area Cb. FIG. 23B presently illustrates a ground electrode plate 310 that electrostatically shields the capacitance area Ca of the active electrode plate 308 from the capacitance area Cb of the active electrode plate 312. Therefore, the line-to-line capacitance Ca-b would be trivially small. So, it is only when one selectively removes the ground electrode plate 310, that one achieves a high effective capacitance area between active electrode plates 308 and 312 such that significant line-to-line capacitance will be achieved.

The specific type of electrical connection is not important as it may encompass a circuit trace (not shown), a circuit trace landing pad (not shown), direct connection to vias/via holes (only partially shown), or plated or metallized vias. Referring once again to FIG. 24A, one can see the ground metallization termination 304 of the X2Y attenuator 300. In order to provide very low impedance RF grounding, the ground metallization termination 304 has been electrically connected to two grounded via holes gnd a,b and gnd a',b'. Short circuit traces 418 are shown between the ground via holes and the ground metallization termination 304 of the X2Y attenuator 300. These circuit traces 418 may be long or may be eliminated simply by moving the ground via holes closer to the capacitor ground metallization termination 304 such that a direct connection can be made to the via holes. Such a change to the active traces can similarly be made.

FIG. 24B is a sectional view taken along section lines 24B-24B of prior art FIG. 24A.

Now referring to FIG. 24C, illustrated is a schematic of the X2Y attenuators 300 previously described in FIGS. 23A, 23B, 24A AND 24B. One can see that capacitance areas Ca and Cb are both connected to ground 26, 30. Ground 26, 30 is a ground to the ferrule 26, which becomes the system ground once the ferrule is welded to the AIMD casing 32. Referring once again to FIG. 24B, a line-to-line capacitance Ca-b may be formed between terminal pins 18a and 18b. As previously described in FIG. 28B, this line-to-line capacitance Ca-b would be made by selective elimination of ground electrode plates 310 such that an effective capacitance area (ECA) develops between Ca and Cb. It is noted herein that not all of the ground electrode plates 310 can be removed. If this were the case, then Ca and Cb capacitance would not even exist. Therefore, ground electrode plates 310 may only judiciously removed selectively. To EMI specialists, such judicious elimination of ground electrode plates is known as balancing the common mode filter attenuation with the differential mode filter attenuation. Differential mode means a differential signal between terminal pins 18*a* and 18*b*. This is understood more simply if one was to put a high-frequency voltmeter between terminal pins 18*a* and 18*b*, where one would read a voltage. The purpose of capacitance Ca-b is to divert the voltage so that the voltage cannot get into the inside the AIMD 12. This is called differential mode filter attenuation. Referring once again to FIG. 24B, capacitances Ca and Cb are shown both connected to ground 26, 30. Because they are both connected to a common point, this means they are also connected to each other as the schematic illustrates. The schematic, however, could be changed so that Ca and Cb are separated, with each connected to a ground symbol. It will be understood that such a connection is the same thing. This configuration is to protect against differential mode EMI. This is also easy to understand if one were to take a volt meter, say, on terminal pin 18*a* and place it between the terminal pin and the ferrule and one measured a high-frequency AC voltage, then the purpose of capacitance Ca is to attenuate or divert that differential mode EMI to the ferrule so that dangerous EMI will not enter into terminal pin 18*a* into the inside of the AIMD 12 where the EMI could therefore disrupt the proper operation of the electronic circuits of the AIMD.

FIG. 25A is known in the prior art as a flat-thru capacitor 400. This type of capacitor is unique in that circuit current actually passes through the electrodes of the capacitor itself. These capacitors are also commonly known in the prior art and are public sold online, including online catalogs for same that are also publicly accessible.

Referring once again to prior art FIG. 25A, one can see that the flat-thru capacitor 400 is similar to the X2Y attenuator 300 in that a first active metallization termination 402 and a second active metallization termination 406 resides at both ends of the flat-thru capacitor 400. The flat-thru capacitor 400 also has ground metallization terminations 404 and 404'. The ground metallization termination, in this case, 404 and 404' is shown discontinuous, but like for the X2Y attenuator, it is contemplated that this termination 404 and 404' could comprise a continuous band all the way around the capacitor, as illustrated for the X2Y attenuator of FIG. 23A. Current 410, i₁ is shown entering in from a circuit trace 418 to a circuit board landing pad 416 to which the metallization termination 402 is electrically connected using electrical connection material 420. The electrical connection material 420 is better shown on the right-hand side of the flat-thru capacitor 400 where the metallization termination 406 is electrically connected to circuit board landing pad 416'. The current 410, i₁ is conducted all the way through the capacitor very much like a feedthrough capacitor, except in this case as will be shown, the current passes through the capacitor's electrode plates. This makes the flat-thru capacitor very unique in the prior art. The circuit current 410, i₁, passes through the capacitor then exits on the right-hand side as the same circuit current 410', i, this time from circuit trace 418'.

FIG. 25B is taken generally from section 25B-25B of FIG. 25A. One will appreciate that electrode plate 412, when building a monolithic ceramic capacitor structure 408, have to be thin and lacey, so the structure does not de-laminate and remains monolithic. As used herein, the term "lacey," as it refers to an electrode plate, means that, instead of being a solid thick metal sheet, the electrode plate has a plurality of open spaces through its thickness (more like a window screen) through which grain growth can infuse and traverse the bulk ceramic dielectric during sintering. The distribution of open spaces doesn't have to be homogeneous like a window screen, but there does have to be sufficient amount of open space areas in the electrode plate so that during sintering, the grain growth of the bulk ceramic dielectric will penetrate through the electrode such that the entire capacitor anchoring the electrode plate to the bulk ceramic thereby forming a truly solid and monolithic conductive layer. This is in contrast to a bologna sandwich analogy, where the layers of bread and bologna easily separate and delaminate or otherwise are taken apart one from the other. For more information on delamination, one is referred to the paper entitled "DUAL ELECTRODE PLATE MLCC FOR HIGH VOLTAGE PULSE APPLICATIONS" presented at the Capacitor and Resistor Technology Symposium held on Mar. 6-10, 2000, at Huntington Beach, California, (ISSN 0887-7491), the contents of which are fully incorporated herein by this reference.

Electrode plate 412 is the active electrode plate through which the circuit current 410, i₁ passes all the way through. Therefore, it is desirable that there be a relatively high number of active electrode plates 412 stacked up in interleaved relationship such that sufficient cross-sectional area exists to thereby preclude a high resistance to the flow of the current 410, i₁. It is also desirable that active electrode plats 412 be relatively wide (possibly much wider than shown) such that the circuit current 410, i₁ does not encounter excessive resistance or inductance. Actually, in the case of FIG. 25B, the inductance of the electrode plates 412 is desirable in that the inductance is in series with the electromagnetic filtering of the flat-thru capacitor 400. As is well known to EMI engineers, series inductance can help reduce the amount of electromagnetic energy that can get inside of a structure, in this case, the AIMD casing 32. The inductance L, 422 of the embodiment of FIG. 25B is therefore highly desirable. Normally, for prior art feedthrough capacitors and MLCCs, an inductance is undesirable, as the inductance, as shown in the schematic of FIG. 26, would be in series between the capacitance and ground thereby degrading filter performance at high frequencies.

FIG. 26 is the schematic of the prior art flat-thru capacitor 400. The flat-thru geometry has an enormous advantage in that, any stray or parasitic inductance of the electrode plates shows up in series with the terminal pin 18 (18*a*). As previously described, this series inductance helps to attenuate undesirable EMI. The flat-thru capacitor 400 is grounded through the ground symbol to the ferrule 26 and in turn, to system ground (namely, the AIMD casing 32), as previously disclosed. A deficiency of the flat-thru capacitor is also illustrated in FIG. 26. That is, at extremely high frequency, EMI can couple (radiate) through the air between metallization terminations 402 and 406, or worse yet, from circuit trace 418 to circuit trace 418'. EMI cross-coupling depends on the geometry of the circuit, the spacing and size of the circuit traces and the size of the flat-thru capacitor, but, in general, such undesirable EMI cross-coupling does not happen until one is in the GHz frequency range, such as 3 GHz. Fortunately, the human body effectively absorbs and reflects EMI in the GHz region, particularly above 3 GHz, such that it is very difficult for extremely high frequency energy to penetrate very far inside the human body. Accordingly, the flat-thru capacitor 400 is an acceptable EMI filter tradeoff for use in active implantable medical devices that are designed to be placed inside the human body with leadwires also disposed inside the human body. The human skin, muscle and fats tend to reflect and absorb such extremely high energy, thereby compensating for the flat-thru capacitor's tendency for EMI to couple across the flat-thru capacitor 400.

FIG. 27 is prior art very similar to FIGS. 23 and 24A in that the embodiment of FIG. 27 shows the top view of the device side of an EMI filter circuit board 106'; however, now three flat-thru capacitors are mounted to the top surface of the EMI filter circuit board 106'. One can see flat-thru capacitor 400 disposed between terminal pins 18a and 18a'. Circuit current enters terminal pin 18a as undesirable EMI energy from the body fluid side (not shown) up to the top of terminal pin 18a and then the circuit current passes through the capacitor body of the flat-thru capacitor 400 to terminal pin 18a' and is then directed to the circuit board active electronic circuits of an AIMD active electronic circuit board 106. Metallization termination 402 is electrically connected with electrical connection material 420, such as a solder or a thermal-setting conductive adhesive to circuit via hole 18a. This electrical connection may comprise a circuit board landing pad, a circuit board trace or even internal circuit board traces (not shown). There are many ways to make an electrical connection between the flat-thru capacitor's metallization terminations 402 and 406 to the corresponding leads 18a and 18a' thereby electrically connecting to the metallization terminations. The ground electrode plates 414 of the flat-thru capacitor 400 are electrically connected to ground vias gnd a and gnd a'. In the embodiment of FIG. 27, there are short circuit traces shown, but as previously described for the X2Y attenuator, these short circuit traces are not necessary as the via holes gnd a and gnd a' could be moved immediately adjacent the metallization terminations 404 and 404' such that a direct electrical connection is made to the via holes gnd a and gnd a'. In addition, ground vias gnd a and gnd a' could even comprise a single bump underneath the flat-thru capacitor 400 wherein a robotic dispenser could accurately place a BGA dots such that the ground electrical connection would be invisible beneath the flat-thru capacitor 400. Those skilled in the art will appreciate that there are many possible ways to make the electrical connections to the flat-thru capacitor 400. BGA dots can alternatively be solder bumps or dots of a conductive thermal-setting adhesive.

FIG. 28 is a sectional view taken from section 28-28 of prior art FIG. 27. The embodiment of FIG. 28 illustrates terminal pin 18a passing through the insulator 28 of an AIMD hermetically sealed feedthrough 14 and a via of an EMI filter circuit board 106' and electrically connected to the flat-thru capacitor 400 left-hand side active metallization termination 402. Terminal pin 18a must be discontinuous of terminal pin 18a' because, for the flat-thru capacitor 400 to function such that unwanted high frequency electrical interference is effectively diverted, the circuit current $i_1$, 410 must pass right through the electrode plates of the flat-thru capacitor 400. Accordingly, on the right-hand side of the flat-thru capacitor 400, the active metallization termination 406 is electrically connected to terminal pin 18a'. As previously discussed, terminal pin 18a could be disposed in an EMI filter circuit board 106' via hole 109. So as one traces the circuit current $i_1$, 410, from the body fluid side, one will appreciate that the circuit current $i_1$, 410, if it is a low frequency or DC current, low frequency meaning low frequency biologic signals, or low frequency therapeutic pacing pulses, such as cardiac pacing pulses, would pass from the body fluid side or from the device side from terminal pin 18a through the active electrode plates 412 of the flat-thru capacitor 400 and in turn, to the device side terminal pin 18a' as $i_1$, 410'.

Further regarding the embodiment of FIG. 28, the terminal pin connectors 16 on the device side of the embodiment illustrated in FIG. 28 are attached to circuit board lands on an AIMD active electronic circuit board 106 (not shown). If therapeutic low frequency pulses flow through the circuitry of the AIMD active electronic circuit board 106 with the intention of travelling to the distal electrodes in contact with human tissue, then the therapeutic pacing pulses would come from the device side of the AIMD into terminal pin 18a' and would then flow through flat-thru capacitor 400 unattenuated, and then flow out through terminal pin 18a on the body fluid side of the AIMD, through the leads (not shown) connected on the body fluid side of the AIMD, to the distal electrodes of the leads thereby stimulating a body tissue, for example, the myocardium of a heart. On the other hand, if terminal pin 18a was intended for sensing low frequency biologic signals, such low frequency biological signals sensed by a distal electrode of a lead enters terminal pin 18a on the body fluid side, then passes through the flat-thru capacitor 400 unattenuated or minimally attenuated, and then desirably flows to terminal pin 18a' to a circuit board circuit trace of the AIMD active electronic circuit board 106 (not shown). The sense signal would be assessed, and stimulation therapy appropriately adjusted such that the adjusted therapeutic low frequency pulses can flow through the circuitry of the AIMD active electronic circuit board 106, travelling the original therapy delivery path disclosed above.

There is a third type of signal that is very important and that is a high frequency dangerous EMI signal. If that signal is picked up by the body fluid side leads and distal electrodes, the undesirable EMI current would enter into terminal pin 18a, on the body fluid side and then would pass through the active electrode plates 412 of the flat-thru capacitor 400. Ideally, the flat-thru capacitor would divert (or capacitively decouple) this dangerous high frequency EMI energy through the capacitive reactance of the flat-thru capacitor 400 to the ferrule 26 and then, in turn, to the AIMD casing 32, which acts as a Faraday cage. In this way, the flat-thru capacitor 400 allows low frequency pacing and biological sensing signals to freely pass, while attenuating or filtering dangerous high frequency EMI.

FIG. 29 illustrates a different embodiment of a prior art flat-thru capacitor 400' comprising four poles, which is known as a quad polar flat-thru capacitor. Flat-thru capacitors can have any number of poles in various geometric configurations.

FIG. 30 is taken along lines 30-30 of the flat-thru capacitor 400' of FIG. 29, illustrating four active electrode plates 412a through 412d.

FIG. 31 is taken along lines 31-31 of the flat-thru capacitor 400' of FIG. 29, illustrating a ground electrode plate 414.

Accordingly, there is a need for high-voltage insulating materials, arrangements and assemblies that increase dielectric breakdown voltage in active medical implantable devices and electronic instruments. The present invention fulfills these needs and provides other related advantages.

Definitions

An "active implantable medical device (AIMD)" is defined herein as a special type of implantable medical device that implanted within a human body and includes electronic circuits, an energy source such as a primary or secondary battery; an energy induced by motion, thermal or chemical effects; or energy through external induction.

Regarding implantable medical devices, the term "active" means that the implantable medical device has at least one electronic circuit and an energy source, such as a primary battery, a secondary battery, a wireless energy source or a connected energy source.

Regarding electrical connections, the term "active" refers to an electrically active conductive pathway as opposed to a system grounded connection. The electrically active conductive pathway extends through an AIMD feedthrough insulator to the feedthrough insulator body fluid and device sides in insulative relationship with either the ferrule or the housing of the AIMD. Active conductive pathways may conduct therapeutic pacing pulses, biological sensing signals or even high-voltage therapeutic shocks. For a neurostimulator application, such as, but not limited to, a spinal cord stimulator, electrically active conductive pathways may conduct, for example, AC, pulse, or triangular waveforms, in addition to many other different types of waveforms. The electrically active conductive pathway includes any of the solid and fused solid electrical conductors listed in the above definitions.

The term "active circuit boards" is defined as AIMD active electronic circuit boards, which require a power source and have one or more electronic components, including capacitors, microchips and the like. The term "active" as used herein further applies to "active terminal pins" or "active co-sintered conductive vias", which constitute conductive pathways that pass through the hermetic terminal insulator to circuits that are "active circuits". In this context, "active" is defined as a terminal pin or circuit or implanted therapy delivery leadwire that conducts therapeutic pacing pulses and/or senses biological signals. In general, active circuits require a power source such as a primary or secondary battery. This is in contrast to ground terminal pins or ground circuit traces, which are generally at the potential of an AIMD casing.

As used throughout herein, an AIMD circuit board is defined as a circuit board enclosed within the casing of a hermetically sealed AIMD. The AIMD circuit board contains active electronic circuits, including, in most cases, a microprocessor among other components. An AIMD has either a primary battery or a secondary (rechargeable) battery that supplies electric energy to the circuit(s) of the circuit board, the circuit board electronics, or another source of energy, such as an energy harvesting mechanism from body motions, thermal energy, externally induced ultrasonic energy and the like. Thus, the AIMD circuit board is active and not passive, as passive circuit boards only contain passive electronic components.

An AIMD active electronic circuit board differs from an EMI filter circuit board in that AIMD active electronic circuit boards have at least one active electronic component. The EMI filter circuit boards of the present application are generally passive, and may contain MLCCs, X2Y attenuator capacitors or flat-thru capacitors. The EMI filter circuit boards disclosed herein are generally positioned on, near, adjacent or slightly away from the hermetic seal of the AIMD Similarly to AIMD active electronic circuits boards, EMI filter circuit boards may be permanently or removably affixed to AIMD feedthrough assemblies.

The term "implantable lead" refers to an electrically conductive structure having a distal electrode, a proximal terminal that connects to an implantable device, and a lead body that connects therebetween. The lead body consists of a flexible insulating tube or cylinder with at least one longitudinal lumen through which at least one implantable lead electrical conductor extends from the proximal terminal to the distal electrode. The at least one "implantable lead electrical conductor" allows the electric current to flow.

The term "conductive pathway" is defined herein as a conduction path for electrical current flow. The conductive pathway is an electrical conductor consisting of a lead, a wire, a leadwire, a terminal pin, a pin, a circuit trace, an electrical circuit, a fired electrically conductive structure, a co-fired electrically conductive structure, a paste filled via, a sintered filled via, a sintered paste filled via, a sintered electrically conductive material, a co-sintered filled via, a co-sintered paste filled via, a conductive co-sintered filled via, a composite conductive sintered paste filled via, or combinations thereof. Conductive pathways are typically hermetically sealed to a ceramic body by a brazing process, a co-firing process or a co-sintering process.

The terms "lead", "wire", "leadwire", "terminal pin", and "pin", as further defined herein, are electrical conductors having 100% density: in other words, solid electrical conductors. While each of the above may have unique structural features, they are all solid electrical conductors, each of which may be used alternatively to each other or in combination with each other, in any application requiring one or more conductive pathways, for example, but not limited to, a feedthrough for an implantable medical device. As such, the terms "lead", "wire", "leadwire", "terminal pin", and "pin", all being solid electrical conductors, are used interchangeably throughout this specification. It is understood that any number of the above named solid electrical conductors, in any combination, may be used in an application. Additionally, it is noted that the above solid electrical conductors are typically hermetically sealed to a ceramic body by either a brazing process or a co-firing process.

The terms "paste filled via", "sintered filled via", "sintered paste filled via", "sintered electrically conductive material", "co-sintered filled via", "co-sintered paste filled via", "conductive co-sintered filled via", and "conductive composite sintered paste filled via" as further defined herein, are all electrically conductive pathways formed using a co-sinter process. The fill material of the co-sintered filled via of the present application comprises an electrically conductive flowable medium selected from the group of a powder, an ink, a paste, a gel or an otherwise electrically conductive sinterable material. During the co-sintering process, particles of the flowable medium densify and fuse without melting to the point of liquefaction (i.e., becoming a liquid) to form an electrical conductor having density<100%, in other words, a fused solid electrical conductor. While each of the above may have unique formulations, after co-sintering, they are all fused solid electrical conductors, each of which may be used alternatively to each other or in combination with each other, in any application requiring one or more conductive pathways, for example, but not limited to, a feedthrough for an implantable medical device. As such, the terms "paste filled via", "sintered filled via", "sintered paste filled via", "sintered electrically conductive material", "co-sintered filled via", "co-sintered paste filled via", "conductive co-sintered filled via", and "conductive composite sintered paste filled via", all being fused solid electrical conductors, are used interchangeably throughout this specification. It is understood that any number of the above named fused solid electrical conductors, in any combination, may be used in an application. Additionally, it is noted that the above fused solid electrical conductors are typically hermetically sealed to a ceramic body by a co-sintering process.

Regarding the term "conductive pathways", it is anticipated that solid electrical conductors and fused solid electrical conductors may be used in combination and in any numbers with each other for an application. For example, when both solid electrical conductors and fused solid electrical conductors are formed in a single ceramic body, the forming process includes co-firing the solid electrical conductors while at the same time co-sintering the conductive flowable medium to form a ceramic body comprising conductive paths, wherein at least of the conductive paths is a solid electrical conductor, or at least one of the conductive paths is a fused solid electrical conductor. It is also anticipated that a solid electrical conductor and a fused solid electrical conductor may be integrated, which is herein defined as "a hybrid conductive pathway". Hybrid conductive pathways are formed by a co-firing process, whereby the conductive flowable medium sinters during the co-firing process thereby capturing a solid electrical conductor in, on or adjacent the resultant fused solid electrical conductor.

A feedthrough conductive co-sintered filled via passes through a feedthrough insulator. When the feedthrough insulator is hermetically sealed to a ferrule or a housing, the conductive co-sintered filled via of the feedthrough insulator is in nonconductive relation with a feedthrough ferrule or housing. The conductive co-sintered filled via electrically acts in the same manner as the previously disclosed solid electrical conductors. The conductive co-sintered filled via may optionally incorporate a co-fired component, such as, but not limited to, a wire, lead, pin, ribbon, screw, connector, nail head or a custom designed attachment structure.

The term "brazing process" is defined as a hermetic sealing process by which a solid electrical conductor is hermetically sealed to a ceramic body by means of a braze material.

The term "braze material" is defined herein as a metal or alloy in the form of a wire or a braze preform of compressed nanoparticles having a lower melting temperature than either of the parts to be sealed. Upon melting, the braze material metallurgically wets the surface of each part. Upon cooling, the braze solidifies to form a hermetic seal therebetween. The braze material may be selected from the group gold, gold-containing alloys, platinum, platinum-containing alloys, palladium, palladium-containing alloys, iridium, iridium-containing alloys, germanium, germanium-containing alloys and combinations thereof.

The term "co-fire process" is defined as a hermetic sealing process by which an entire ceramic body and any solid electrical conductors are fired at the same time in order to form a monolithic structure comprising at least one hermetically sealed electrically conductive pathway adhered directly to the ceramic body.

The term "co-sinter process" is defined as a hermetic sealing process by which a green ceramic body and an electrically conducting flowable medium are sintered at the same time to form a monolithic structure comprising at least one hermetically sealed co-sintered conductive pathway adhered directly to the ceramic body.

The term "ceramic reinforced metal composite (CRMC)" is defined herein as a composition composite comprising a metal matrix composite and a ceramic matrix composite.

The term "feedthrough conductive pathway" is defined herein as an electrical conductor through which current flows extending to a feedthrough insulator body fluid side and a feedthrough insulator device side. The feedthrough conductive pathway may be selected from a lead, a wire, a leadwire, a terminal pin, a pin, a sintered electrically conductive material or combinations thereof. The feedthrough conductive pathway may be formed by one of a brazing process, a co-fire process, or a co-sinter process. For medical implantable devices, a feedthrough conductive pathway must be hermetic.

The term "hermetic" is defined herein as impermeable, that is, keeping gases, liquids, and solids from penetrating and/or permeating into or out of a sealed structure, device or system. Hermeticity is specifically a requirement when the performance and reliability of sensitive electrical and optical components can be compromised by a leaking seal. For example, it is well known that hermeticity is specifically required for implantable devices, such as, but not limited to, AIMDs, implantable sensors, implantable recorders, implantable monitors, leadless implantable devices, implantable bions, among others, because even very small amounts of a gas, a liquid or a solid (e.g., moisture, harmful gases, water vapor, chemicals, salts) within the housing of such devices have been shown to compromise electronics and photonics. Historically, therefore, to be considered "hermetic", the maximum internal moisture content allowed inside a hermetic package has been 5000 PPM or 0.5% water vapor. The rationale being that, at 5000 PPM, the water vapor dew point is well below the water vapor freezing point, therefore any moisture that would condense inside the package would be in the form of ice crystals and not be available for corrosion processes. Also, at the time the moisture limit was originally set, 5000 PPM represented the minimum repeatable detection limits of the then available equipment. However, it is now understood that, even at relatively dry moisture levels, condensation can and will form inside an enclosed hermetic package at a temperature of around 5° C. It is also known that materials internal of an enclosed hermetic package, particularly polymeric materials and plastics, outgas moisture over time. Additionally, it has been demonstrated that implantable devices having even very small amounts of water vapor inside a sealed housing causes harm to the sensitive electronics and photonics enclosed therewithin. In fact, the effects of moisture levels$\geq$8000 PPM include not only corrosion, which causes damage to metal interconnects, but also electrical leakage across conductors, such as leads, wires, pins, traces, and connectors, among others; electrical shorts due to dendritic growth of electrically conductive materials: and light scattering or wavelength drift in photonic components. Additionally, analysis of devices that exhibit hermetic leaks have demonstrated that the leak can be severe, and, in some cases, not only cause component failure, but also complete device failure. Complete device failure can be catastrophic for a patient. For a pacemaker-dependent patient, complete device failure is immediately life-threatening, as the patient's heart does not beat unless the pacemaker stimulates the patient's heart to do so.

Regarding the term "hermetic", it is noted that for hermetic seals using polymeric materials and plastics, a helium leak test method cannot provide reliable leak test results, as the helium leak test method only measures leakage and does not measure permeation. More specifically, the helium leak test method only exposes polymeric and plastic seals to helium for only a short period of time, therefore the helium leak test method does not and cannot account for the high permeation rates over time. In other words, polymeric material and plastic seals may test to be "helium-tight" but will not sustain being "helium-tight" over time, as their inherently high permeation and absorbent nature can result in moisture levels catastrophic to enclosed sensitive electronics and photonics unpredictably in a matter of a few days, several weeks, or even after being implanted in a patient. It is noted that Military and Space standards prohibit the use of a polymeric "adjunct sealant" over a hermetic seal as it may mask the true leak rate.

The term "feedthrough insulator" is defined as an electrically insulating body having at least one via for an electrical conductor. The feedthrough insulator may comprise one of a ceramic, a glass, a glass-ceramic or combinations thereof.

As used herein, a "hermetic seal feedthrough insulator" is defined as an electrically insulating body having at least one hermetically sealed conductive pathway. A hermetic seal feedthrough insulator may comprise one of a sintered ceramic, a fused glass, a fused glass-ceramic, or combinations thereof. The hermetic seal feedthrough insulator can be a standalone component to be disposed on a ferrule surface, in a ferrule opening, or in a device housing opening, or the hermetic seal feedthrough insulator can be formed as an assembly with the ferrule or the housing.

As used herein, a "hermetically sealed feedthrough" is defined as a hermetic terminal that is attachable to an AIMD, wherein, when the hermetic terminal is attached to an opening in a housing of an AIMD, the hermetic terminal body fluid side and the hermetic terminal device side reside outside and inside the AIMD, respectively. A "feedthrough hermetic terminal" provides for an electrical connection between the hermetically sealed feedthrough body fluid and the device sides through at least one conductive pathway disposed therethrough. For example, the conductive pathway of a hermetically sealed feedthrough provides for an electrical connection between the electrical circuits within a hermetically sealed device housing and a connector block assembly to which at least one implantable lead is connectable.

The term "hermetically sealed filtered feedthrough" is defined as a hermetic feedthrough to which an EMI filter is mounted either directly to the feedthrough or indirectly to the feedthrough by way of a filter circuit board. The hermetically sealed filtered feedthrough is attachable to an AIMD, wherein, when the hermetically sealed filtered feedthrough is attached to an opening in a housing of an AIMD, the hermetically sealed filtered feedthrough body fluid side and the hermetically sealed filtered feedthrough device side reside outside and inside the AIMD, respectively.

An "EMI filter" is defined herein as a passive component that filters electromagnetic interference (EMI). The EMI filter comprises at least one active electrode plate disposed parallel and spaced from at least one ground electrode plate. The active and ground electrode plates are further disposed on or within a dielectric material. The terms "EMI filter", "EMI filter capacitor", "filter" and "filter capacitor" are used interchangeably throughout this specification.

The "EMI filter" is further defined herein as a first capacitor that is electrically connected between a hermetically sealed active conductive pathway of a hermetically sealed filtered feedthrough and a hermetically sealed implantable device housing. The EMI filter may be a three-terminal capacitor (such as a feedthrough filter capacitor or a flat-thru filter capacitor) or a two-terminal capacitor (such as an MLCC filter capacitor or an X2Y attenuator filter capacitor). Ideally, the role of the EMI filter is to freely pass low frequency biologic signals without significant attenuation, such as therapeutic pacing pulses, while, at the same time, diverting dangerous high-frequency EMI energy to the equipotential surface of the implantable device housing such as the AIMD housing. The equipotential surface of the AIMD housing acts as a Faraday cage shield, which is defined herein as system ground. It is noted that when a ferrule structure is laser welded to an opening in an AIMD housing, the ferrule structure then is part of the system ground. When undesirable EMI energy is diverted to the system ground, the undesirable energy is dissipated harmlessly as a few milliwatts of heat energy. In the specific case of magnetic resonance imaging (MRI), even watts of heat energy, which can be induced by the MRI scanner environment, are dissipated harmlessly into surrounding body tissues such as a pectoral pocket. In this manner, the dangerous EMI energy is prevented from entering the hermetically sealed AlMD, where the EMI can reach sensitive AIMD circuitry, and can thereby seriously disrupt the proper operation of the AIMD. An EMI filter may be selected from the group: a feedthrough capacitor, an MLCC filter capacitor, an X2Y attenuator filter capacitor, a flat-thru filter capacitor, a stacked film filter capacitor, a tantalum filter capacitor, an EMI filter circuit board, and combinations thereof, which are disposed on, near or adjacent the implantable device hermetically sealed feedthrough, for example, an AIMD hermetically sealed feedthrough. The EMI filter circuit board may further comprise one or more feedthrough capacitors, MLCC capacitors, X2Y attenuator capacitors, flat-thru capacitors, stacked film capacitors, or tantalum capacitors mounted on or within the EMI filter circuit board.

The term "system ground" is defined herein as an electrically conductive enclosed housing of an implantable medical device. The implantable medical device housing acts as an electromagnetic shield, a Faraday cage, and an energy dissipating surface. The system ground may also include an optional metallic electrically conductive feedthrough ferrule, which is mechanically and electrically attached to an opening in the implantable medical device housing; an optional pocket pad, which is formed on a ferrule or a housing; or an optional metal addition, which is electrically connected to a ferrule or a housing. Many AIMDs are hermetically sealed in a titanium housing, which is both electrically conductive and biocompatible. The titanium housing acts as an electromagnetic shield. Some AIMDs have a ceramic hermetically sealed housing, which is an insulator. In order to provide a system ground in EMI shielding, they are generally coated on the inside with a conductive layer of metal, such as nickel or the like. Since this layer of metal is not exposed to body fluid, it does not have to be biocompatible or bioinert, such as titanium. In this case, if there was an EMI filter, then the coating on the inside of the ceramic housing would become the Faraday cage or EMI filter system ground.

An "insulator" is defined herein as a material that acts as a barrier to the flow of electrons. The atoms of the insulator are strongly bonded together, which obstructs the flow of electrons. In other words, insulators are materials that do not conduct electricity in an electric field, as they do not have free electrons to do so. Throughout this specification, the term "insulator" applies to an implantable device feedthrough insulator.

A "dielectric material" is defined herein as a material that stores electrical energy in an electric field. The molecules of a dielectric material are weakly bonded; hence, a dielectric material polarizes in the presence of an electric field. Polarization is a material property in which positive and negative charges move in the opposite direction. In other words, a dielectric material polarizes so that the negative charges in the dielectric material orient themselves toward a positive electrode and the positive charges in the dielectric material shift toward a negative electrode. The more easily a material is polarized, then the greater is the amount of charge that can be stored. Throughout this specification, the term "dielectric" applies to an implantable device EMI filter substrate. Insulators, as defined and used throughout this specification do have a low dielectric constant but are not herein considered "dielectric materials".

A "dielectric constant k" refers to the ability to store energy in an electric field. A material's degree of polarization is related to the dielectric constant k and the electric field strength. That being said, all dielectrics are insulators as dielectrics have high electrical resistance without an electric field but polarize in the presence of an electric filed. All insulators, on the other hand, will not be a dielectric, as the tightly bound atoms of the insulator do not allow the electrons to freely flow atom to atom (will not conduct electricity). The dielectric constant of the filter capacitors of the present invention range from >0 to 200, from >0 to 1000 and >1000 k.

The term "pocket pad" is defined as one or more cavities formed on or within a ferrule. The cavities may comprise one of a pocket, a pad, a trough, a slit, or a custom orifice. Throughout the present specification, the term "loaded pocket pads" are often referred to as "gold pocket pads"; it is understood, however, that the term "gold pocket pads" is not meant to be limiting to gold, but instead is inclusive of all of the loading material options as defined above. One or more pocket pads are each loaded with a preform (i.e., an oxide-resistant material, for example, but not limited to, gold), and the preform is reflowed at a temperature above the preform material melting point. The preform may be a substantially pure gold solid material, pressed gold powder, an alloy of at least 50% gold, pressed gold nanoparticle powder, or coiled fine gold wire. The preform may also be of platinum, palladium, and any alloys thereof in the forms disclosed for gold. The preform may be any material that can be metallurgically bonded to an oxidizable surface, such as, but not limited to, titanium. The term "metallurgical bonded" includes existing oxide burn-through and/or penetration. The end result is a substantially oxide-resistant electrical connection. It is noted that the pocket pad is an essential structure, as a pocket creates a containment cavity (like a swimming pool) such that the preform material will not undesirably flow away, outflow, seep or bleed to other areas or surfaces, thereby by serving as an oxide-resistant attachment pad. As such, the pocket can be configured to be relatively thin in contrast to prior art structures. In an embodiment, the thickness of the gold pocket preform may be 1 mil thick (0.001 inch). In an embodiment the gold pocket preform may be on the order of 5 to 10 mils thick (0.005 to 0.010 inch) to facilitate preform handling, including robotic placement of the preform into the pocket.

The term "oxide-resistant" is defined as the ability to resist surface reactions that increase connection electrical resistance, introduce unstable connection resistance change, or disrupts electrical connection conductivity. Oxide-resistant materials include platinum, palladium, gold, rhodium, and their alloys. An oxide-resistant pocket-pad or metal addition may comprise an oxide-resistant material selected from the group consisting of gold, gold alloys, rhodium, rhodium alloys, platinum, platinum alloys, platinum-iridium alloys, palladium, palladium alloys, nitinol, titanium nitride, cobalt-chromium alloys, and combinations thereof.

The term "electrical connection pad" is defined as a small surface of metal, such as copper or other suitable electrically conductive material, on or within a circuit board or, alternatively, somewhere on the perimeter edge of the thickness of a printed circuit board that allows attaching a component to the circuit board. An electrical connection pad may comprise a circuit board land, be part of a circuit trace or be part of the perimeter edge of the thickness of a circuit board in addition to being on the surface of the circuit board as shown. An edge metallization may either be an electrical connection pad that is part of the metallization structure, or discontinuous from the edge metallization. Also, —a perimeter edge may comprise an electrical connection pad, the perimeter edge not necessarily requiring an edge metallization.

It is understood to those skilled in the art that the terms AIMD "casing", "housing" and "can" are synonymous. As used throughout this specification, the terms "casing", "housing" and "can" can be applied to the overall AIMD hermetically sealed enclosure 32, which may have can halves 112, 114, or a lid (not shown), and which is generally conductive and forms an electromagnetic shield (Faraday cage). This is not to be confused with the housing 66 of the terminal pin connector 16 of the present invention. Hence, the use of similar terms "casing", "housing" and "can" must be taken in context with the structures to which these terms refer.

The term "voltage standoff" is understood to mean a minimum dielectric strength or breakdown voltage, whereby avalanche breakdown, microcoulomb discharge, flashover or arc-over will not occur between active and system ground or between active pins.

The term "active-to-system ground standoff distance" is defined herein as the distance between an active terminal electrical conductor and the system ground.

The term "dielectric breakdown strength (DBS)" is defined as the maximum electrical potential that a material can resist before electrical current breaks through the material and the material is no longer an insulator. As such, the dielectric breakdown strength of one or more filter capacitor insulating materials is further increased by adding very small insulating particles such as, but not limited to, metal oxides, and in particular, nano-scale metal oxide insulating powders, to the insulating material. Example insulating materials include elastomers, polymers, or plastics. The insulating materials may be an epoxy, a liquid silicone rubber, a polycarbonate, a polyester, a polyether, a polyurethane, a polyimide, or a polyamide. Nano-scale metal oxides may be selected from one of: alumina, baria, calcia, ceria, magnesia, silica, strontia, titania, and zirconia ceramic families. Non-limiting examples of some nano-scale metal oxides that can be used include: $Al_2O_3$, $BaO$, $CaO$, $CeO_2$, $MgO$, $ZrO_2$, $SiO_2$, $TiO_2$, $Al_2SiO_{53}$, $BaTiO_3$, $SrTiO_2$, and combinations thereof. Various stabilized or partially stabilized zirconia may be used including zirconia toughened alumina (ZTA) and alumina toughened zirconia (ATZ), Yttrium stabilized zirconia (YSZ), yttrium-toughened zirconia (YTZP), and combinations thereof. Additionally, some nitrides may also be used, such as, AlN, $Si_3N_4$, BN, and combinations thereof.

With respect to a "by weight" perspective, nanoparticle loading in the insulating material ranges from >0% to ≤90%, by weight, preferably from >0% to about 40%, by weight. With respect to a "by volume" perspective, nanoparticle loading in the polymeric insulating material ranges from >0% to ≤99%, by volume, more preferably from >0% to ≤30%, by volume.

The term "dielectric breakdown strength (DBS)" also refers to a level of insulation, wherein flashover, avalanche discharge, carbon tracking or catastrophic failure or microcoulomb discharge does not occur during high-voltage testing.

The term "nano" is defined as an insulating particle size measured in nanometers or microns. The term "nano" is broadly used herein to describe microscopic particles that are not visible to the naked eye.

The term "nanoparticle" refers to "nano-size to micron-size" insulating microscopic particles that are specifically added to an implantable medical device polymeric or plastic insulator or an insulating material in order to increase the dielectric breakdown strength (DBS) of the polymeric or plastic insulator or insulating material. Increasingly, the DBS of polymeric and plastic insulators and insulating materials translates into an increased standoff voltage, which is particularly important for high-voltage applications. By increasing the standoff voltage between an active electrical conductor and system ground, microcoulomb discharge, avalanche breakdown, flashover and/or arc-over will not occur. Increasing the DBS of the polymeric and plastic insulators does not in and of itself prevent surface flashover between conductors of opposite high-voltage polarity that are too close to each other. Accordingly, increases in dielectric breakdown strength assume that there is sufficient physical distance between conductors of opposite high-voltage polarity across the surfaces of such insulators, so that a surface flashover does not occur.

Generally regarding the term "nanoparticle", the smaller the insulating nanoparticles, the higher the increase in insulator DBS (assuming a sufficient quantity of insulating nanoparticles and uniform distribution of these nanoparticles throughout the polymeric or plastic insulators or insulating materials). The insulating nanoparticles of the present invention range in size from 1 nm (0.001 μm) to 40,000 nm (40 μm). An insulating nanoparticle size range for a polymeric or plastic insulator or insulating material can be determined by the maximum voltage of the application.

The terms "nano-dielectrics", "nano-dielectric additives", "nano-insulating materials" and "nano-insulating additives" all refer to insulating nanoparticles and are used interchangeably with the term "nanoparticles". "Insulating nanoparticles" are essentially filler materials that may be configured as particulates, short fibers, long fibers, spheres, flakes, submicron fibers, which are isotropically dispersed within the base polymeric material.

The term "thermoplastic" refers to any plastic or polymeric material that becomes pliable or moldable at a certain elevated temperature and solidifies on cooling. Thermoplastic plastic or polymeric materials may be transformed into thermosetting plastic and polymeric materials by free radical cross linking using techniques, such as, but not limited to, redox initiators or high energy radiation.

The term "thermosetting" refers to any plastic or polymeric materials that forms irreversible chemical bond during the curing process, thus do not melt when heated. Composite or hybrid thermoplastic/thermosetting polymeric insulating components may be made by coating either a homogeneous thermoplastic material or a thermosetting material with a thermoplastic plastic or polymer. The thermoplastic material coating can be used to bond AIMD components, such as an EMI filter and a feedthrough insulator, or may alternatively be used to increase electrical stand-off distance and/or electrical breakdown strength of AIMD electrical components.

As used to herein, all compositional percentages are by weight or by volume of the total composition, unless otherwise specified.

As used herein, the word "include," and its variants, is intended to be non-limiting, such that recitation of items in a list is not to the exclusion of other like items that may also be useful in the materials, compositions, devices, and methods of this technology.

Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The term "adjacent" means adjoining a structure, attached to a structure, or near a structure. As used herein, the term "adjacent" is not limited to touching. The term "adjacent" includes being near a structure, being mounted directly onto a structure, being spaced from a structure, for example, by an air gap or by a spacer, such as a washer or an adhesive between two structures.

SUMMARY OF THE INVENTION

The present invention relates to a circuit board connector assembly that comprises a circuit board having at least one electrical circuit and a terminal pin connector having a connector housing comprising an alignment flange with an inner surface that tapers downwardly and inwardly from a proximal opening to an electrically conductive connector housing sidewall. The connector housing sidewall defines a housing opening extending along a longitudinal axis, and the connector housing is electrically connected to the at least one electrical circuit of the circuit board. At least one electrically conductive connector prong is supported by and angled from the connector housing sidewall toward the longitudinal axis of the housing opening. Further, an insulative material coats at least a portion of the sidewall of the connector housing.

The insulative material is selected from silicone, polyurethane, polyester, polyethylene, polypropylene, polyimide, polyamide, synthetic polyamide, acrylic, polyacrylates, perfluoroalkoxy (PFA), fluorinated ethylene-propylene (FEP), polyetheretherketone (PEEK), polyamide imide (PAI), polyphenylsulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), and combinations thereof.

Nanoparticles selected from $Al_2O_3$, BaO, CaO, $CeO_2$, MgO, $ZrO_2$, $SiO_2$, $TiO_2$, $Al_2SiO_{53}$, $BaTiO_3$, $SrTiO_2$, ZnO, $Si_3N_4$, zirconia toughened alumina (ZTA), alumina toughened zirconia (ATZ), Yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof are provided in the insulative material to increase its dielectric breakdown strength (DBS). The nanoparticles range in size from greater than about 100 nanometers (0.1 microns) to about 40,000 nanometers (40 microns) and have a loading in the polymeric insulating material ranges from >0% to about 40%, by weight.

To aid in mounting the connector housing to the circuit board, the sidewall of the connector housing has at least one planar surface. If desired, the connector housing has an outwardly extending alignment flange that help align the connector housing adjacent to an edge of the circuit board.

The present invention is also related to an active implantable medical device (AIMD) comprising an AIMD housing and a circuit board having at least one electrical circuit is contained inside the AIMD housing. A terminal pin connector is also located inside the AIMD housing. The connector housing has an alignment flange with an inner surface that tapers downwardly and inwardly from a proximal opening to an electrically conductive connector housing sidewall, which defines a housing opening extending along a longitudinal axis. The connector housing is electrically connected to the at least one electrical circuit of the circuit board. At least one electrically conductive connector prong is supported by and angled from the connector housing sidewall toward the longitudinal axis of the housing opening. Further, an insulative material coats at least a portion of the sidewall of the connector housing.

A feedthrough is also connected to the AIMD housing. The feedthrough has an electrically conductive ferrule with a ferrule opening. The ferrule is sealed in an opening in the AIMD housing. An insulator is hermetically sealed to the ferrule in the ferrule opening. The insulator has an insulator body fluid side opposite an insulator device side so that the insulator body fluid and device sides reside outside and inside the AIMD housing, respectively. An electrically conductive terminal pin hermetically sealed to the insulator in an insulator passageway extends outwardly beyond the insulator device side. That way, the terminal pin connector is configured to allow multiple insertions and retractions of the feedthrough terminal pin into and out of the connector housing opening with the at least one connector prong angled toward the longitudinal axis being accordingly contacted to and uncontacted from the terminal pin of the feedthrough.

BRIEF DESCRIPTION OF THE DRAWINGS

FIGS. 4A-4C illustrate embodiments of the clip of the connector housing of the terminal pin connector.

FIG. 6A shows a proximal end view of an embodiment of the terminal pin connector.

FIG. 6B shows a cross-sectional view of the terminal pin connector of FIG. 6A taken along lines 6B-6B.

FIG. 6C shows a distal end view of the terminal pin connector of FIG. 6A.

FIG. 34 illustrates a syringe dispenser, which may alternatively be a robotic dispenser, a spray, or the like, for application of insulating materials. The insulating materials may comprise conventionally used insulating materials and/or the nanoparticle-filled polymeric insulating materials of the present invention.

FIG. 35A is an end view of an AIMD circuit board connector flange surface, illustrating a nanoparticle-filled insulating polymeric material disposed on the entire surface of the flange and the "no insulating material" symbols showing the locations that are not to be covered with insulating material.

FIG. 35B is a cross-sectional view of FIG. 35A illustrating locations where the nanoparticle-filled polymeric insulating material is desirably disposed and the locations where the nanoparticle-filled polymeric insulating material is not to be disposed.

FIG. 35C is similar to FIG. 35A illustrating the opposite end view of a circuit board connector surface, showing where the nanoparticle-filled polymeric insulating material is disposed and the "no insulating material" symbols showing where the nanoparticle-filled polymeric insulating material is not disposed.

FIGS. 36A, 36B and 36C are the same blown-up partial view of FIGS. 35A, 35B and 35C, except now the insulating material is a polymeric insulating material that is not filled with insulating nanoparticles.

DETAILED DESCRIPTION OF THE INVENTION

The inventions disclosed herein apply to all the component embodiments in the literature and prior art patents incorporated herein by their reference.

Figure 32A:
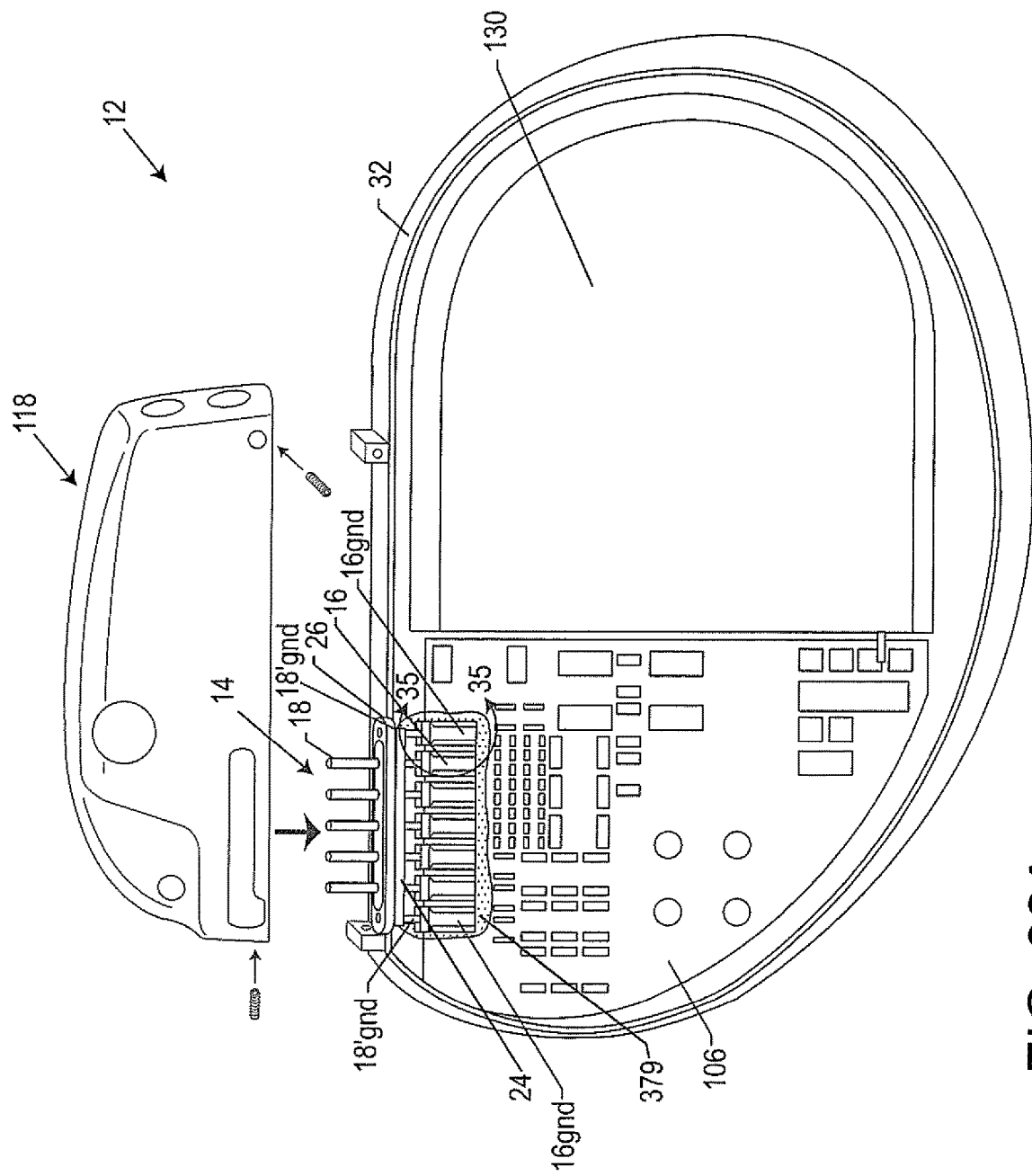
FIG. 32A is an exploded side view cutaway of the present invention applied to an implantable cardioverter defibrillator (ICD) pulse generator, illustrating the device side circuit board connectors electrically coated with the nanoparticle filled polymeric insulating material of the present invention.

FIG. 32A is a cutaway view of an AIMD 12, which, for example, can be an implantable cardioverter defibrillator (ICD) 12I, showing that the terminal pin connectors 16, 16gnd are covered with a novel nanoparticle-filled polymeric insulating material 379. The addition of insulating nanoparticles to a polymeric insulating material effectively increases the breakdown strength of that insulating material. As previously defined, "dielectric breakdown strength (DBS)" is the maximum electrical potential that a material can resist before electrical current breaks through the material and the material is no longer an insulator. Also, as previously defined, increased "dielectric breakdown strength (DBS)" refers to a level of insulation wherein flashover, avalanche discharge, carbon tracking, catastrophic failure or microcoulomb discharge does not occur during high-voltage testing. Depending on the voltage requirements of an application, and, in particular, for high-voltage applications, adding insulating nanoparticles to a polymeric insulating material can substantially increase or enhance the dielectric breakdown of a polymeric insulating material. Examples of polymeric insulating materials include, but are not limited to, elastomers, polymers, or plastics, including an epoxy, a liquid silicone rubber, a polycarbonate, a polyester, a polyether, a polyurethane, a polyimide, and a polyamide. Example of insulating nanoparticle materials include, but are not limited to, metal oxides, including alumina, baria, calcia, ceria, magnesia, silica, strontia, titania, and zirconia ceramic families. Non-limiting examples of some nano-scale metal oxides that can be used include: $Al_2O_3$, $BaO$, $CaO$, $CeO_2$, $MgO$, $ZrO_2$, $SiO_2$, $TiO_2$, $Al_2SiO_{53}$, $BaTiO_3$, $SrTiO_2$, and combinations thereof. Various stabilized or partially stabilized zirconia may be used including zirconia toughened alumina (ZTA) and alumina toughened zirconia (ATZ), Yttrium stabilized zirconia (YSZ), yttrium-toughened zirconia (YTZP), and combinations thereof. Additionally, some nitrides may also be used, such as, $AlN$, $Si_3N_4$, $BN$, and combinations thereof.

As previously disclosed, "nano" is broadly used herein to describe microscopic particles that are not visible to the naked or unaided human eye, having insulating particle sizes measured in nanometers or microns. Additionally, as used herein, "nanoparticle" refers to "nano-size to micron-size" insulating microscopic particles that are specifically added to a polymeric or plastic insulator or an insulating material of an implantable medical device in order to increase its dielectric breakdown strength (DBS). For a particular application, increasing the DBS of polymeric and plastic insulators and insulating materials translates into increased standoff voltage, which is particularly important for high-voltage applications. By increasing the standoff voltage between an active electrical conductor and system ground, microcoulomb discharge, avalanche breakdown, flashover and/or arc-over will not occur. It is noted, however, that increasing the DBS of polymeric and plastic insulators does not in and of itself prevent surface flashover between conductors of opposite high-voltage polarity that are too close to each other. Accordingly, increasing dielectric breakdown strength using polymeric or plastic insulators or insulating materials implies that a sufficient physical distance between conductors of opposite high-voltage polarity across the surfaces of such insulators exists, so that, working together, a DBS is achieved to prevent surface flashover from occurring.

In general, the smaller the nanoparticles, the higher the increase in insulator DBS (assuming a sufficient quantity of nanoparticles and uniform distribution of the nanoparticles throughout the polymeric or plastic insulators or insulating materials). The nanoparticles of the present invention range in size from 1 nm (0.001 μm) to 40,000 nm (40 μm). In an embodiment, the nanoparticles of the present invention range in size from 1 nm (0.001 μm) to 4000 nm (4 μm). A nanoparticle size range for a polymeric or plastic insulator or insulating material can be determined by the maximum voltage of the application.

As also previously presented, "nano-dielectrics", "nano-dielectric additives", "nano-insulating materials" and "nano-insulating additives" all refer to nanoparticles and are used interchangeably with the term "nanoparticles". "Insulating nanoparticles" are essentially filler materials that may be configured as particulates, short fibers, long fibers, spheres, flakes, submicron fibers, which are isotropically dispersed within the base polymeric material.

Illustrated in the embodiment of FIG. 32A are seven terminal pin connectors, five of which are active terminal pin connectors 16 and two are ground terminal pin connectors 16gnd. The active terminal pin connectors 16 reside between the ground terminal pin connectors 16gnd. Both ground terminal pins 18'gnd are directly electrically and mechanically connected to the feedthrough ferrule 26, either by a laser weld 160 or a gold braze 165 so both the terminal pins 18'gnd and the terminal pin connectors 16gnd are at the potential of the system ground 124. Terminal pin connectors 16, 16gnd are more thoroughly disclosed in U.S. Pat. No. 11,211,741 and U.S. Pub. No. 2022/0115806, the contents of which are fully incorporated herein by this reference.

Referring again to FIG. 32A, it is appreciated that any number of active and ground terminal pins are possible, depending on the AIMD and its configuration. In addition, the feedthrough capacitor 24 can be an internally grounded feedthrough capacitor or comprise MLCC chips on a circuit board, an X2Y attenuator or a flat-thru capacitor. It will also be appreciated that the AIMD shown in FIG. 32A can be any type of AIMD, including cardiac pacemakers, neurostimulators, and the like. In an ICD configuration, high-voltage pulses must be delivered to the heart and pass-through terminal pins 18. The high-voltage pulse is applied to defibrillation electrodes that are typically inside the heart and the defibrillation pulses can be oriented from pin to pin (18 to 18) or from any pin 18 to 18'gnd and in turn, the housing 112 (this is known as the "hot" can configuration). For an ICD application, it is particularly important that high-voltage insulation be provided between each of the circuit board connectors 16 and ground. It is also true that low-voltage devices, such as pacemakers and neurostimulators, can also be subjected to high-voltage insults. High-voltage insults can occur, for example, during handling where an electrostatic discharge may occur, or after implantation if the patient is exposed to an automatic external defibrillator (AED). An AED can couple energy to an implanted lead, which can result in a high-voltage pulse travelling down a leadwire 18 and into the interior of the active implantable medical device 12. In an ICD application, a high-voltage ICD pulse, as previously described, can create a voltage ring-up as it's charging the feedthrough capacitor, or any filtered capacitor 24, thereby causing the voltage to increase even further. For an ICD application, the nanoparticle-filled polymeric insulating material 379 becomes particularly important.

Figure 1:
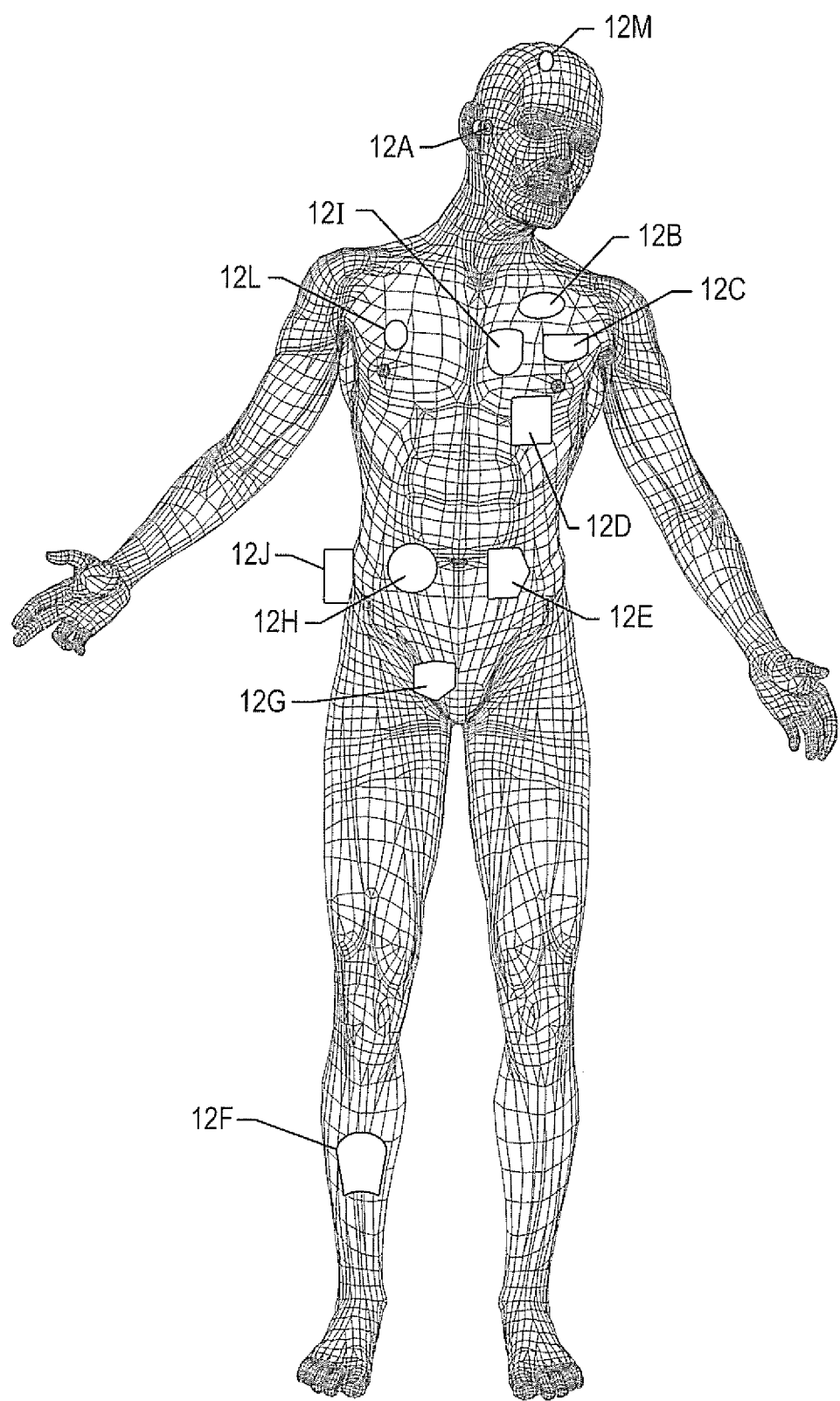
FIG. 1 is a wire-form diagram of a generic human body showing a number of exemplary implantable medical devices.
Figure 1A:
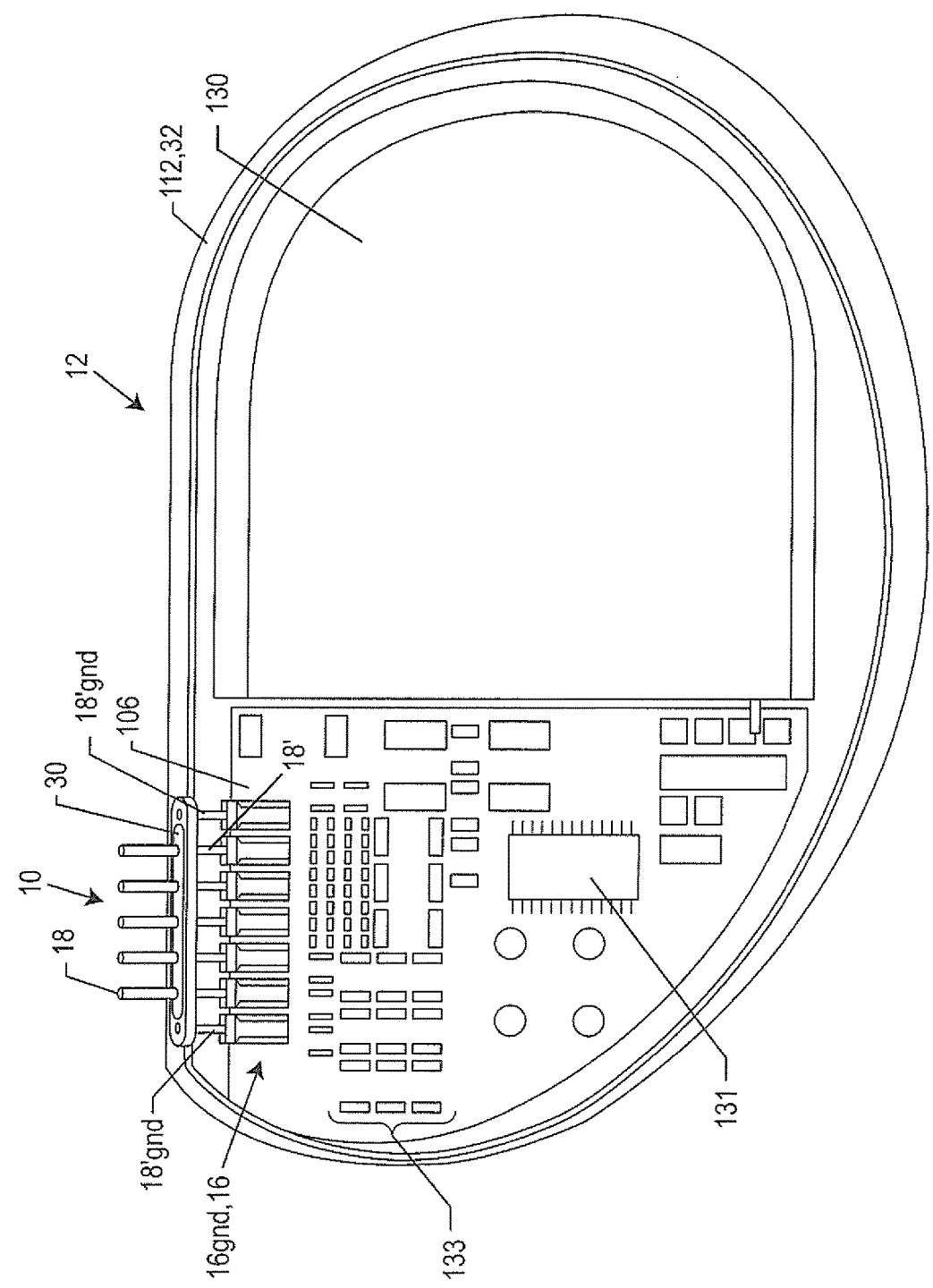
FIG. 1A illustrates a perspective view of an embodiment of an AIMD feedthrough connector assembly positioned within an AIMD casing half.
Figure 1B:
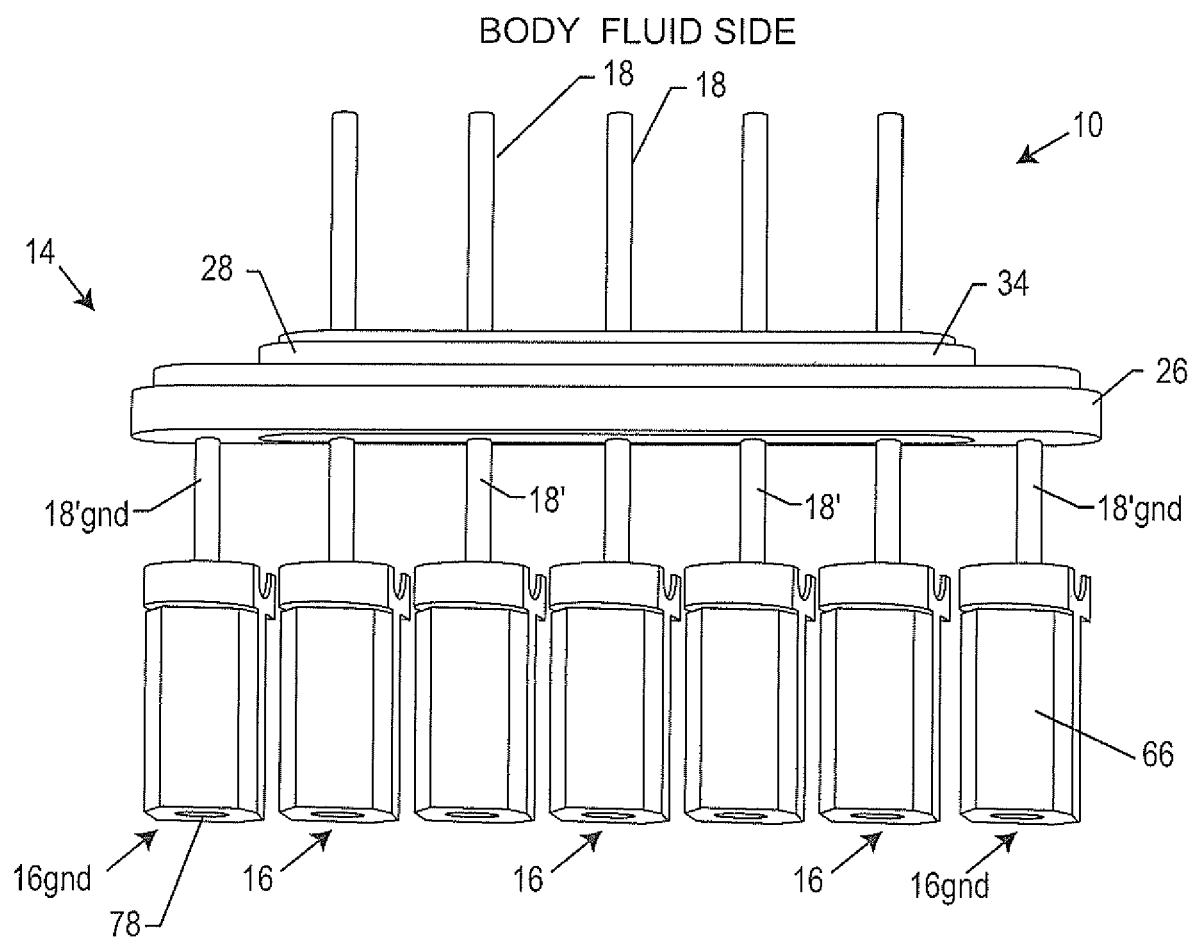
FIG. 1B illustrates a side perspective view of an embodiment of the AIMD feedthrough connector assembly.
Figure 2:
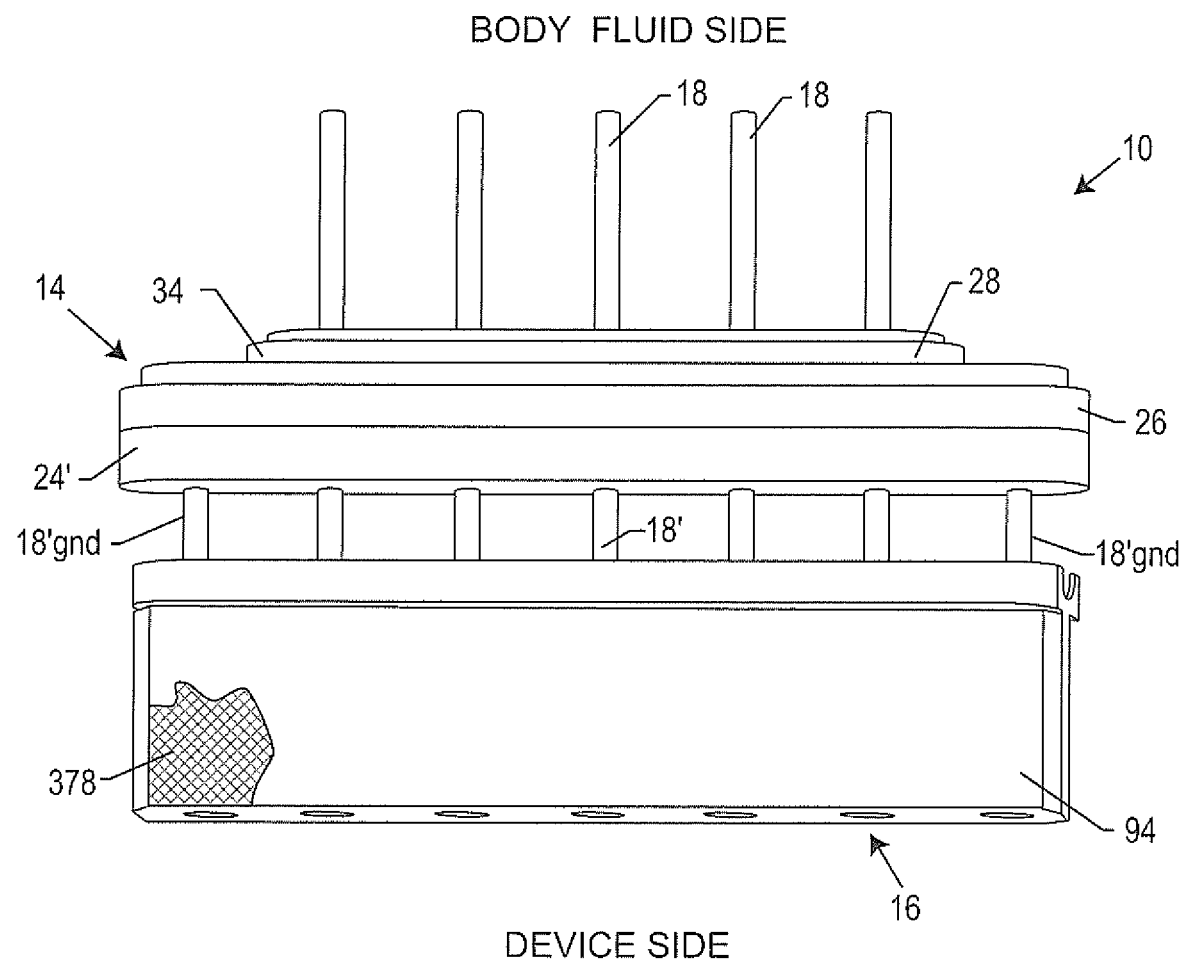
FIG. 2 illustrates an alternative embodiment of the AIMD feedthrough connector assembly comprising a one-piece housing.
Figure 3A:
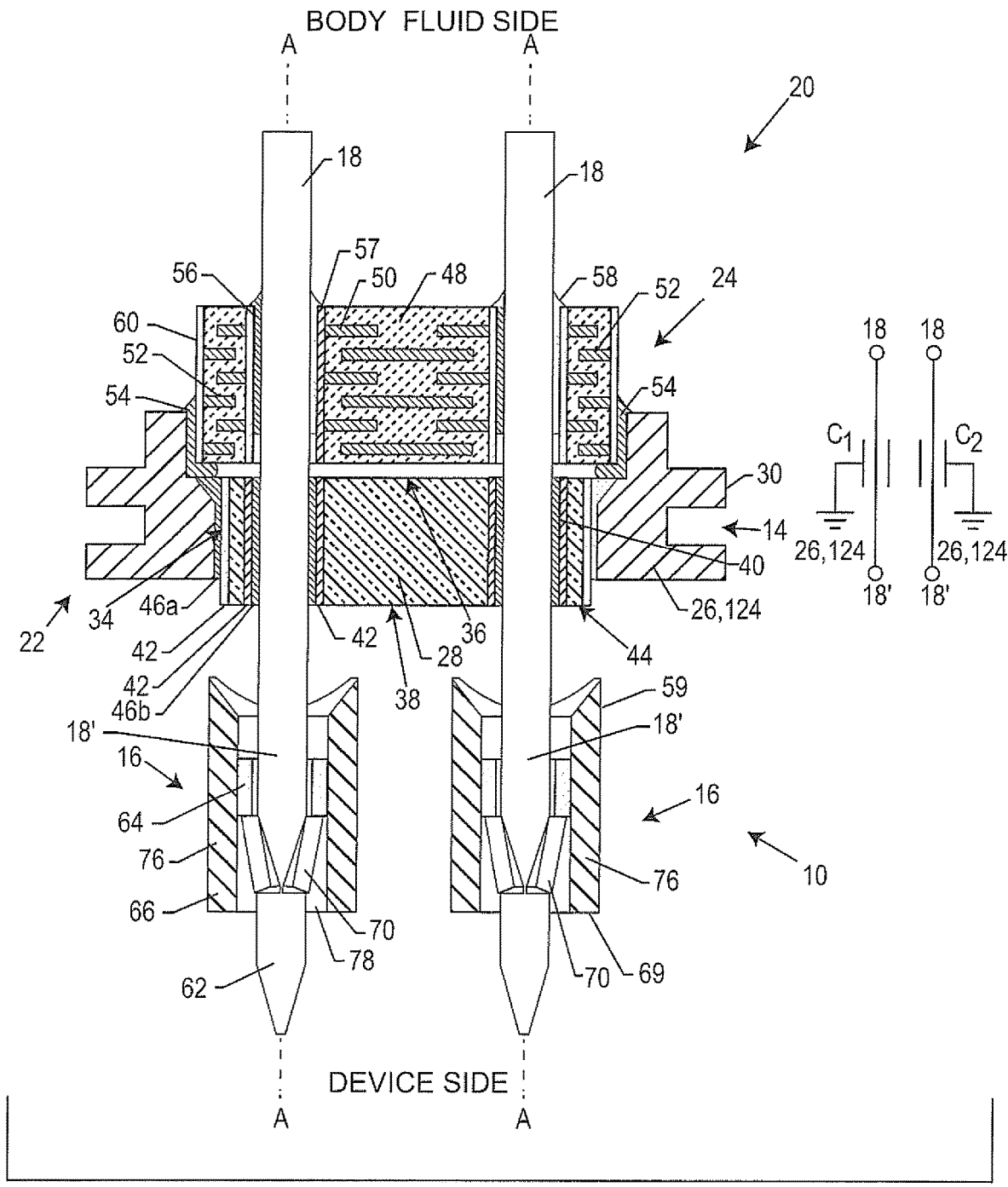
FIG. 3A shows a cross-sectional view of an embodiment of the AIMD feedthrough connector assembly.
Figure 3B:
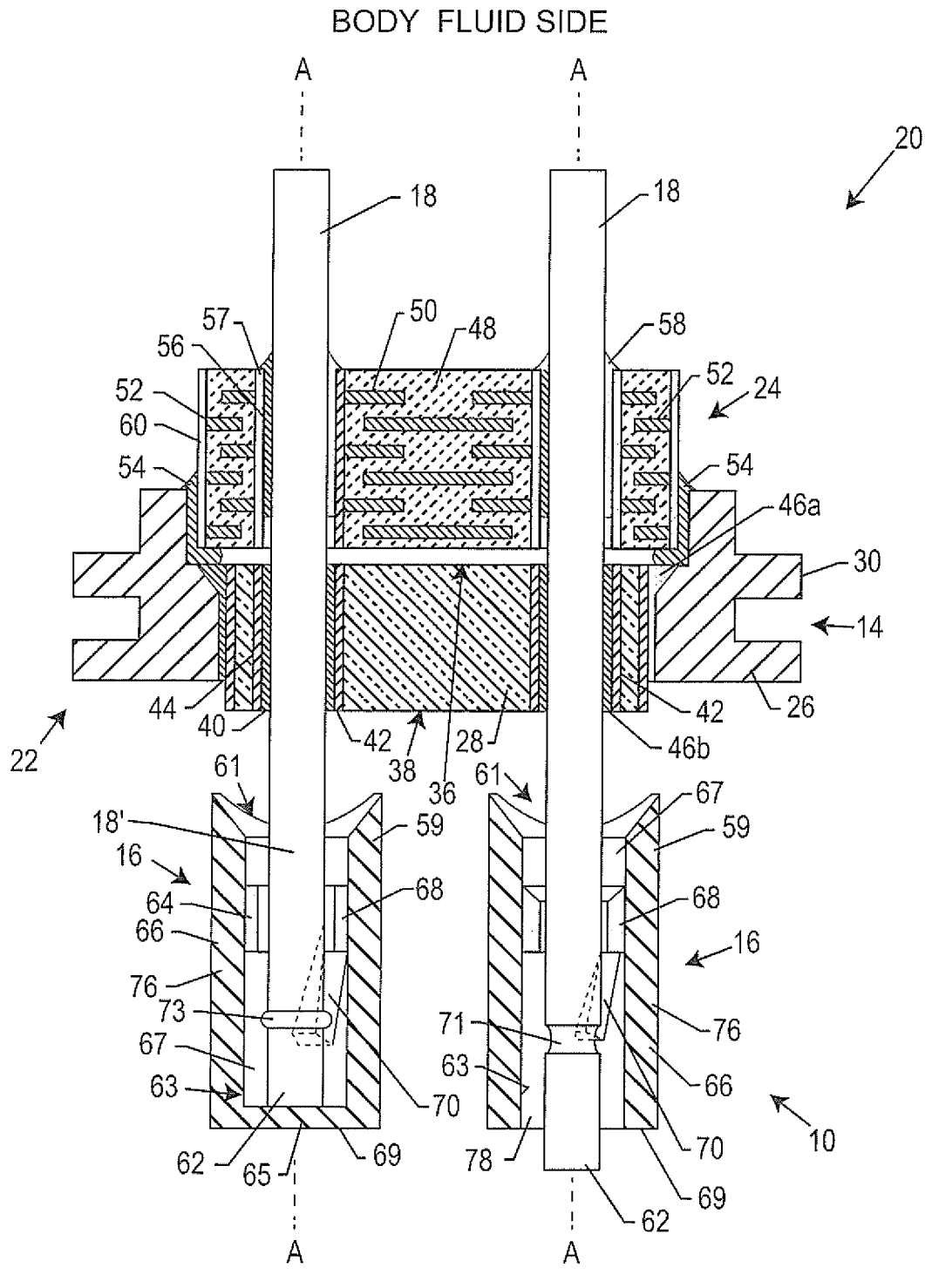
FIG. 3B shows a cross-sectional view of an alternative embodiment of the AIMD feedthrough connector.
Figure 3C:
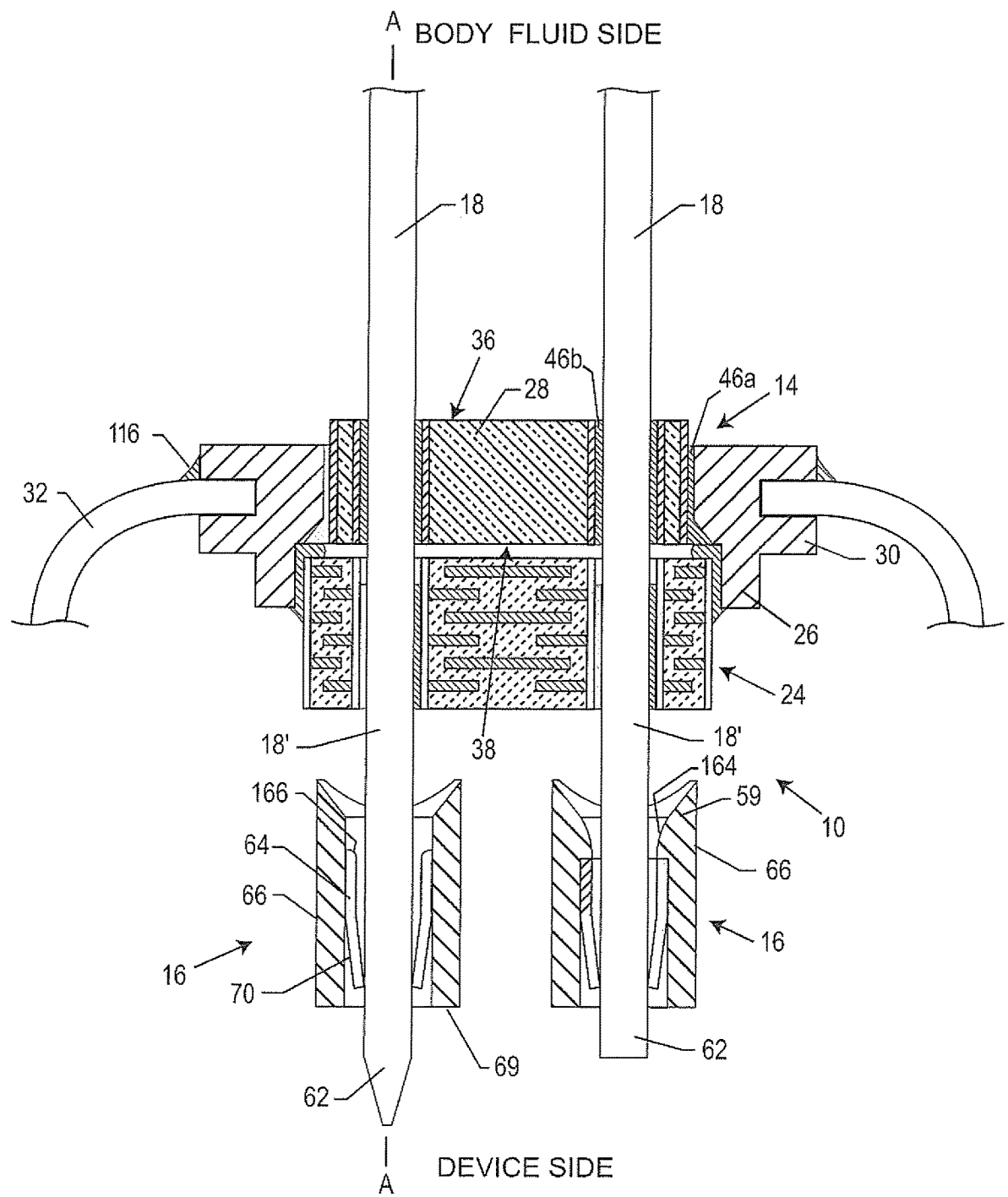
FIG. 3C shows a cross-sectional view of an alternative embodiment of the AIMD feedthrough connector.
Figure 4:
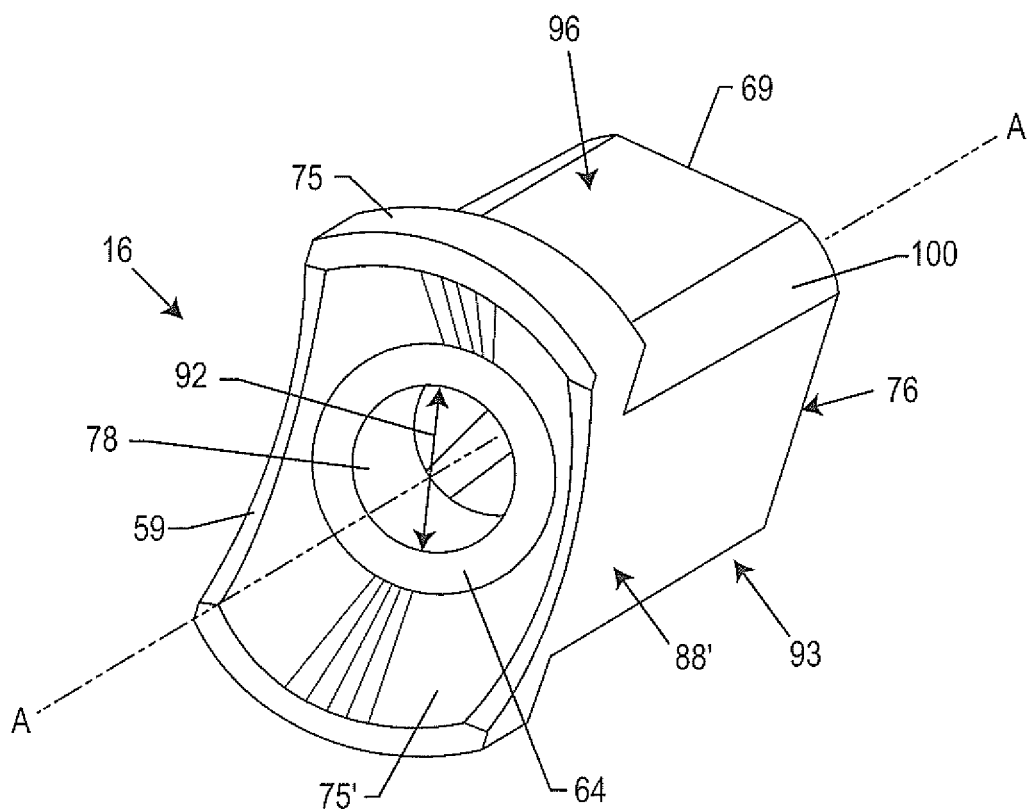
FIG. 4 shows a perspective view of an embodiment of the terminal pin connector.
Figures 5A, 5B, 5C:
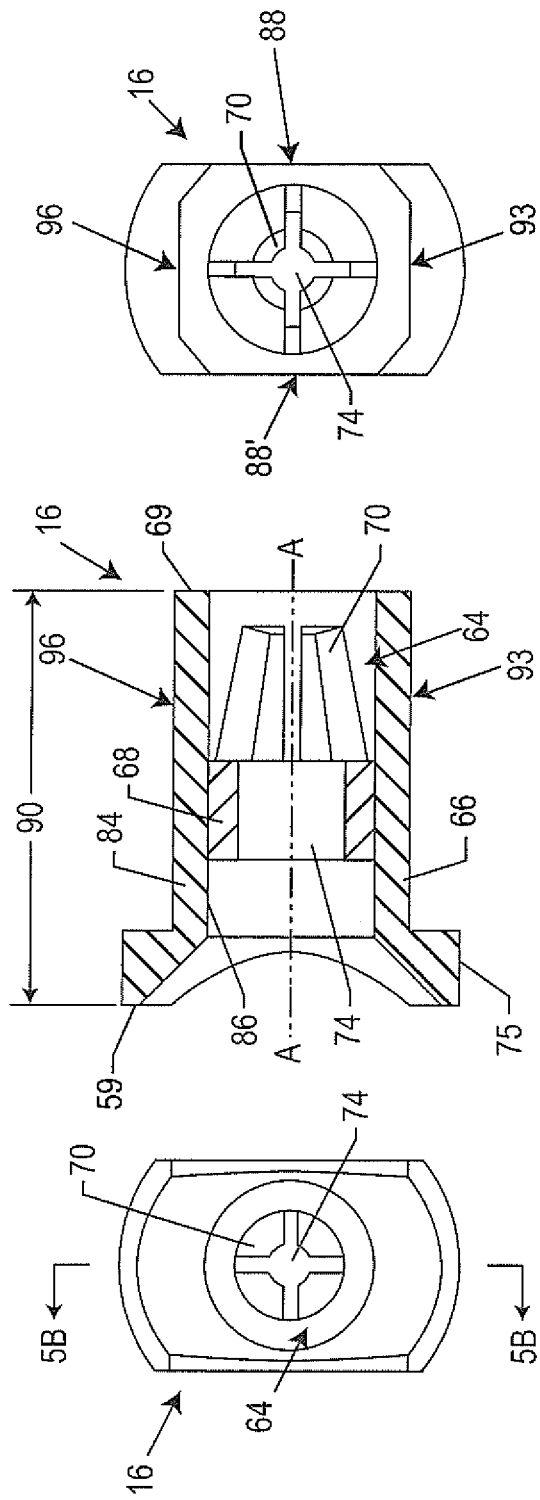
FIG. 5A shows a proximal end view of an embodiment of the terminal pin connector.
FIG. 5B shows a cross-sectional view of the terminal pin connector of FIG. 5A taken along lines 5B-5B.
FIG. 5C shows a distal end view of the terminal pin connector of FIG. 5A.
Figure 5D:
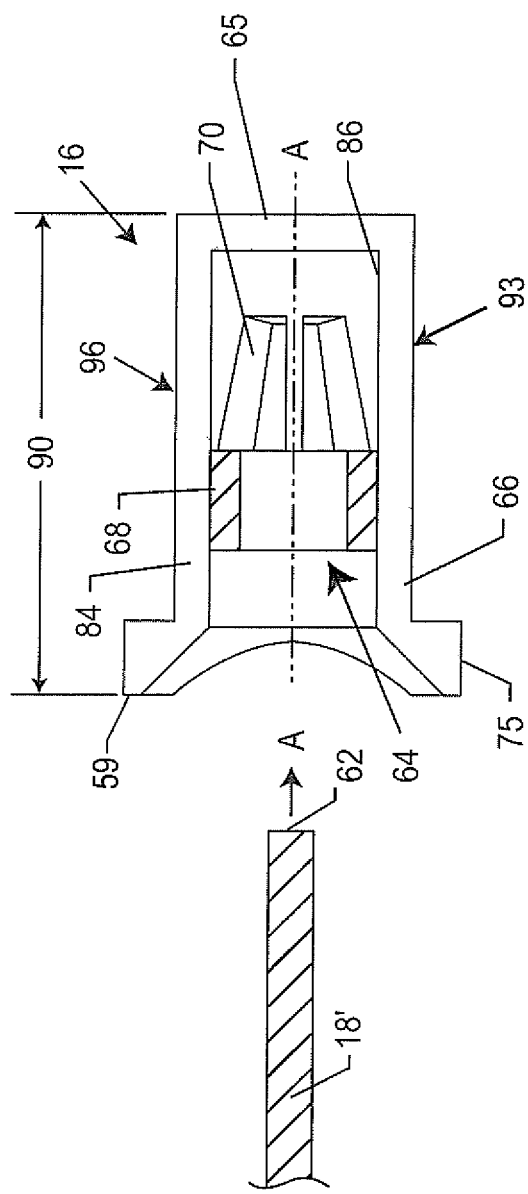
FIG. 5D shows a cross-sectional view similar to FIG. 5B illustrating an alternative embodiment of the terminal pin connector.
Figure 5E:
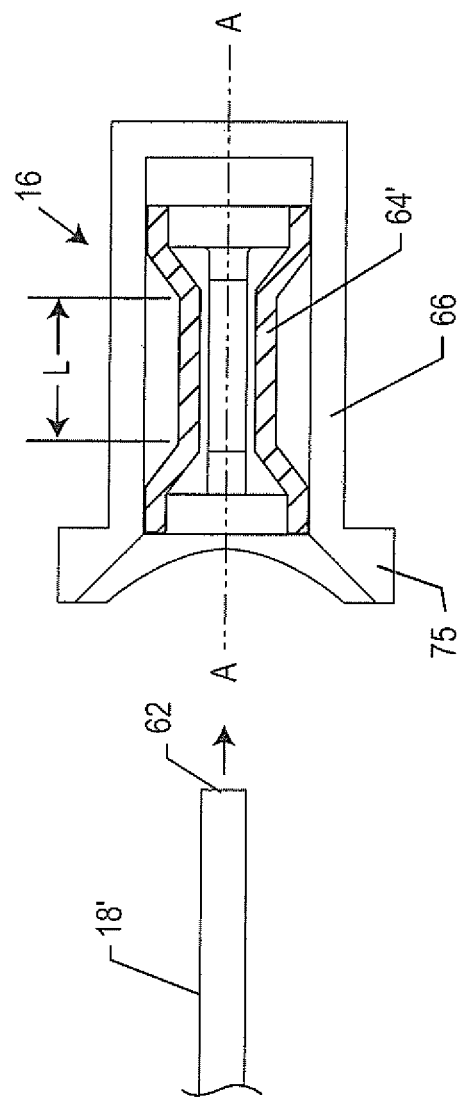
FIG. 5E shows a cross-sectional view similar to FIG. 5B illustrating an alternative embodiment of the terminal pin connector.
Figure 7A:
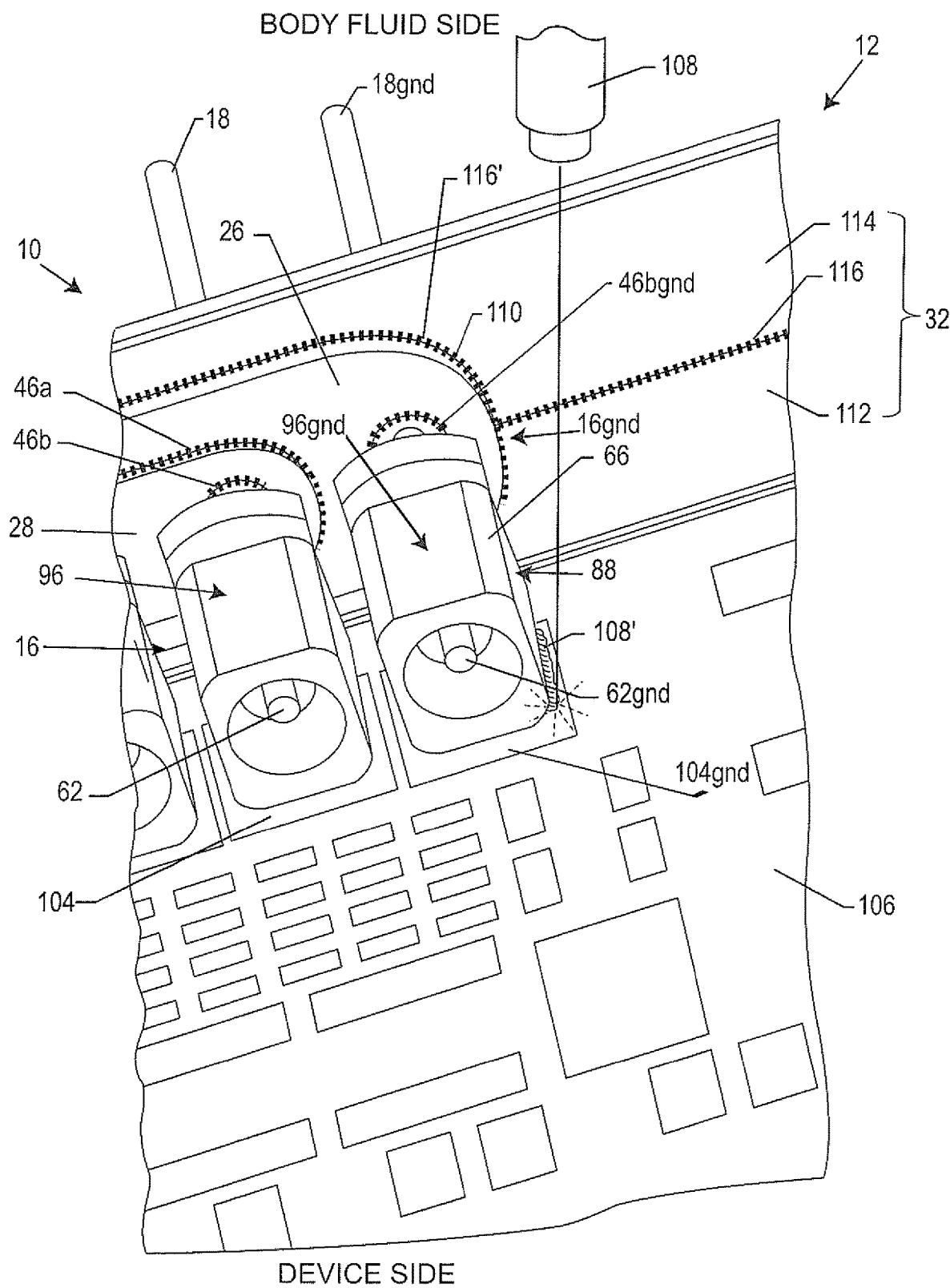
FIG. 7A illustrates an embodiment of the terminal pin connector attached to electrical connection pads of an AIMD active electronic circuit board.
Figure 7B:
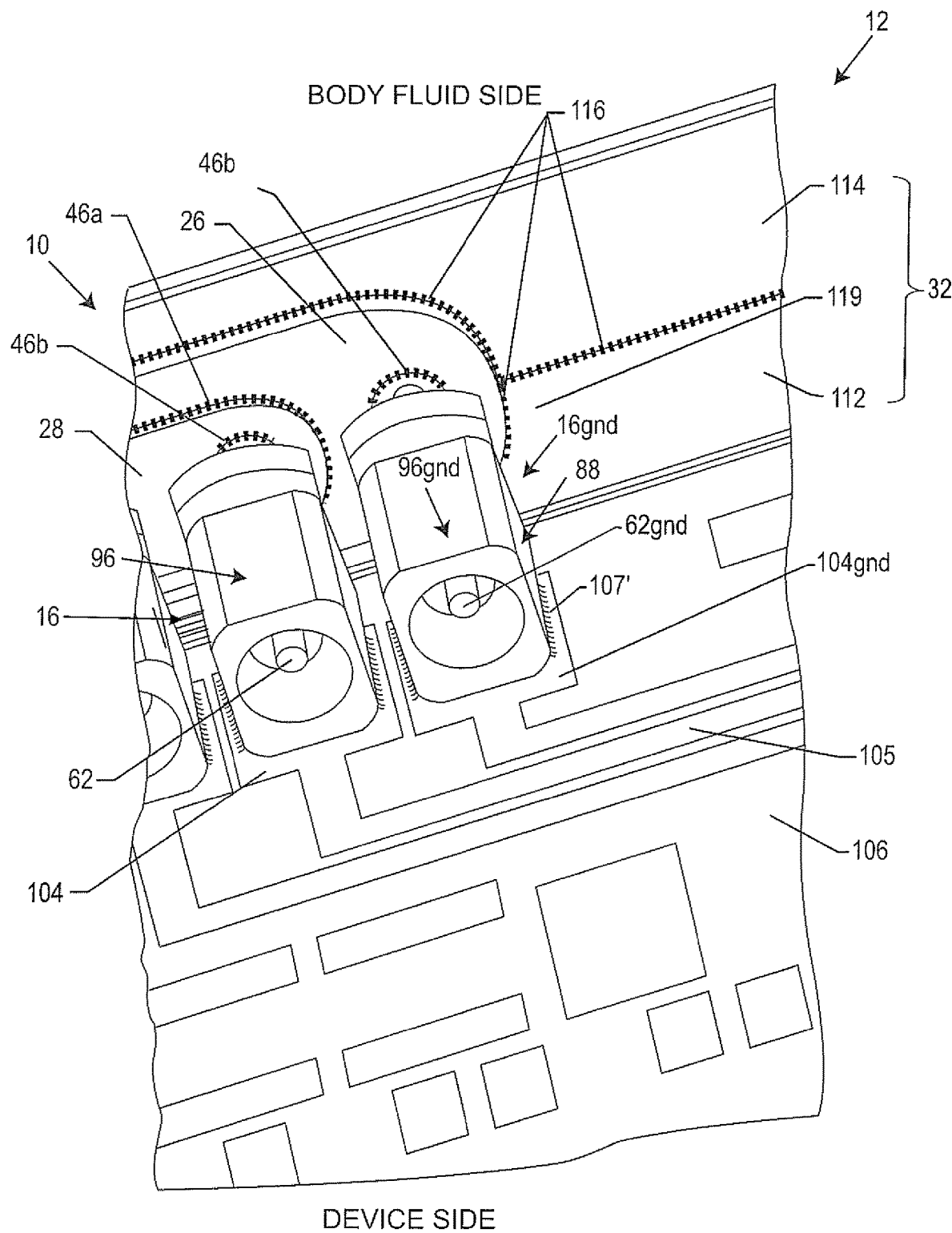
FIG. 7B illustrates an alternative embodiment of the terminal pin connector attached to electrical connection pads of an AIMD active electronic circuit board.
Figure 7C:
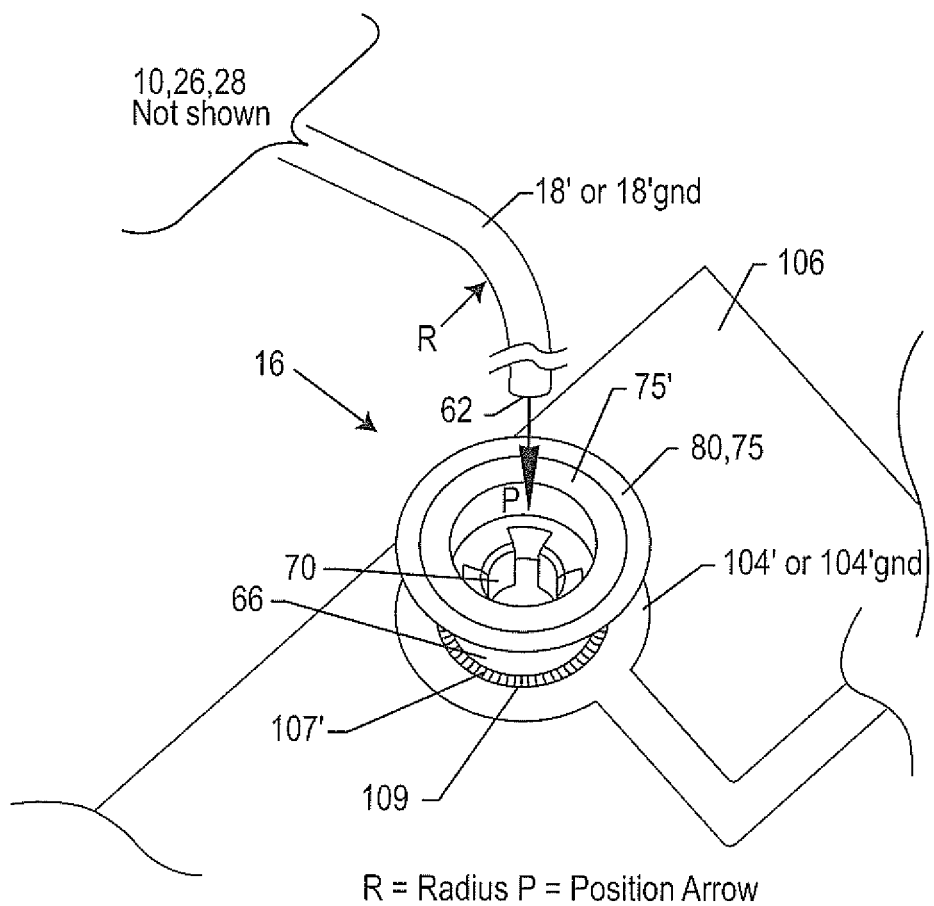
FIG. 7C illustrates an alternative embodiment of the connector assembly attached to a via hole of an AIMD active electronic circuit board.
Figure 8:
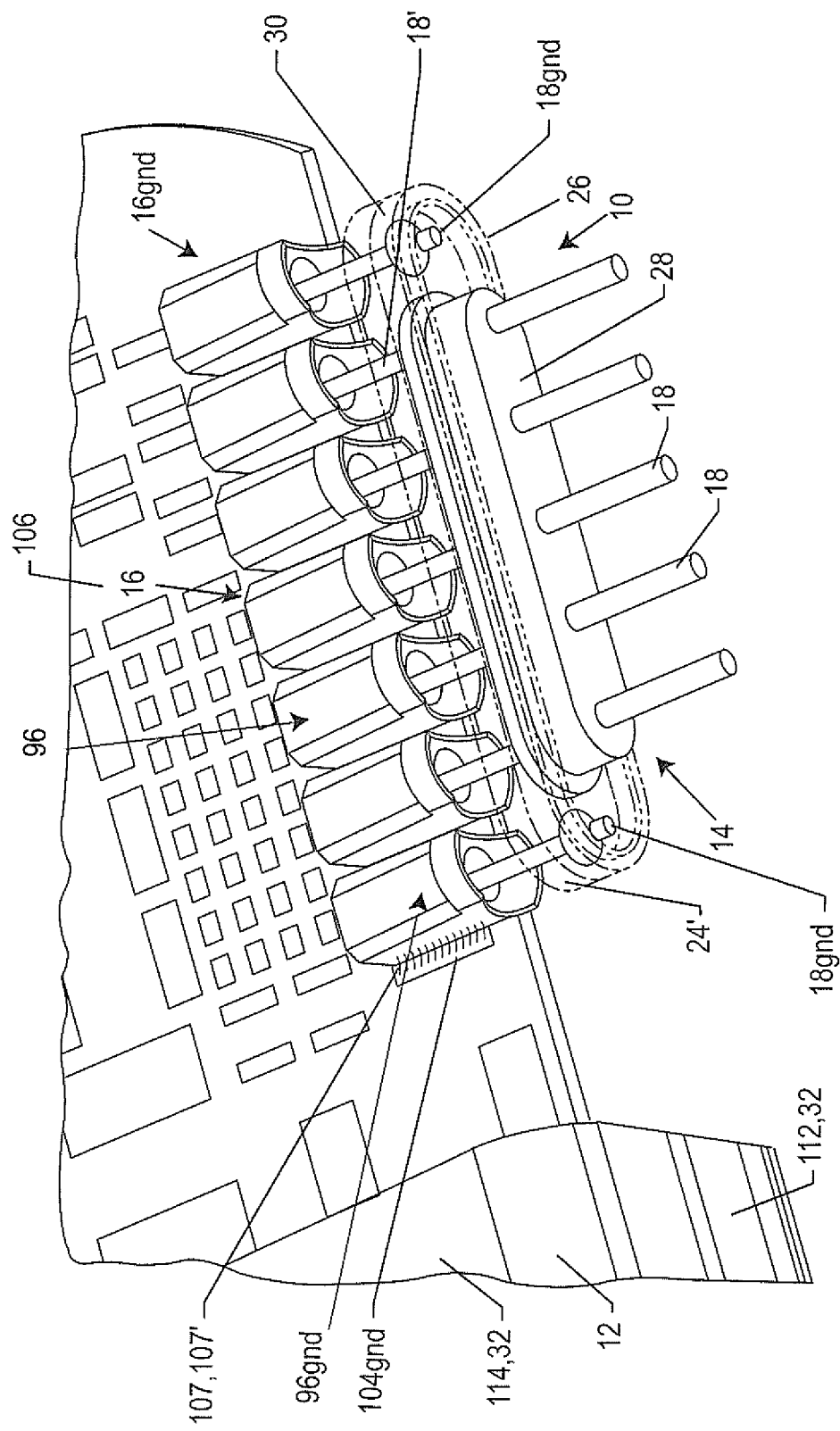
FIG. 8 shows an enlarged partial cross-sectional perspective view of an embodiment of an AIMD feedthrough connector assembly attached to the AIMD active electronic circuit.
Figure 9:
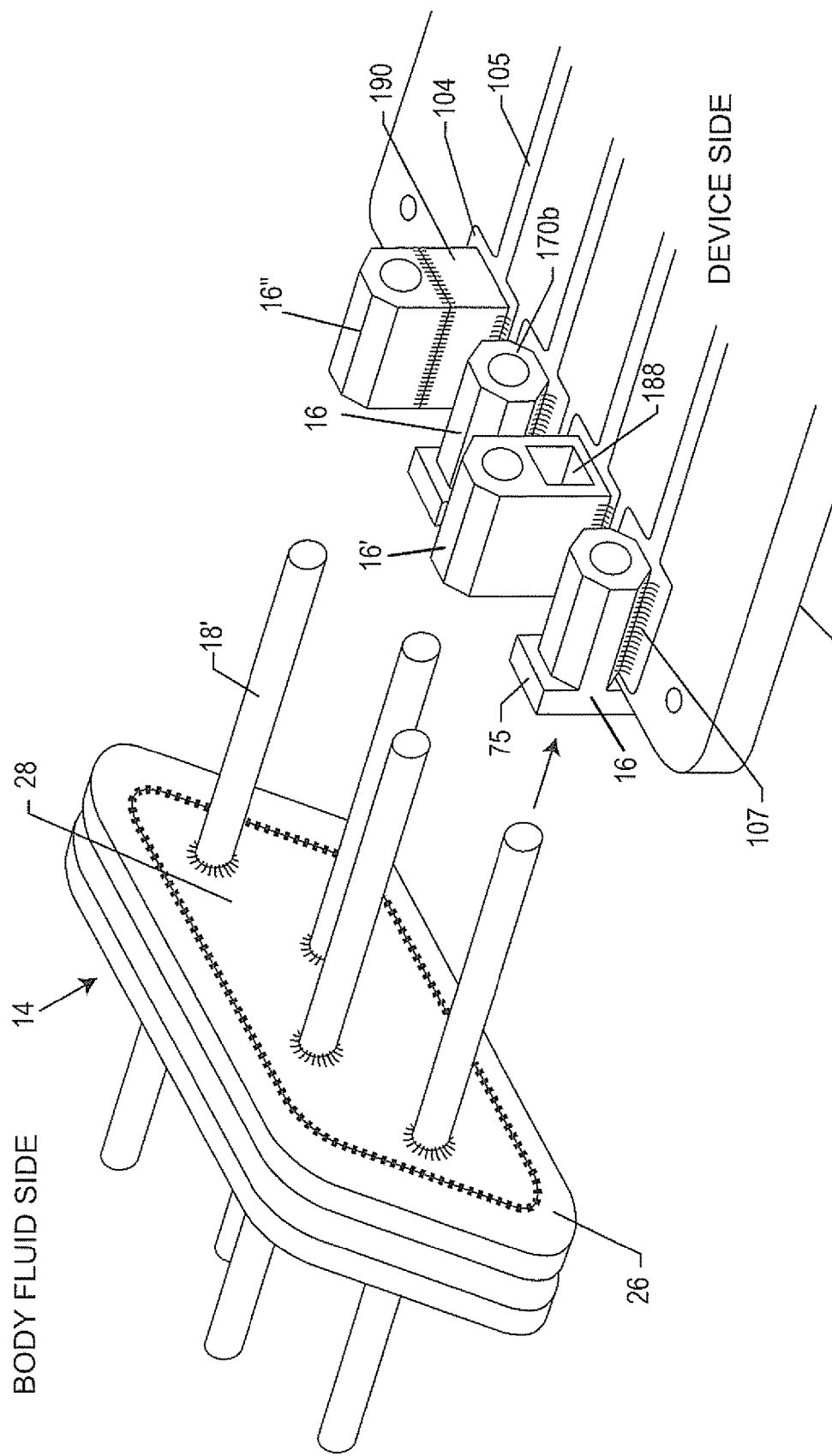
FIG. 9 illustrates a perspective view of an alternative embodiment of the terminal pin connector attachable to an AIMD hermetically sealed feedthrough having a staggered terminal pin configuration.
Figure 10:
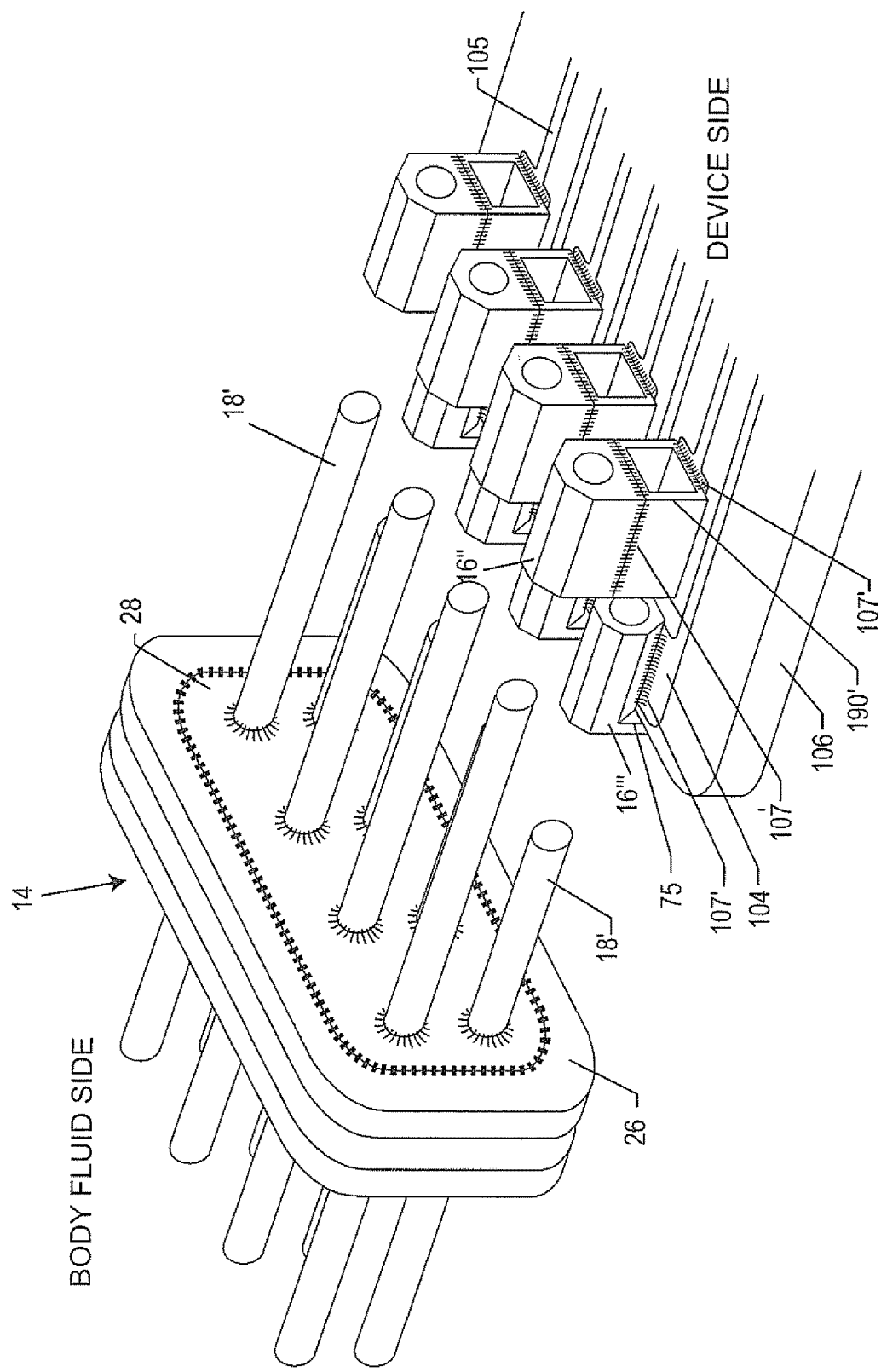
FIG. 10 illustrates a perspective view of an alternative embodiment of the terminal pin connector attachable to an AIMD hermetically sealed feedthrough having an orientation comprising aligned terminal pin pairs of different terminal pin lengths.
Figure 11:
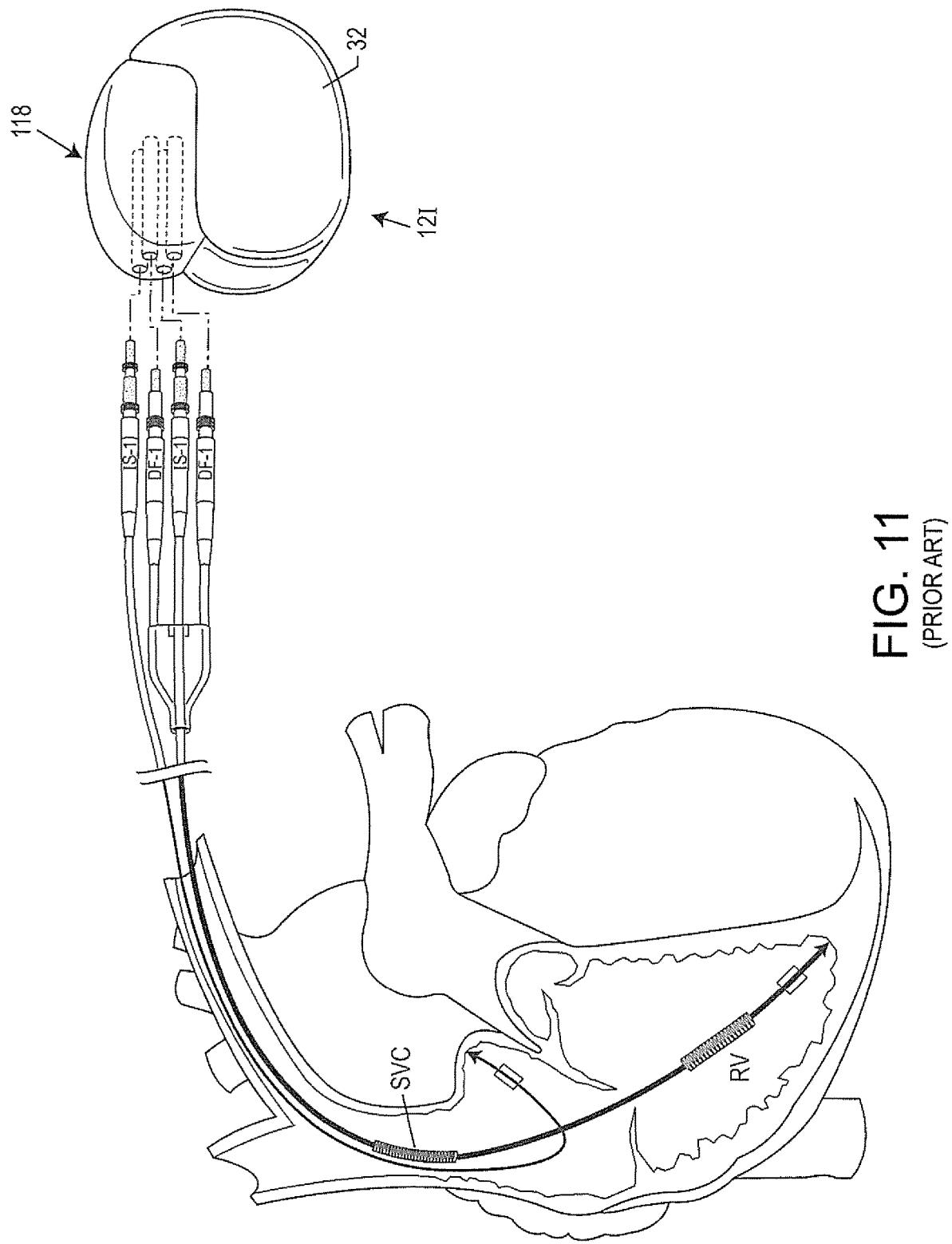
FIG. 11 illustrates an active implantable medical device connectable to a heart of a patient.
Figure 12:
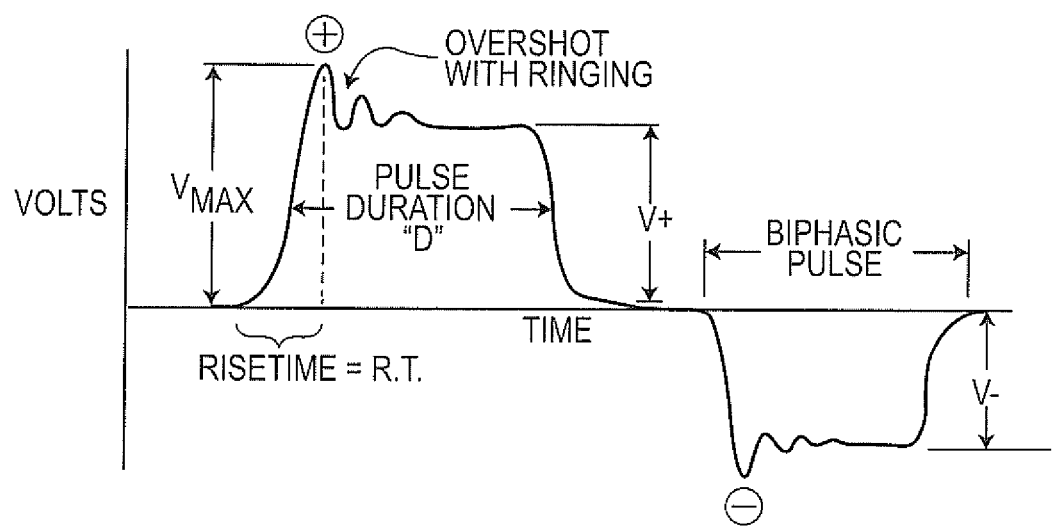
FIG. 12 illustrates a volts vs. risetime graph illustrating an ICD high-voltage biphasic pulse with overshoot and ringing.
Figure 13:
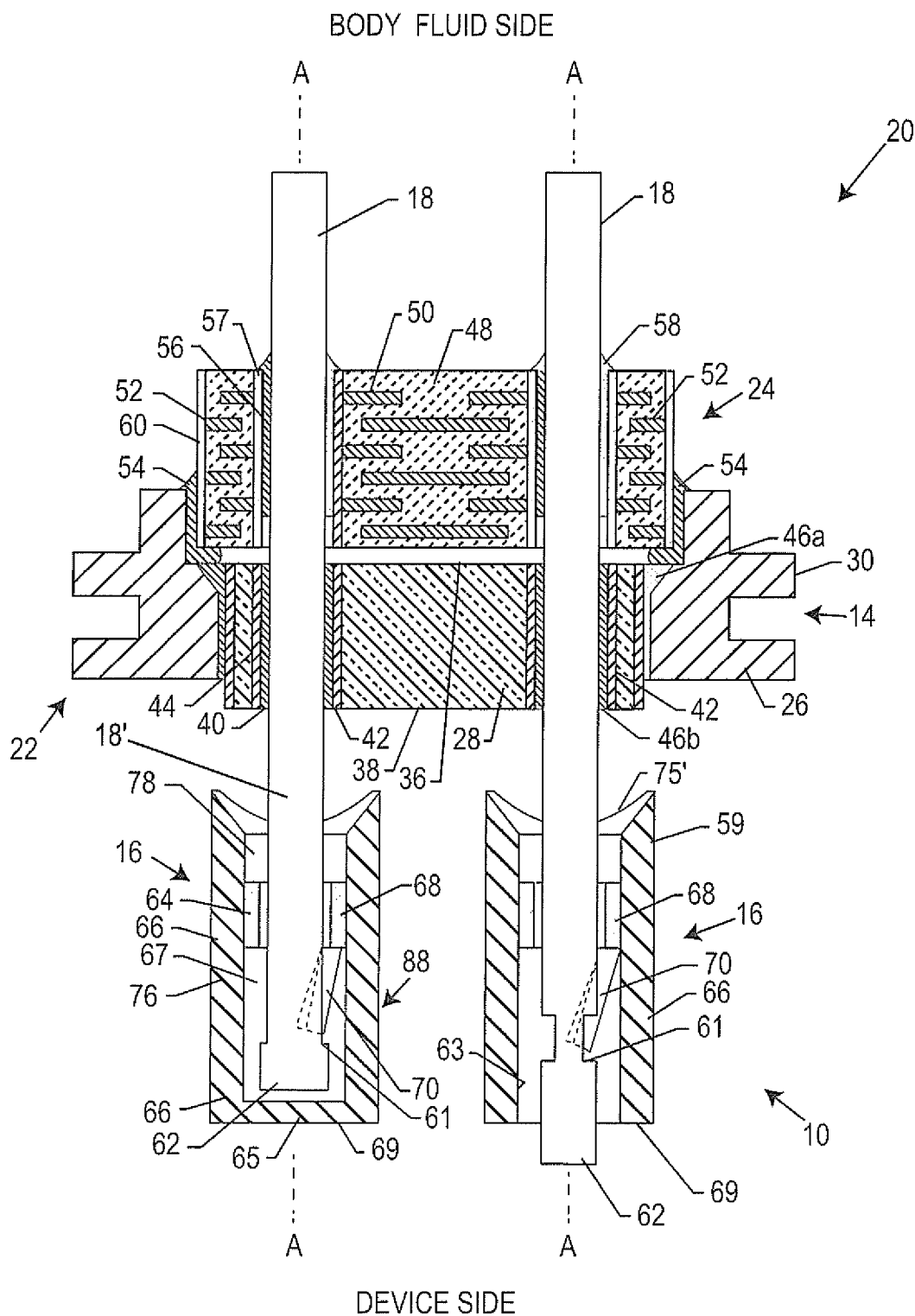
FIG. 13 illustrates a perspective second-side view of the exemplary internal conductors, lead connectors and terminal pin connectors.
Figures 14A, 14B:
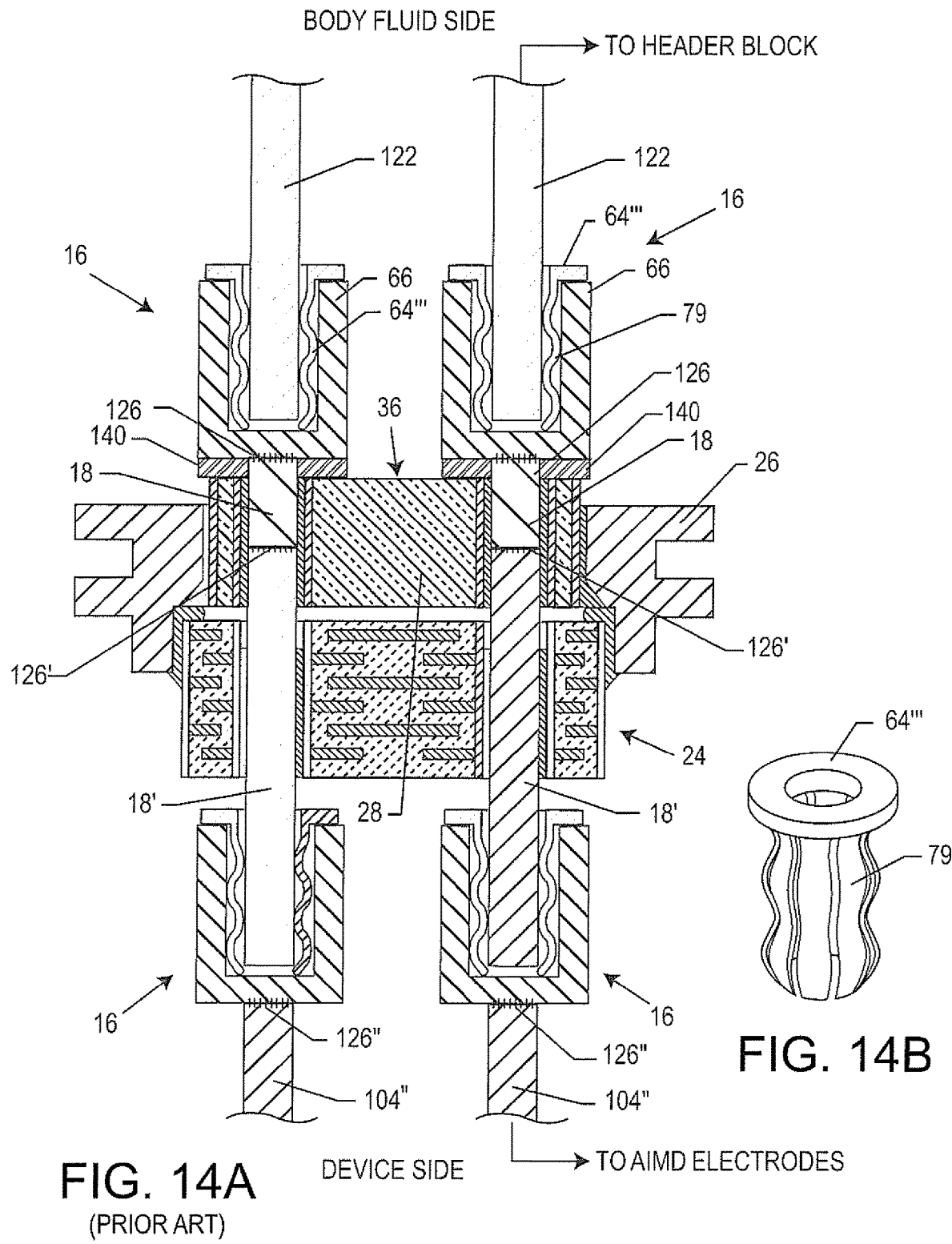
FIG. 14A shows a cross-sectional view of an alternative embodiment of a feedthrough capacitor connector assembly.
FIG. 14B is a perspective view of the clip of FIG. 14A.
Figure 15:
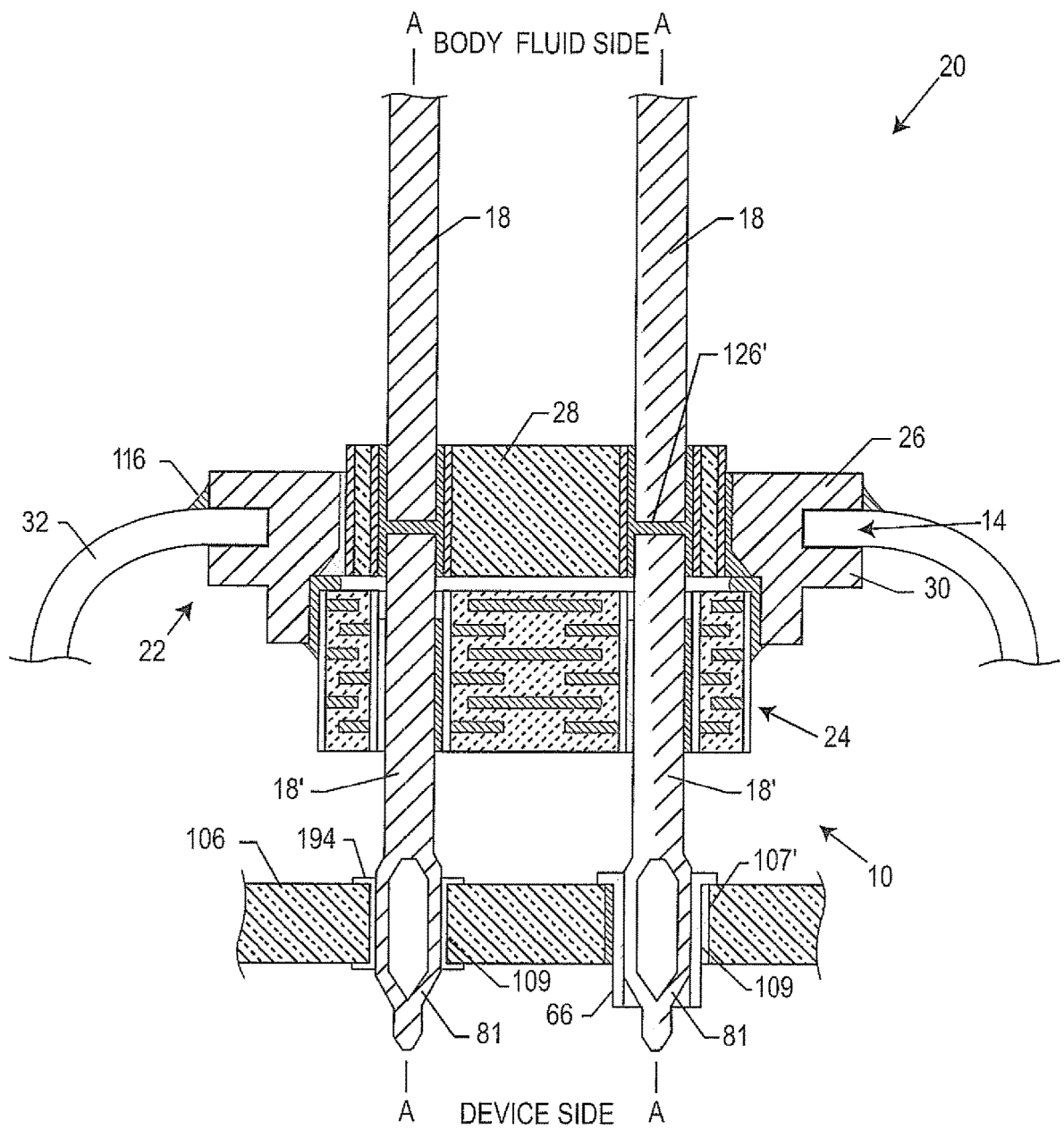
FIG. 15 shows a cross-sectional view of an alternative embodiment of a feedthrough capacitor connector assembly having terminal pins comprising a compliant termination structure.
Figure 15A:
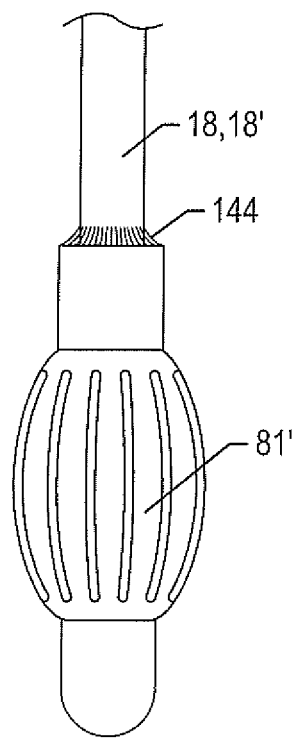
FIGS. 15A-15D illustrates alternative embodiments of the compliant termination structure for a terminal pin connector.
Figure 15B:
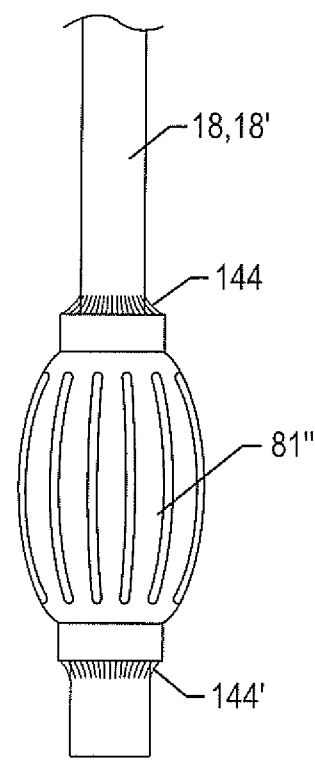
Figure 15C:
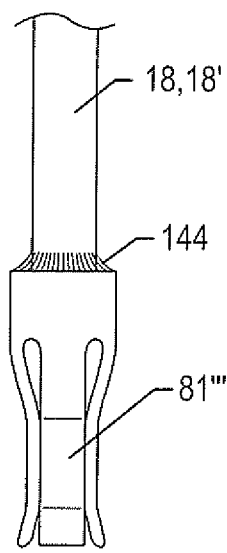
Figure 15D:
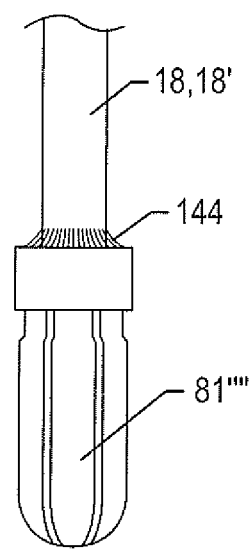
Figure 16:
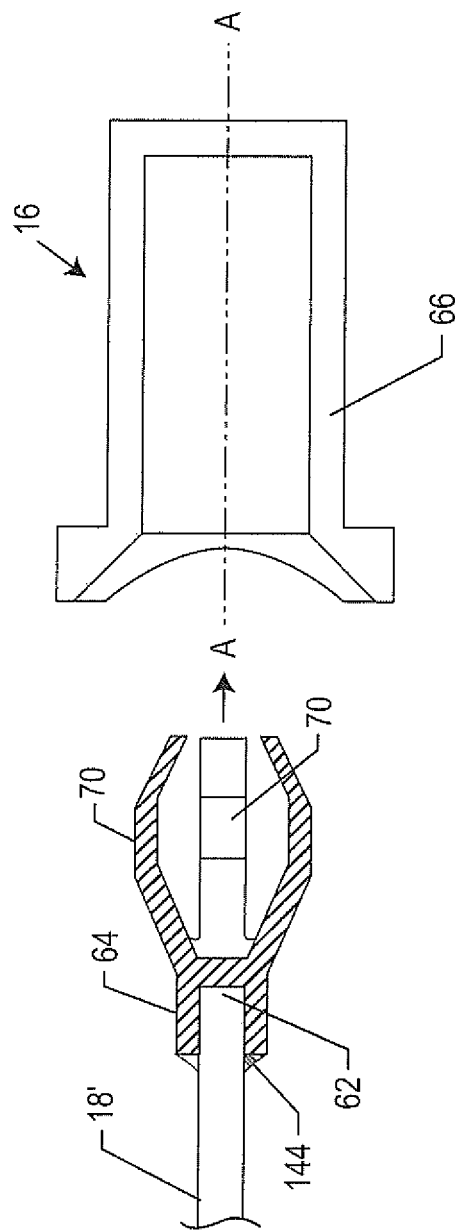
FIGS. 16 and 17 illustrate additional alternative compliant termination structure embodiments for a terminal pin connector.
Figure 17:
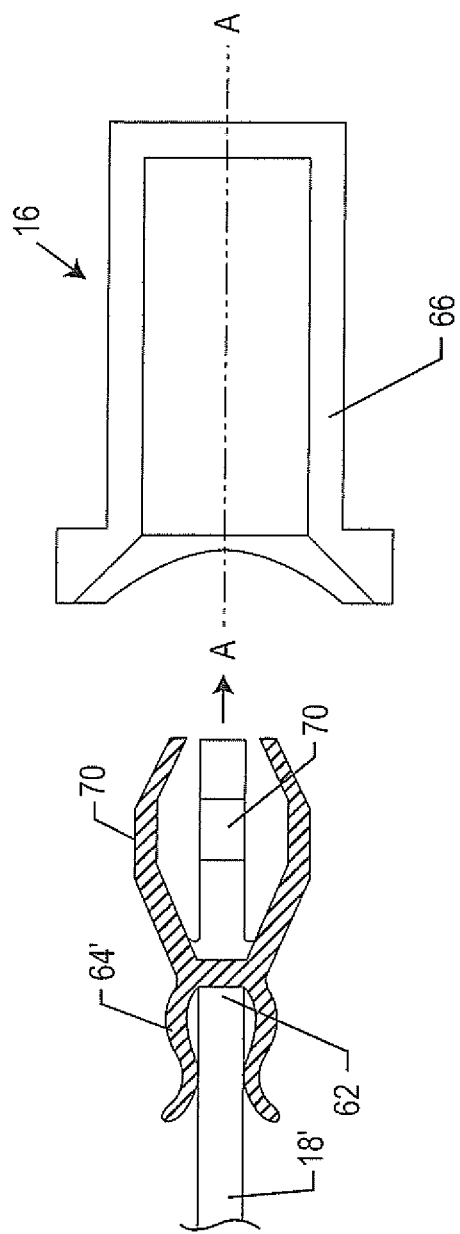
Figure 18:
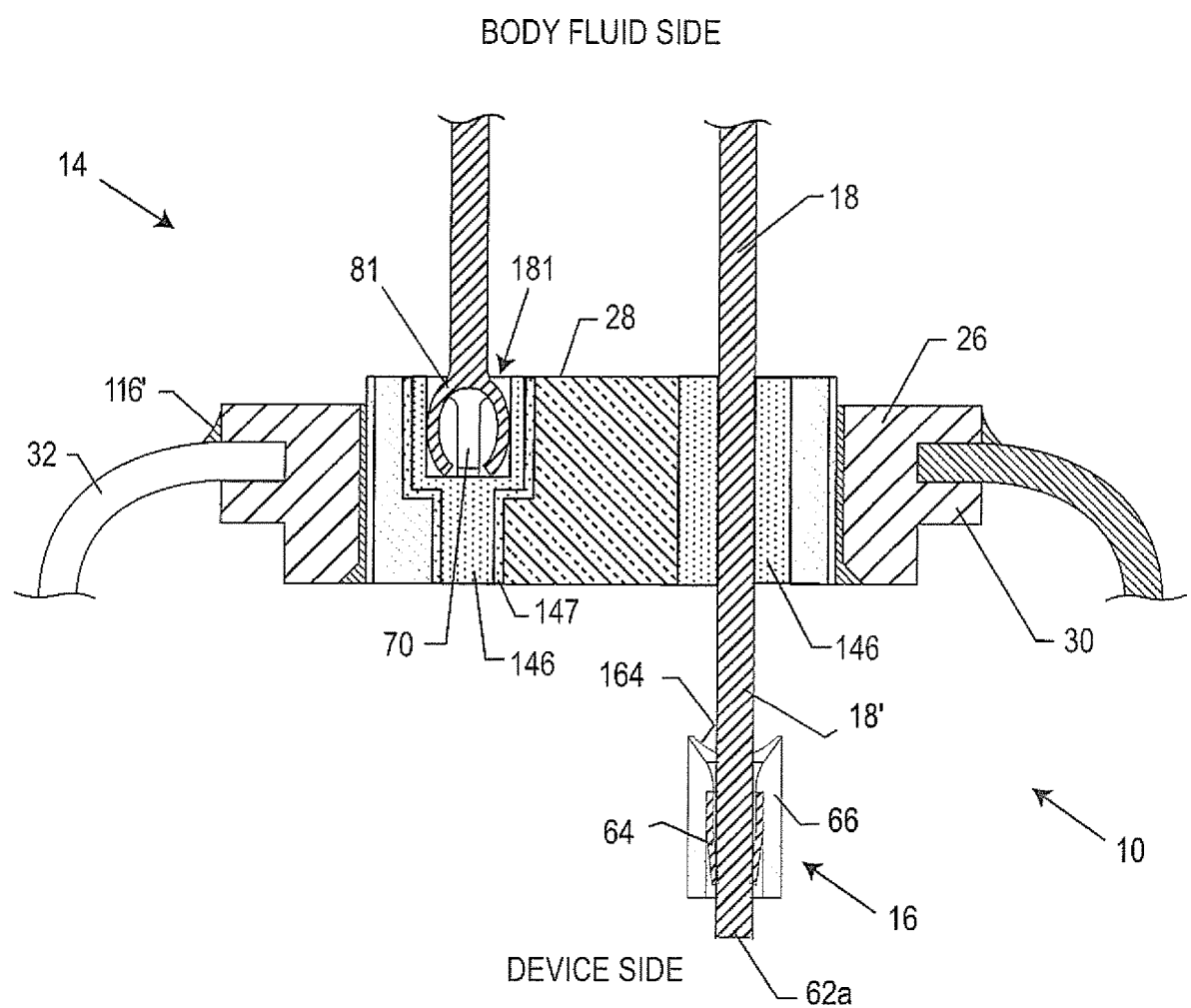
FIG. 18 is a feedthrough assembly illustrating an embodiment of a compliant terminal pin connector (on the left) electrically connected to a co-sintered conductive paste-filled via and a terminal pin connector (on the right) comprising prongs to electrically connect to a terminal pin co-fired to a co-sintered conductive paste-filled via.
Figure 19A:
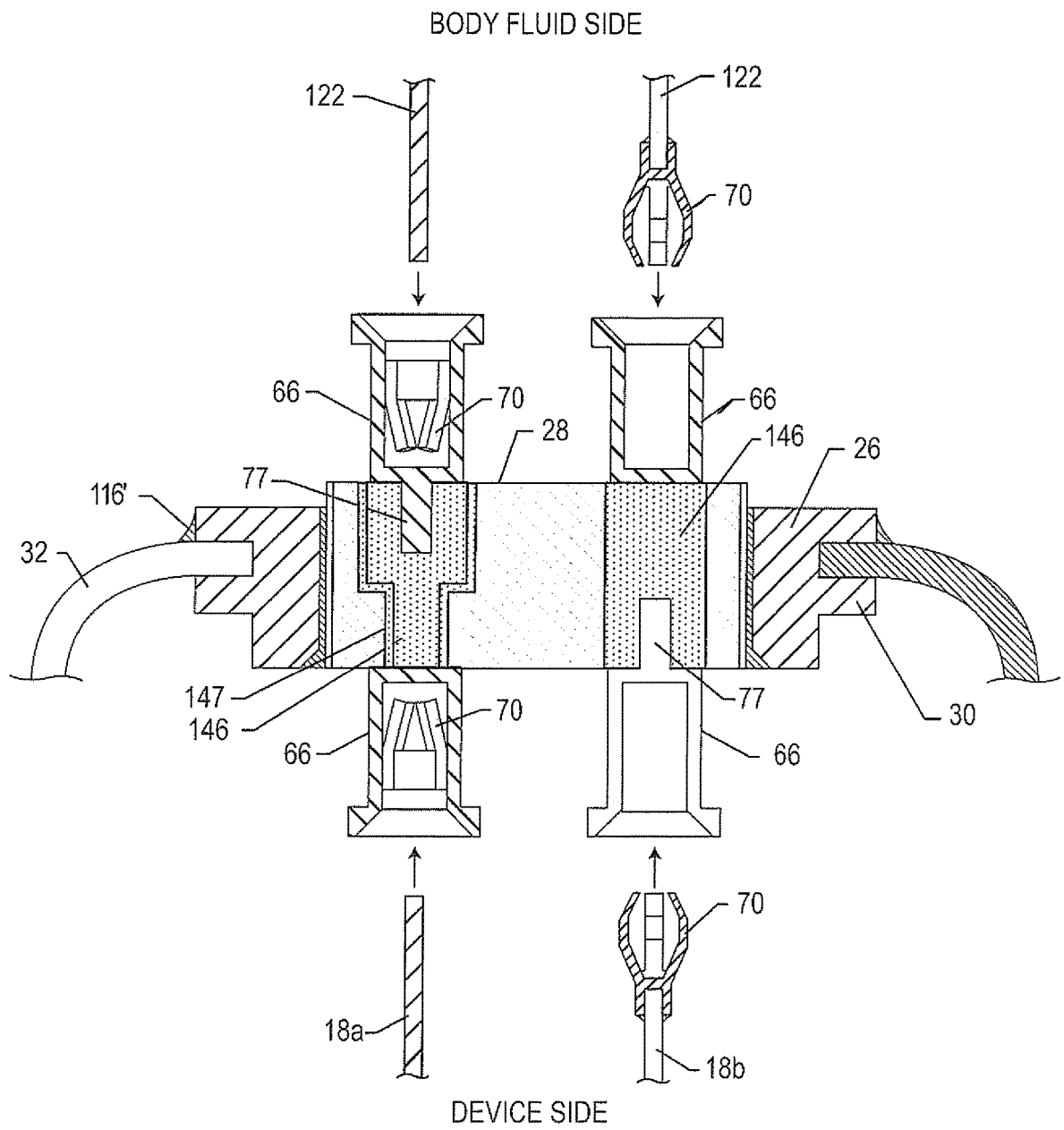
FIG. 19A shows a cross-sectional view of alternative terminal pin connector embodiments for electrically connecting components to the body fluid side and/or the device side of an AIMD hermetic feedthrough terminal assembly.
Figure 19B:
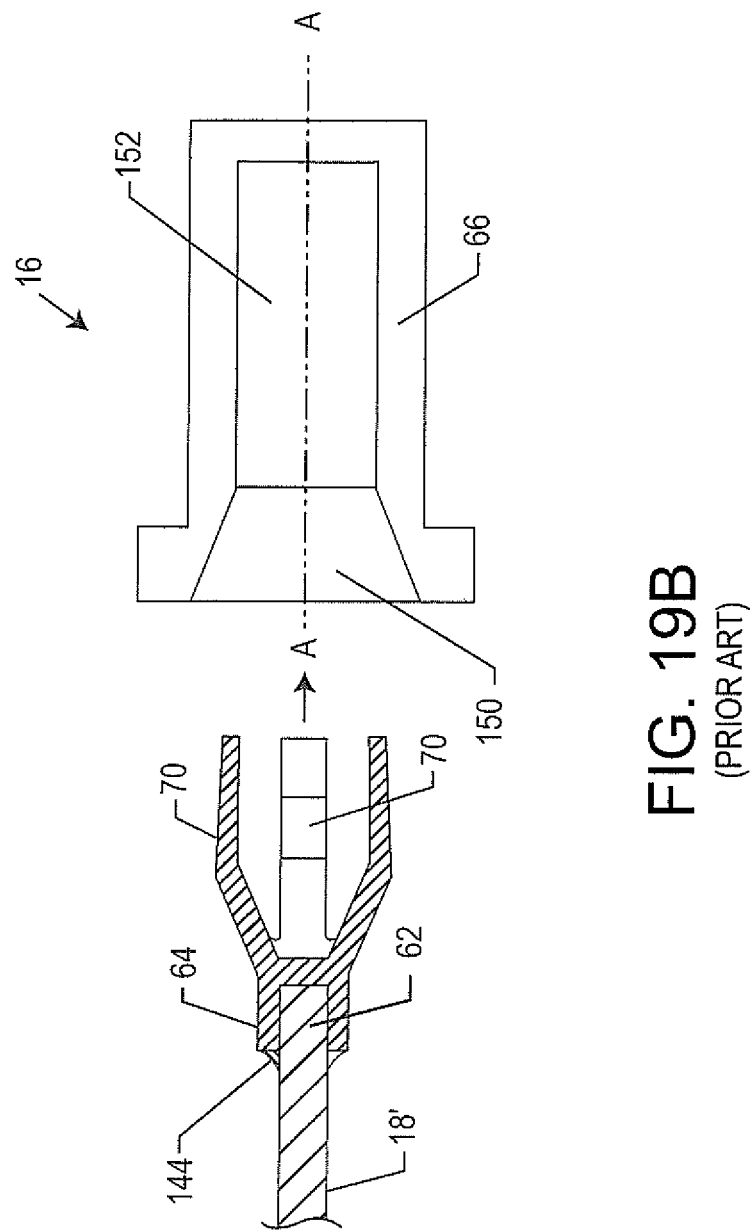
FIGS. 19B and 20 show a cross-sectional view of alternative terminal pin connector embodiments.
Figure 20:
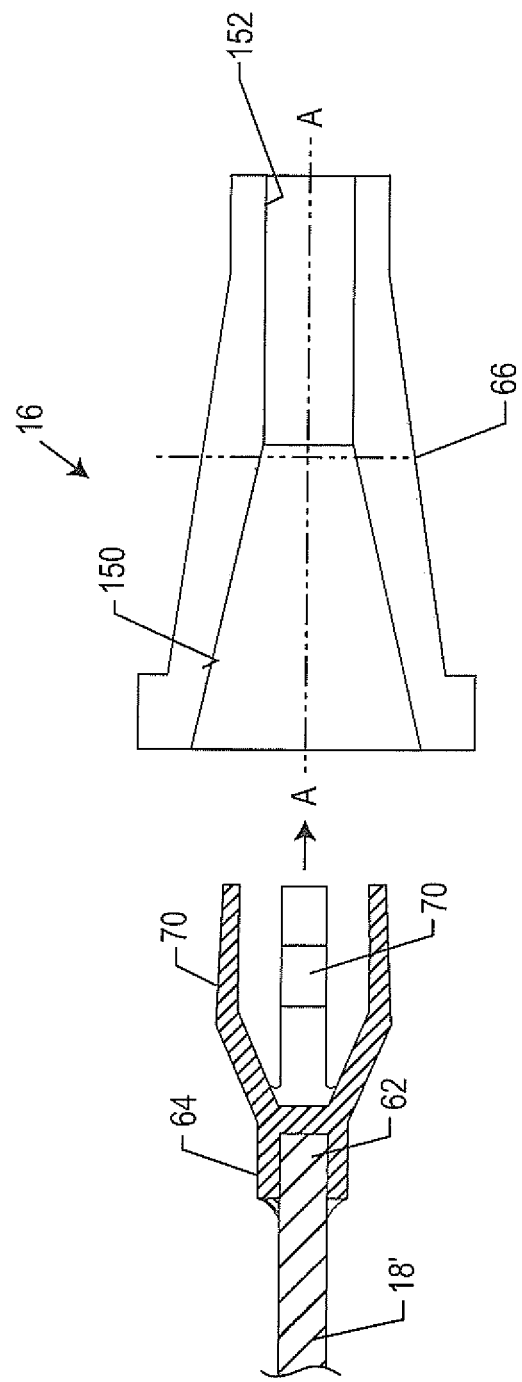
Figure 21:
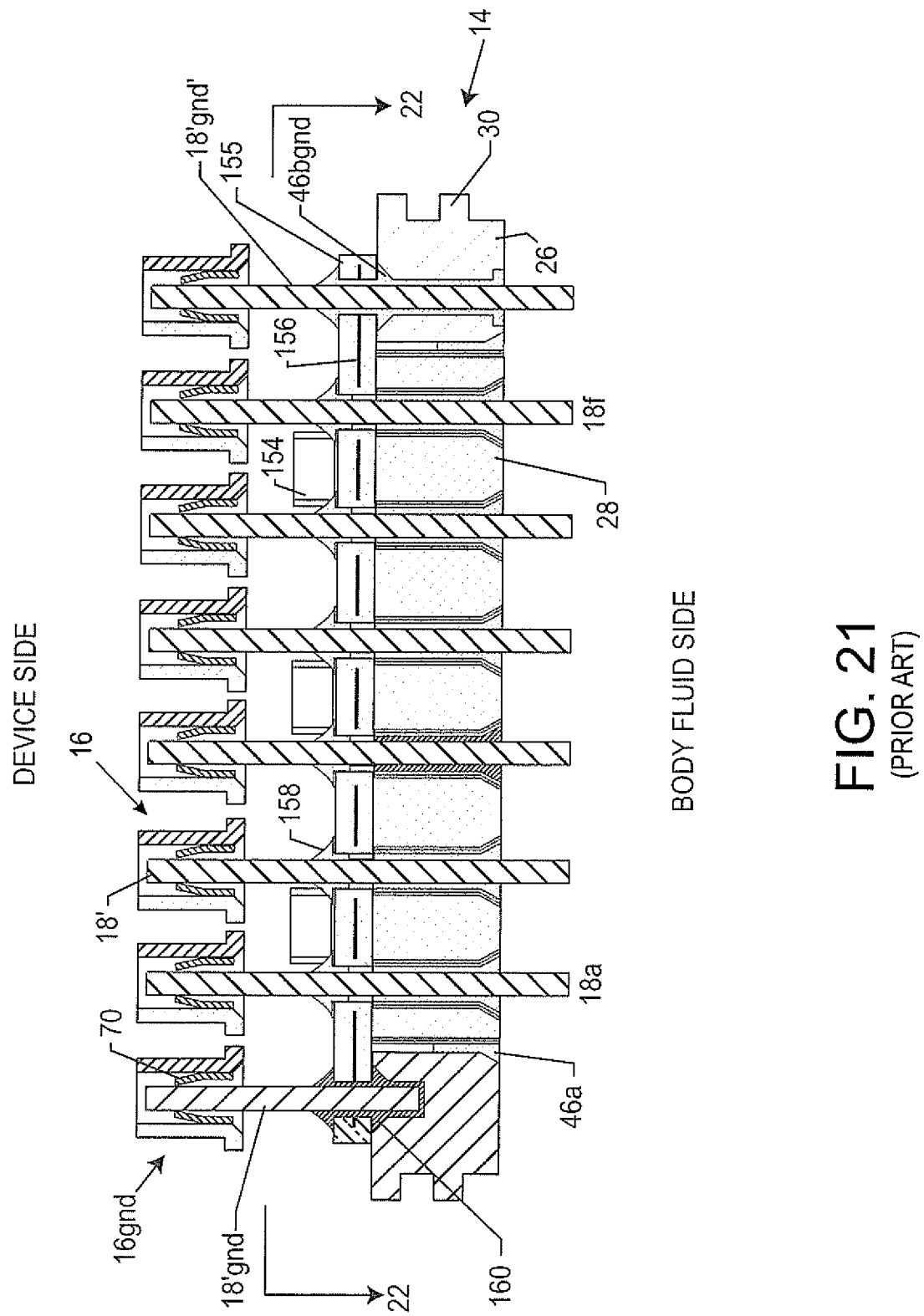
FIG. 21 shows a cross-sectional view of a filtered feedthrough connector assembly having each feedthrough attached to respective terminal pin connectors, the terminal pin connectors being attached to an AIMD active electronic circuit board (not shown) residing on the device side of the AIMD.
Figure 22:
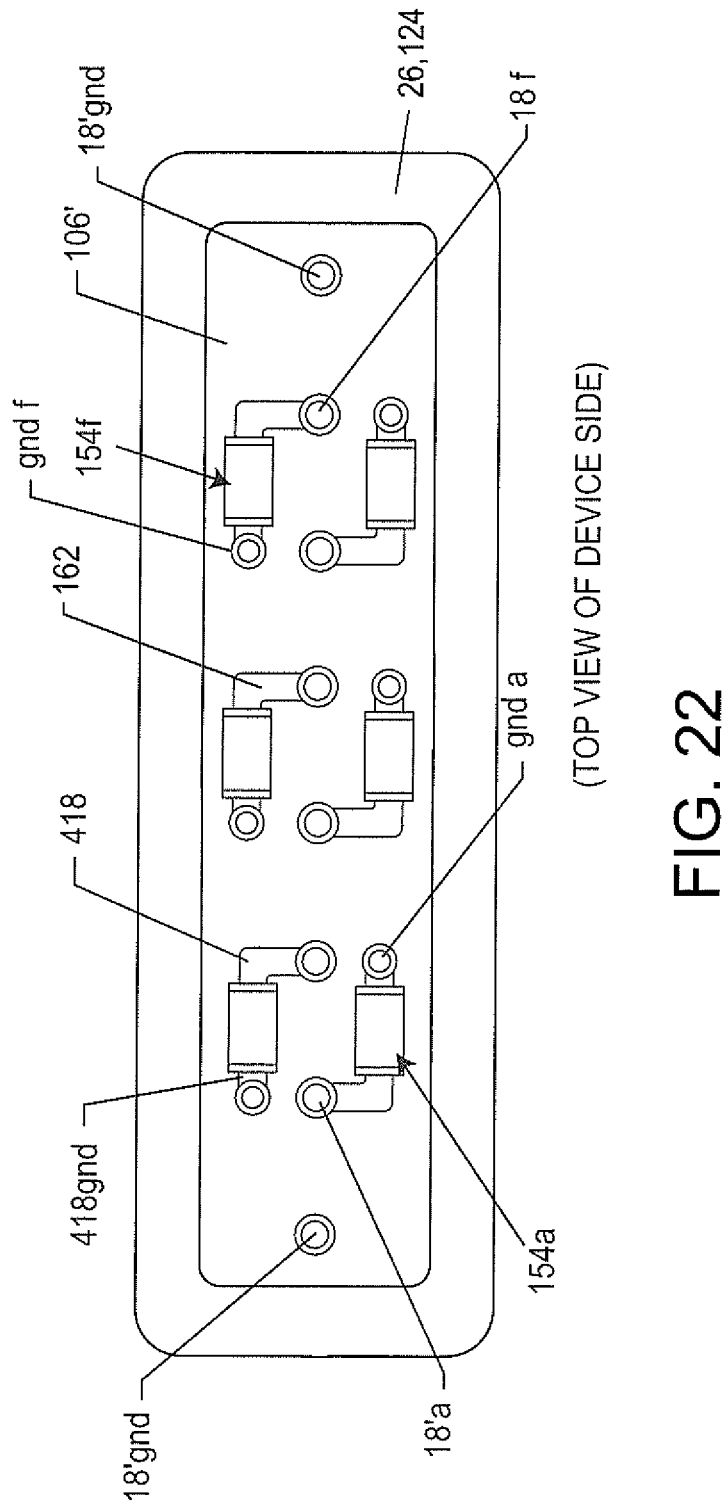
FIG. 22 is a top view taken along lines 22-22 of FIG. 21 showing multi-layer ceramic capacitors (MLCCs) populated on an EMI filter circuit board of the filtered feedthrough connector assembly.
Figure 23A:
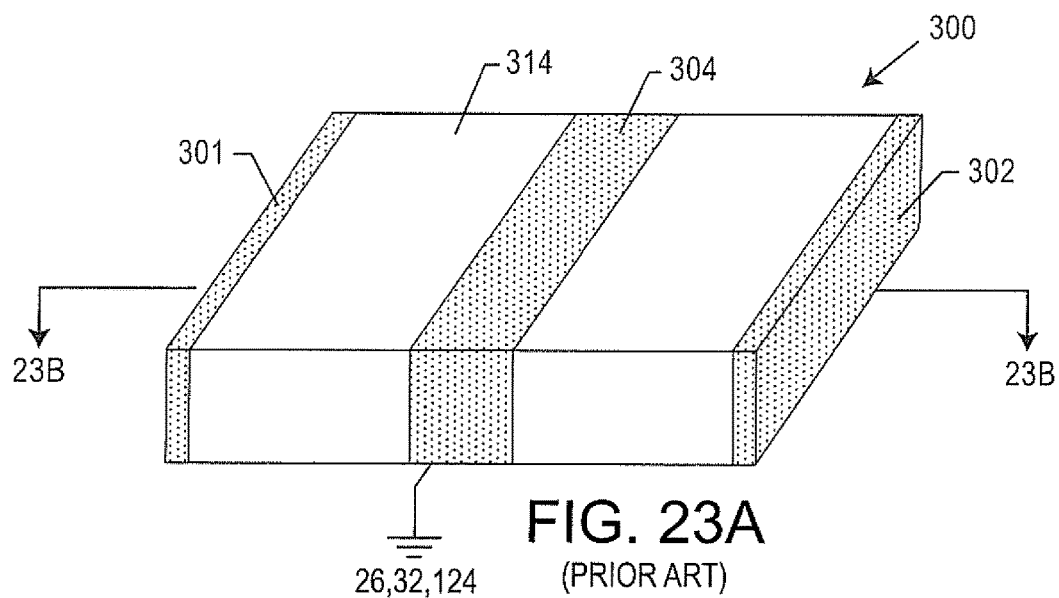
FIG. 23A is a perspective view of a prior art surface mounted capacitor known as an X2Y attenuator.
Figure 23B:
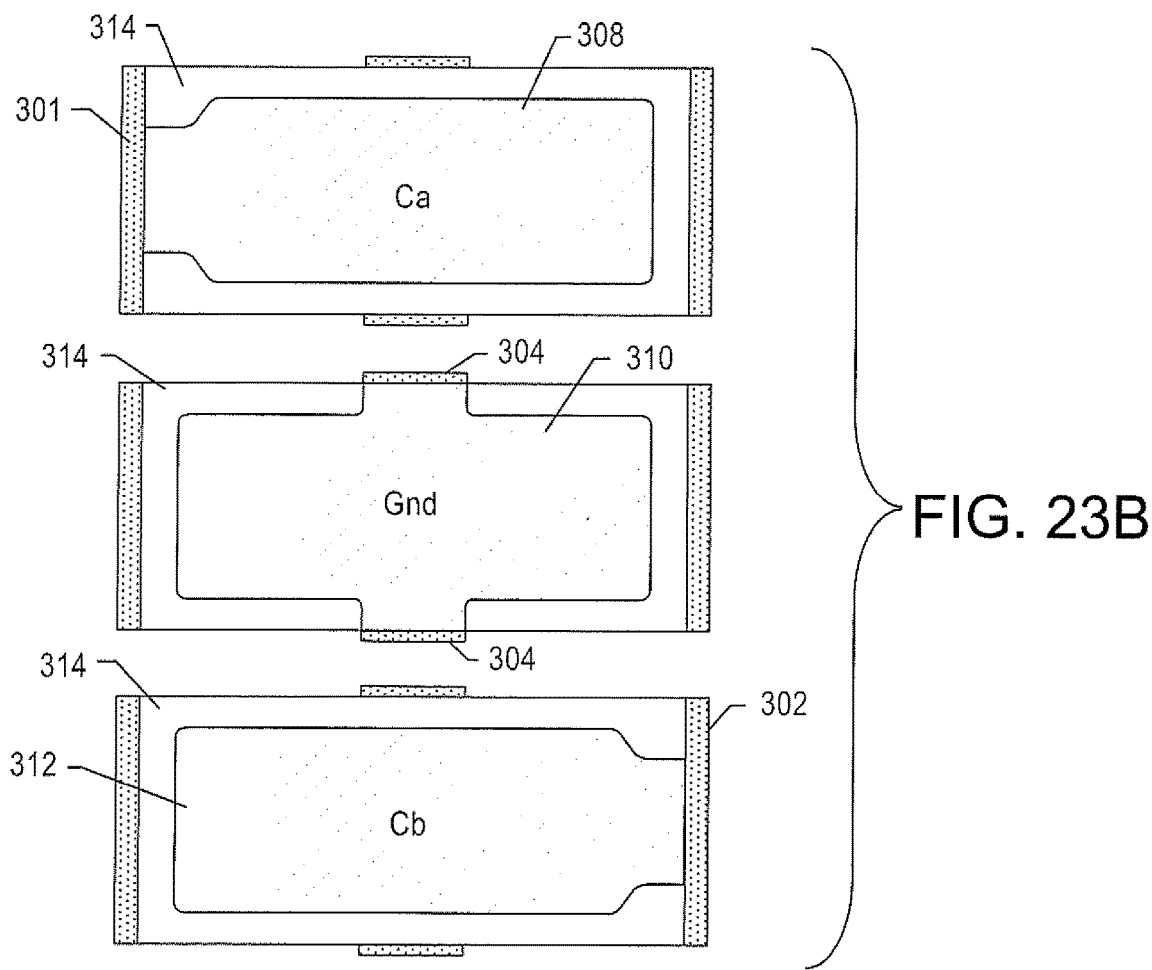
FIG. 23B is a sectional view taken along lines 23B-23B of FIG. 28A showing the active and ground electrode plates of the X2Y attenuator.
Figure 24A:
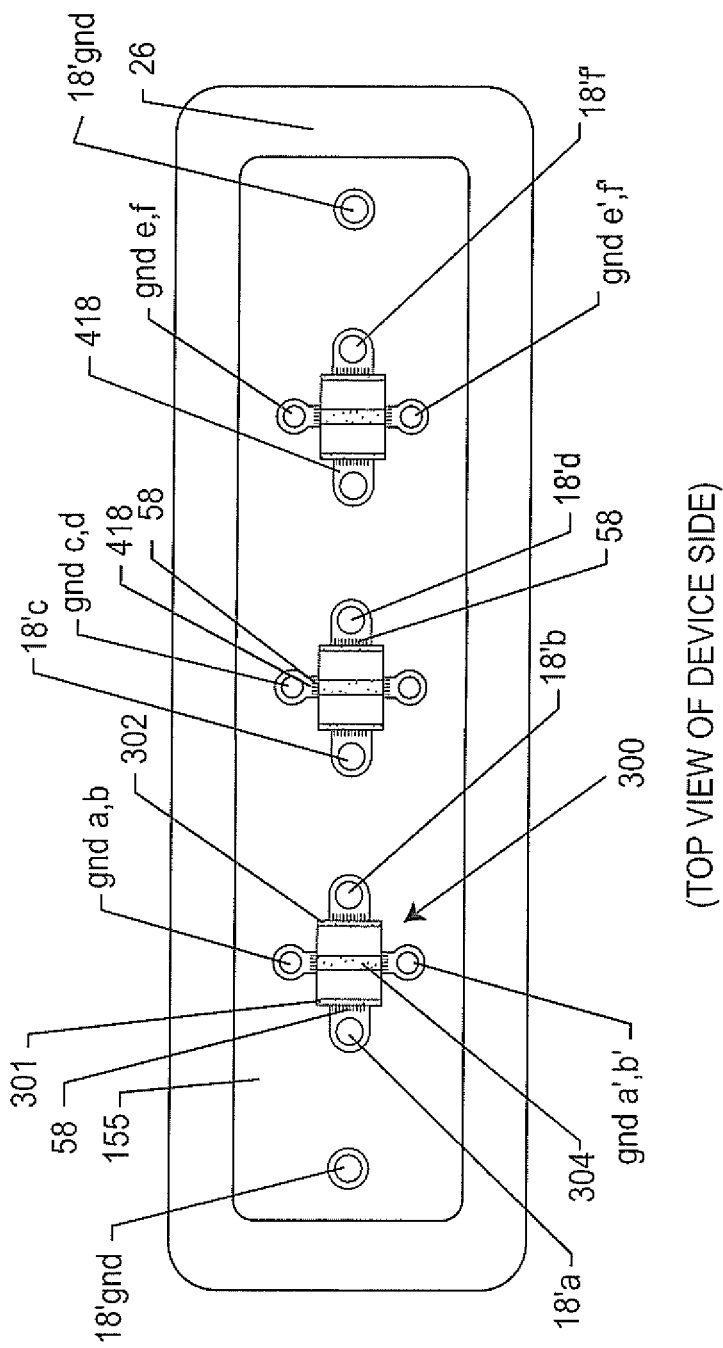
FIG. 24A is similar to FIG. 22 except that illustrated are X2Y attenuators populating the EMI filter circuit board instead of MLCCs.
Figure 24B:
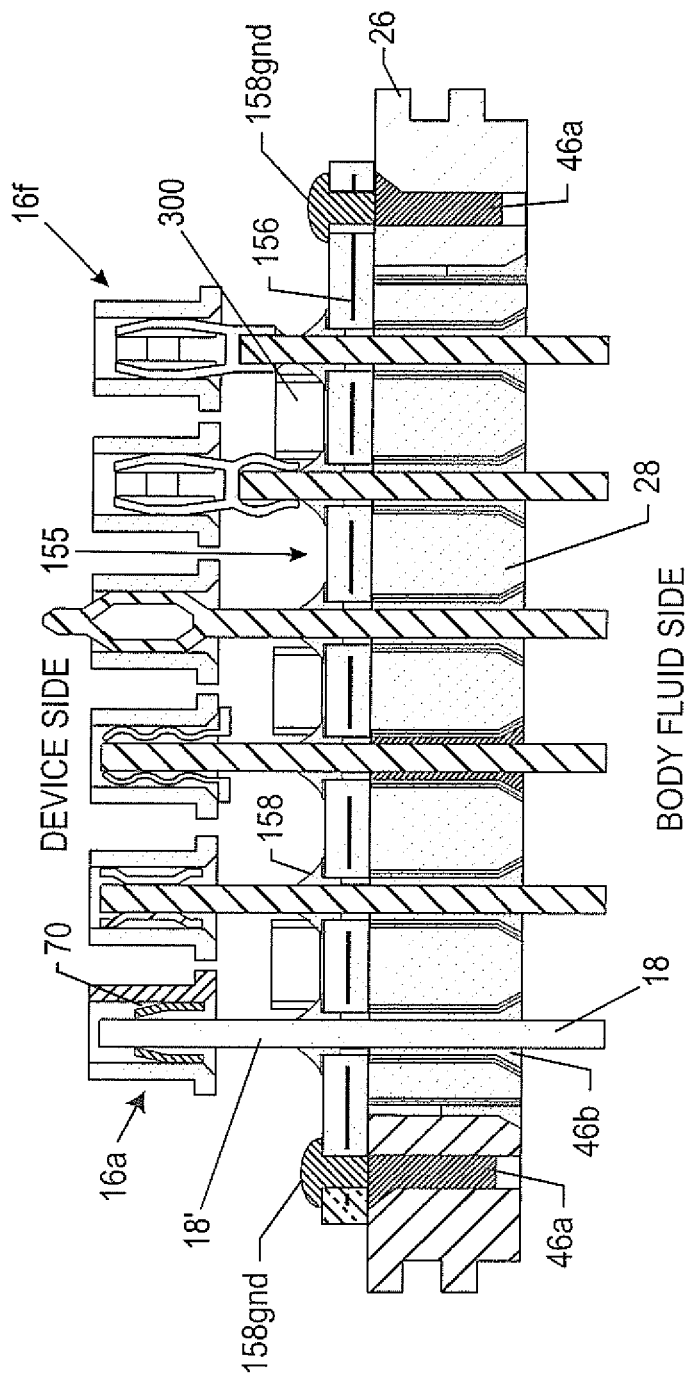
FIG. 24B is a sectional view taken from section 24B-24B from FIG. 24A.
Figure 24C:
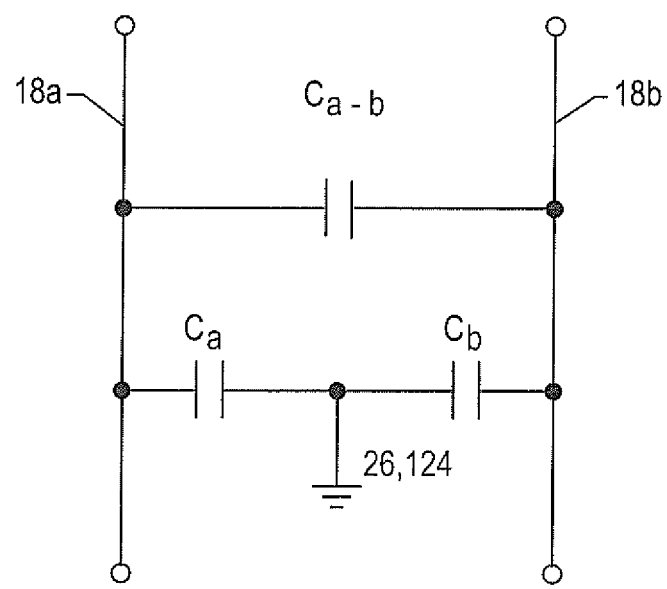
FIG. 24C is an electrical schematic for the configuration of FIG. 24B.
Figure 25A:
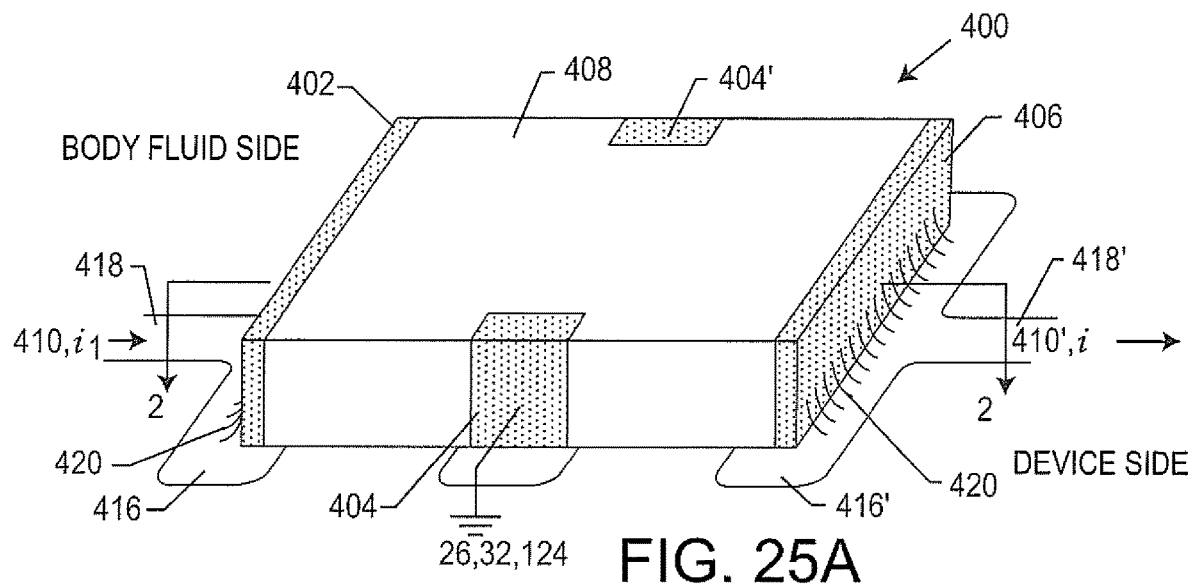
FIG. 25A is a perspective view of a prior art surface mounted capacitor known as a flat-thru capacitor.
Figure 25B:
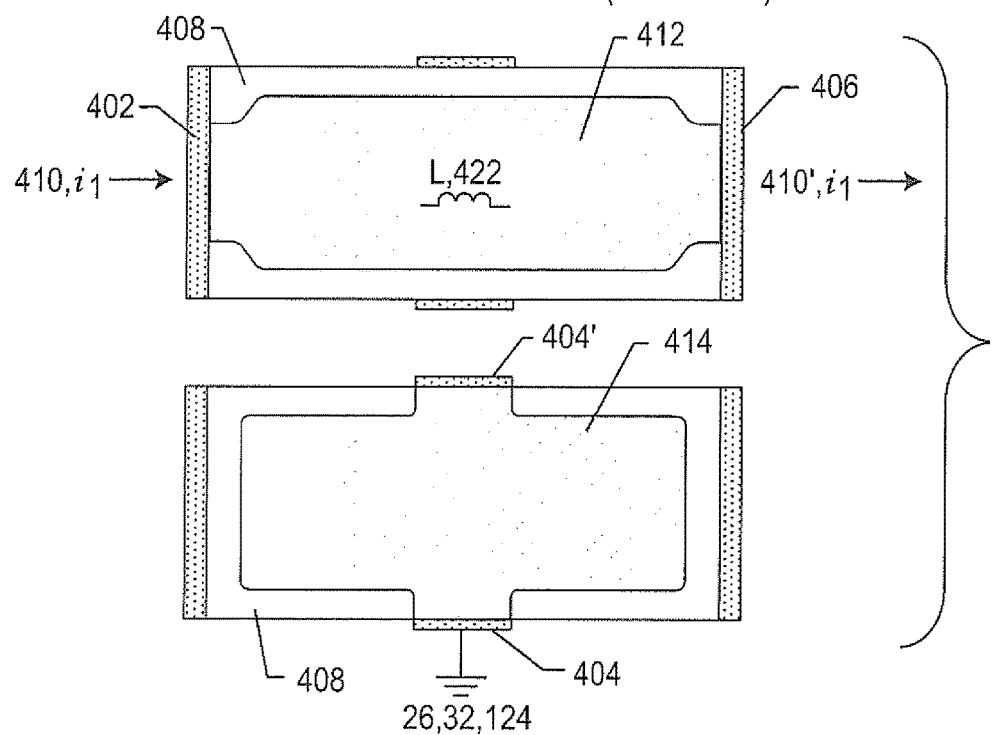
FIG. 25B is a sectional view taken along lines 25B-25B of FIG. 25A showing the active and ground electrode plates of the flat-thru capacitor.
Figure 26:
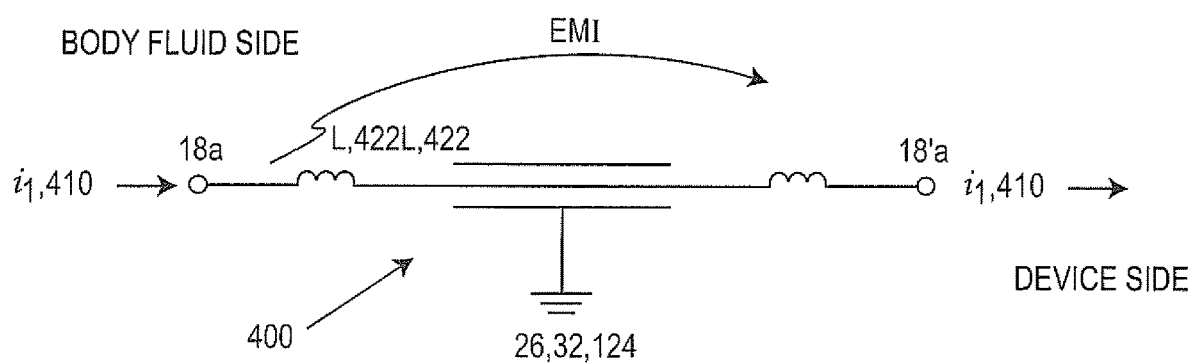
FIG. 26 is an electrical schematic for the configurations of FIGS. 25A and 25B.
Figure 27:
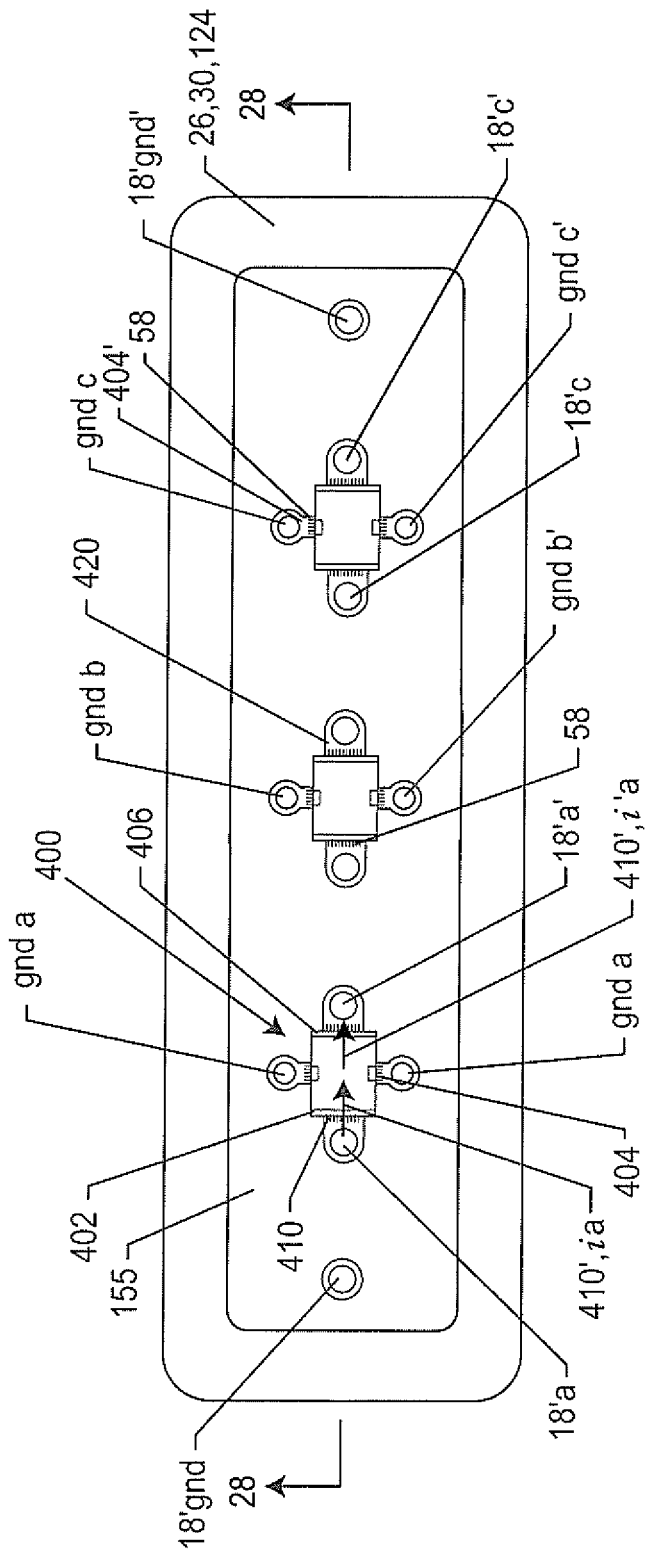
FIG. 27 is similar to FIG. 24A except that illustrated are flat-thru capacitors populating the EMI filter circuit board instead of X2Y attenuators.
Figure 28:
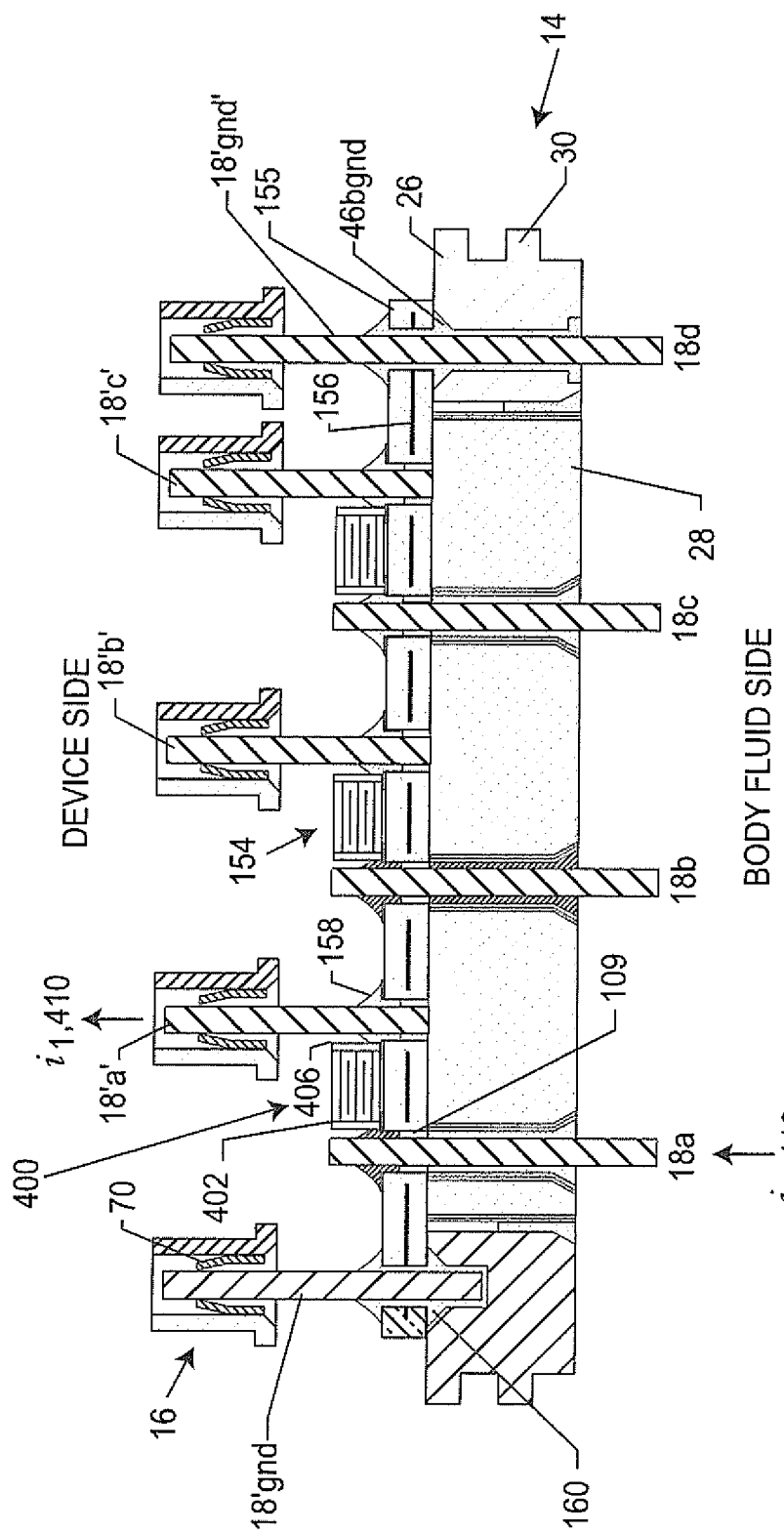
FIG. 28 shows a cross-sectional view of an alternative embodiment of a feedthrough connector assembly taken along lines 28-28 from FIG. 27. Illustrated are terminal pin connectors attached to terminal pins. It is noted that the terminal pins are attached to an AIMD active electronic circuit board (not shown) of the device side of an AIMD.
Figure 29:
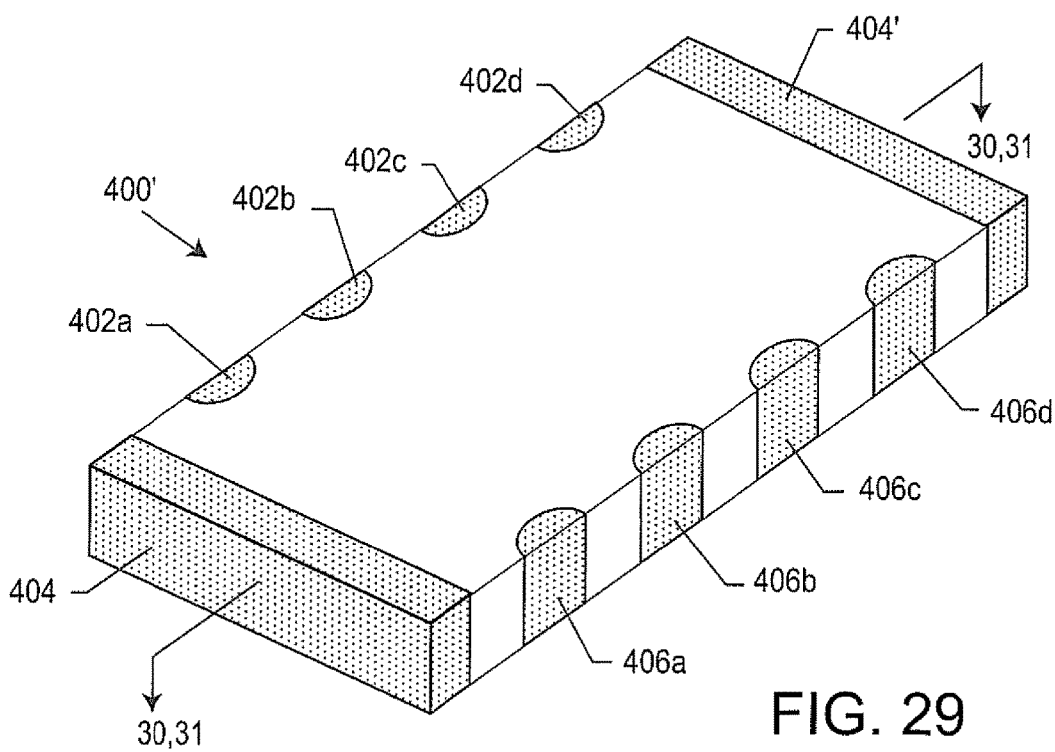
FIG. 29 is a perspective view of a quad polar flat-thru capacitor.
Figure 30:
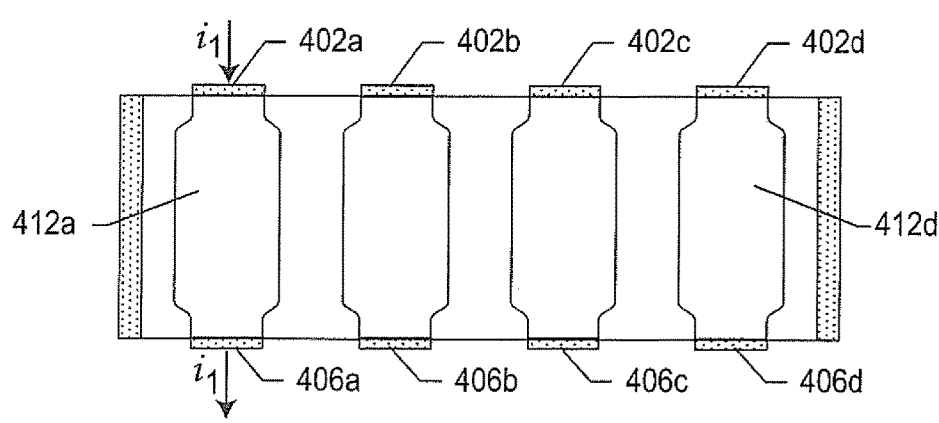
FIGS. 30 and 31 are sectional views taken along lines 30-30 and 31-31 of FIG. 29 showing the active and ground electrode plates of the quad polar flat-thru capacitor.
Figure 31:
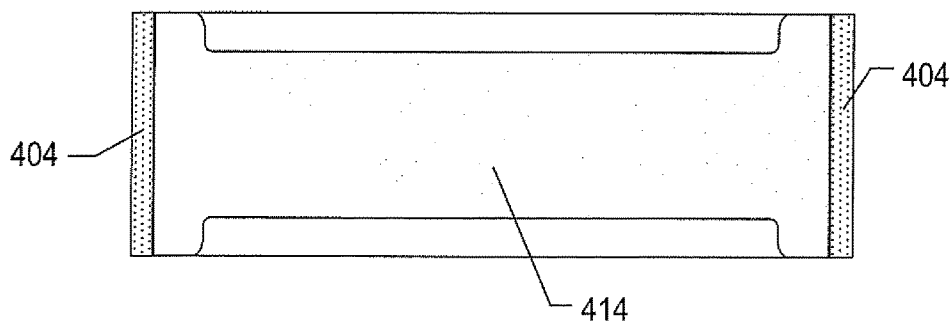

The nanoparticle-filled polymeric insulating material 379 illustrated by the ICD of FIG. 32A is not intended to be limiting to only ICDs, as any AIMD 12 illustrated in FIG. 1 may comprise terminal pin connectors 16, 16$gnd$ covered by the nanoparticle-filled polymeric insulating material 379 of the present invention. It is noted that the cutaway view of the AIMD 12 of FIG. 32A reveals a battery 130 and a main AIMD electronic circuit board 106, which characteristically has various electronic circuits, including battery charging circuits, high-energy storage capacitor charging circuits, biological sensing circuits, and high-voltage therapy delivery defibrillation circuits, among others. For simplicity, only one AIMD circuit board 106 is illustrated, however, it is understood that an AIMD may have a multiplicity of rigid and/or flexible (flex) circuit boards. Today's ICDs generally have several thousand programmable functions, so typically one or microprocessors can be included on the AIMD circuit board 106.

Figure 32B:
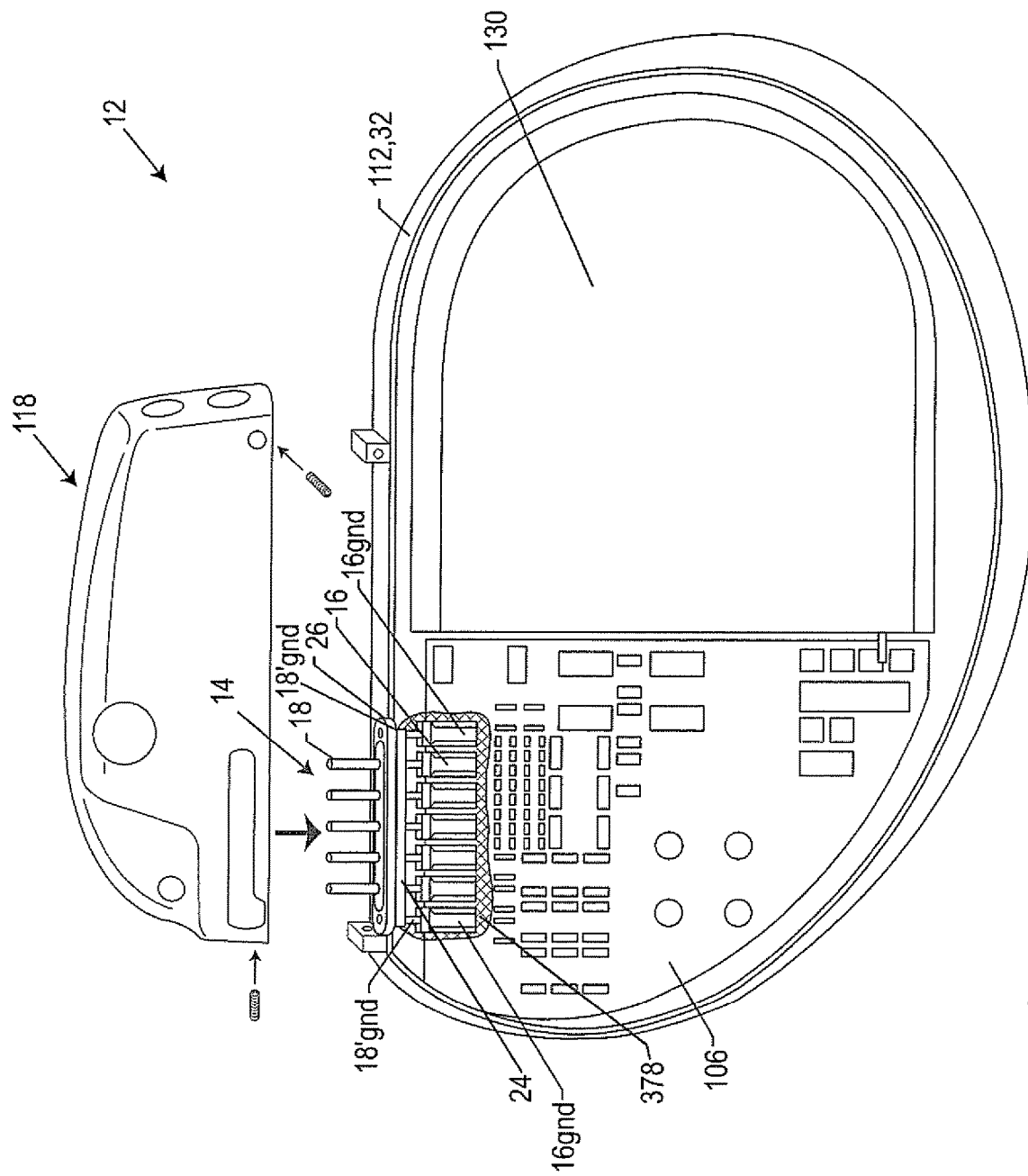
FIG. 32B is the same as FIG. 32A except that the novel insulating material is now a polymeric insulating material without an insulating nanoparticle fill.

FIG. 32B is very similar to FIG. 32A, except that the insulating material 378 is not filled with insulating nanoparticles. The polymeric insulating material 378 may be any of the conventionally applied insulating materials including an epoxy, a liquid silicone rubber, a polycarbonate, a polyester, a polyether, a polyurethane, a polyimide, or a polyamide.

Referring back to FIGS. 32A and 32B, the polymeric insulating materials 378, 379 without or with insulating nanoparticles, respectively, may be cured at room temperature, at elevated temperature, by radiation curing or by radiation heating. Suitable forms of radiation curing and heating include using an electron beam, gamma rays, x-rays, ultraviolet, or infrared exposure, near infrared (NIR) additives-based heating, thermal additives-based heating, laser, microwave, convection, conduction, or induction heating, hot gas, flame, oven or hot shoe heating, ultrasonic or resistance heating, or magnetic additives heating.

Figure 33:
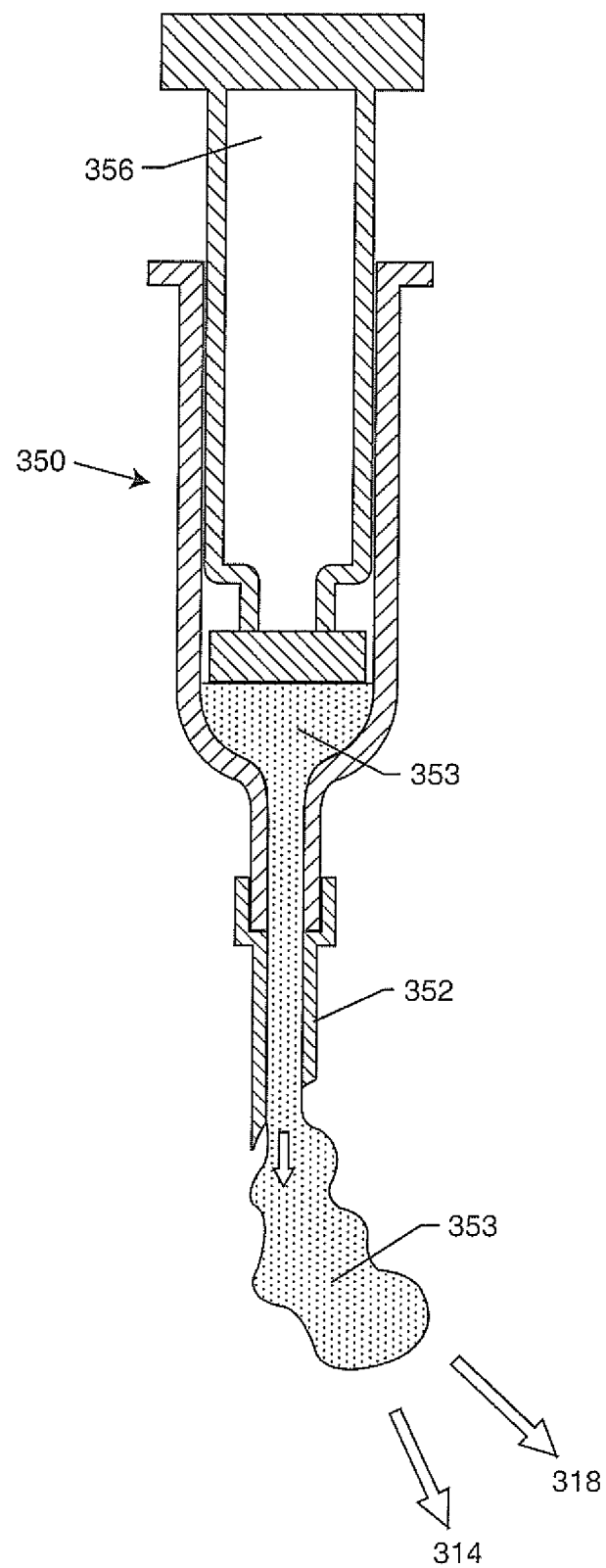
FIG. 33 is a table that provides insulating material types of the present invention, which includes symbols having a tear drop shape that serve as location markers for where to apply or not apply a particular insulating material.

FIG. 33 illustrates a syringe 350 with a plunger 356 that contains an uncured nanoparticle-filled polymeric insulating material 353. The uncured nanoparticle-filled polymeric insulating material may be an elastomer, a polymer, or a plastic, including an epoxy, a liquid silicone rubber, a polycarbonate, a polyester, a polyether, a polyurethane, a polyimide, or a polyamide. The plunger 356 of FIG. 33 is depressed so that the uncured nanoparticle-filled polymeric insulating material 353 is dispensed through a needle or nozzle 352 attached to a syringe end (which in FIG. 33 is a smaller diameter extension of the syringe). It is understood that any suitable syringe configuration or similarly operating dispensing apparatus may be used to dispense the uncured nanoparticle-filled polymeric insulating material 353. The syringe 350 or an automated dispensing system (not shown) may be used to dispense the uncured nanoparticle-filled polymeric insulating material 353 through the header block slot 316 of FIG. 32. The syringe 350 may also be used to dispense the uncured nanoparticle-filled polymeric insulating material 353 about the terminal pin connector 16 or 16$gnd$, which when cured becomes the nanoparticle-filled polymeric insulating material 379 covering terminal pin connectors.

FIG. 34 is a table categorizing the high-voltage insulating materials of the present invention and their respective location markers. The location markers are used in the following figures to indicate where the insulating materials should and should not be applied. Referring to Table 34, the first location marker 360 has no pattern fill, which indicates the physical locations where a polymeric insulating material is not required or would be undesirable. The next table category relates to nanoparticle-filled polymeric insulating materials. Element 353 represents an uncured (flowable) nanoparticle-filled polymeric insulating material and element 359 is associated with a dot filled location marker indicating the location for placing an uncured flowable nanoparticle-filled polymeric insulating material 353. Element 379 represents a cured nanoparticle-filled insulating material. The last table category relates to polymeric insulating materials that do not have a nanoparticle fill. Element 354 represents an uncured polymeric insulating material without a nanoparticle fill. Element 358 is associated with a double cross-hatch filled location marker indicating the location for placement of an uncured (flowable) polymeric insulating material without a nanoparticle fill 354. Element 378 represents a cured (solid or semi-rigid) polymeric insulating material without a nanoparticle fill.

Figure 35:
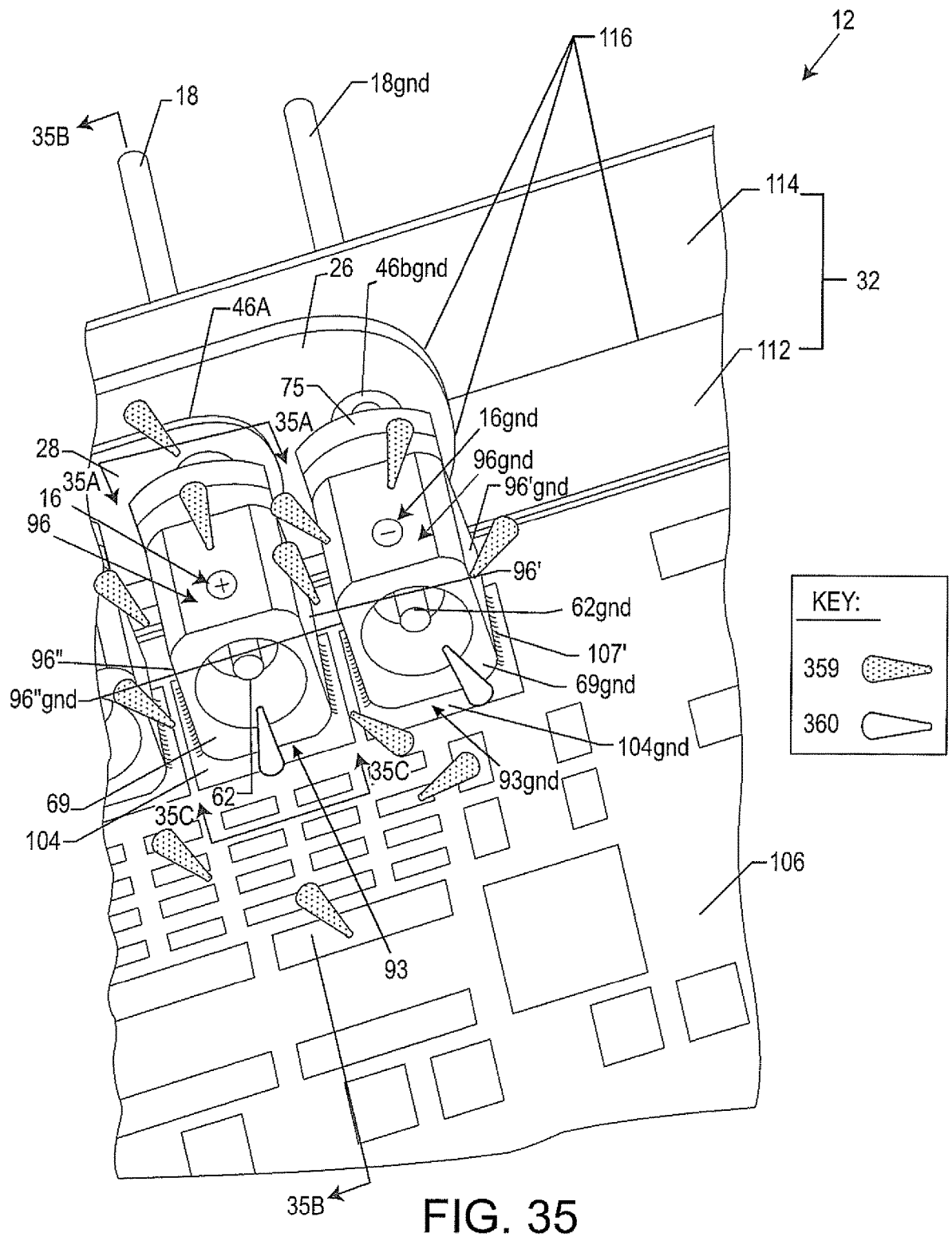
FIG. 35 is a blown-up partial view taken from 35-35 of FIG. 32A, illustrating the locations for necessary placement of insulating nanoparticle-filled polymeric insulating material and the locations where the insulating material is undesirable.
Figure 36:
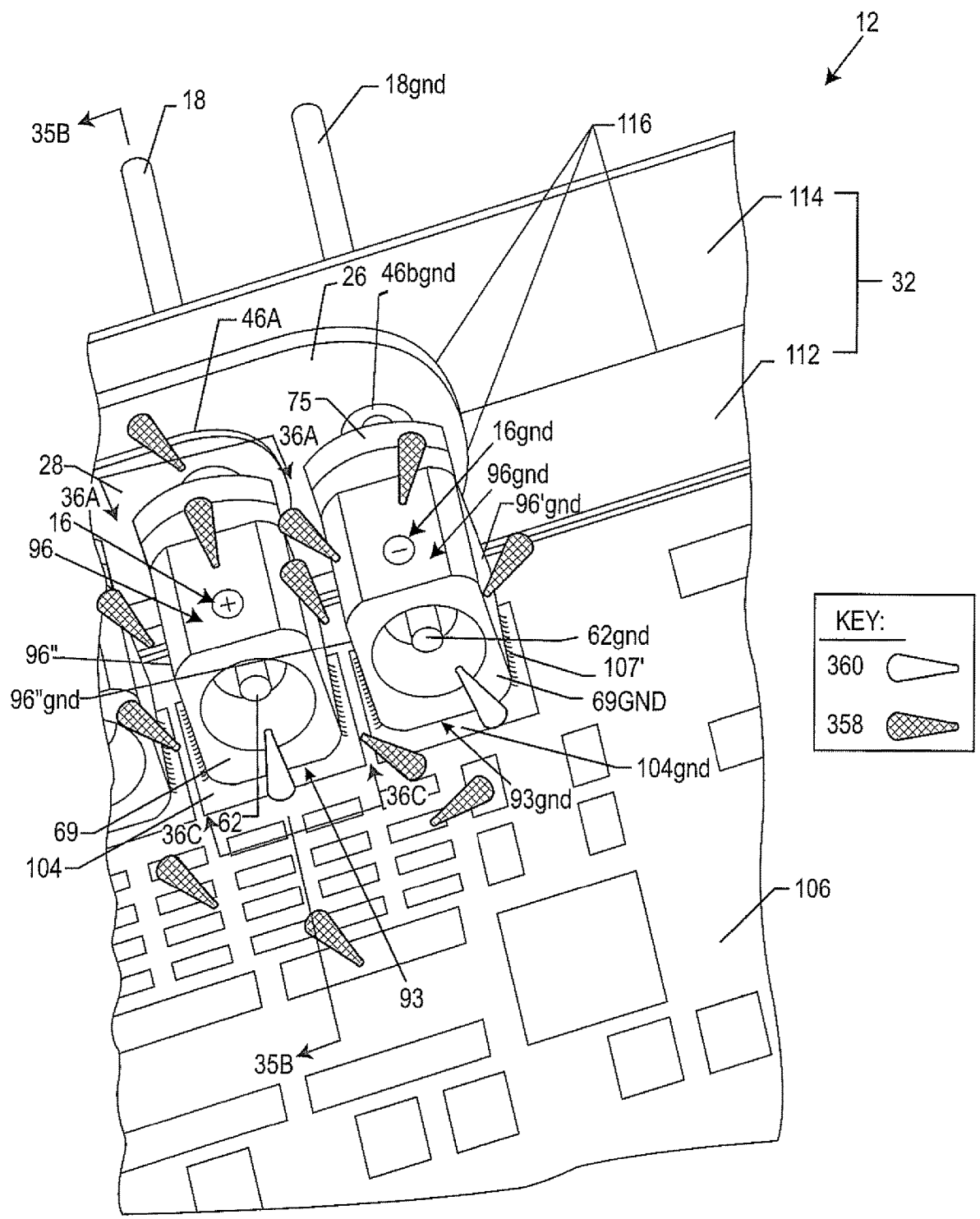
FIG. 36 is a pictorial cutaway view of an ICD similar to FIG. 35 having a connector cross-sectional view; the circuit board connectors are covered with a polymeric insulating material that is not filled with insulating nanoparticles.

FIG. 35 is a blown-up partial view taken along lines 35-35 of FIG. 32 illustrating terminal pin connectors 16 and 16$gnd$. Electrical connection material 107' is first disposed between the terminal pin connector housing 16 at surfaces 96"$gnd$ and 96'$gnd$. Typically, this electrical connection material 107' makes a filet between the vertical surface 96'$gnd$ and the circuit board mounting land or trace 104$gnd$. It is preferable to first form this electrical connection 107' prior to dispensing material 359. Location marker 359 indicates where it is highly desirable to apply the uncured nanoparticle-filled insulating polymer 353 of the present invention. These locations are areas of high electric field stress where electrical insulation between points of opposite polarity are very important. There are locations where the markers 360 indicate where a polymeric insulating material should not be placed. For example, in the case of removable terminal pin connectors, if any polymeric insulating material, with or without insulating nanoparticles, is accidentally dispensed or otherwise accumulates at the terminal pin distal ends 62 and 62$gnd$ within a connector housing 66 (not labelled) having an open end 69, then the terminal pins 18 or 18$gnd$ could be attached to the terminal pin connectors 96 or 96$gnd$, undesirably preventing removability.

Referring again to FIG. 35, to connect terminal pin connectors 16 to an AIMD 12, the distal end of the active terminal pin 62 of the feedthrough 14 (not labelled) is inserted into the active terminal pin connector 16 (+) and the distal end of the ground terminal pin 62$gnd$ is inserted into the ground terminal pin connector 16$gnd$ (−). The open distal housing ends 69 and 69$gnd$ (which may optionally be closed) of the terminal pin connectors 16 and 16$gnd$ expose their respective terminal pins 18' and 18'$gnd$ (not labelled), which has the advantage of facilitating visual inspection of the electrical connection of each active and ground feedthrough terminal pin 18, 18$gnd$ within their corresponding terminal pin connector 16, 16$gnd$. The distal housing end 69, 69$gnd$ may optionally be a closed end. Prior to coating the terminal pin connector, the partially uncoated or completely uncoated housing planar surface 93, 93$gnd$ (as shown in FIG. 35B) of each terminal pin connector 16, 16$gnd$ is electrically connected to a corresponding circuit board land 104 and 104$gnd$ using an electrical connection material 107'. The electrical connection material 107' may comprise a conductive adhesive, a conductive epoxy, a solder, a laser weld, or equivalent.

In an alternative embodiment, instead of having the electrical connection material 107' electrically connecting the uncoated housing planar surface 93 of the terminal pin connector 16 and 16gnd to a corresponding circuit board land 104 and 104gnd, a BGA dot, a solder dot, a conductive epoxy dot (not shown) may be used for electrical connection. It is understood that the circuit board lands 104 and 104gnd are electrically connected to electrical traces, circuits, circuitry and/or other electrical components within or on the AIMD circuit board 106. As previously disclosed by the table of FIG. 34, the dot-filled location markers 359 indicate where uncured nanoparticle-filled polymeric insulating material 353 is dispensed and later cured to form a solid nanoparticle-filled polymeric insulating material 379. In this embodiment, a nanoparticle-filled polymeric insulating material is used to increase the active-to-ground high-voltage standoff distance between the plus (+) and minus (−) signs. It is understood that the polymer may comprise an epoxy, a polyimide or even a vapor deposited insulation, such as a Parylene D. The polymer may also comprise any of the insulating materials for increasing dielectric breakdown strength that have been previously disclosed. The high-voltage standoff distance is important, even between adjacent positive terminals, because, as previously disclosed, the current flow of a biphasic pulse delivered by an ICD reverses, which means that the positive (+) and negative (−) polarities of the terminal pin connectors 16, 16gnd' will change in accordance with the direction of the delivered current. Noteworthy is that the polymeric insulating material of the present invention must be sufficiently disposed between the circuit board lands 104, including along the facing housing surfaces of each terminal pin connector 16 and 16gnd', as the active-to-ground standoff distance therebetween is relatively close. Without such polymeric insulating material, electrical breakdown risk may be undesirably high. The embodiment of FIG. 35 applies to both high-voltage (HV) and low-voltage (LV) devices, as both types of devices may be subjected to high-voltage, for example and as previously disclosed, inadvertent electrostatic discharge (ESD) or an automatic external defibrillator (AED) event, which, depending on AED paddle placement, can induce a high voltage across a patient's chest. FIG. 35 also provides location markers 360, which indicates locations where no polymeric insulating material is to be applied. It is especially important for terminal pin connectors having open distal housing ends 382, such as the terminal pin connectors 16, 16gnd of FIG. 35, that polymeric insulating material does not enter through the open distal housing end 69, 69gnd to the terminal pins 18 or 18'gnd, as each terminal pin is removably engaged by the prongs of a clip (not visible in this view). Should the polymeric insulating material enter through the open distal housing end 69, 69gnd to contact the removably engaged terminal pins 18 or 18'gnd, the prongs of the connector clip may become fixed to undesirably permanently secure the terminal pin 18 or 18gnd in place, which defeats the purpose of a removable terminal pin connector.

FIGS. 35A, 35B and 35C are similar to respective FIGS. 6A, 6B and 6C of previously incorporated by reference U.S. Pat. No. 11,211,741 and U.S. Pub. No. 2022/0115806, but they illustrate in more detail the present invention applied to a terminal connector 16. FIG. 35A is a pictorial view taken along line 35A-35A of FIG. 35. FIG. 35B is a sectional view taken along line 35B-35B of FIG. 35. FIG. 35C is a pictorial view taken along line 35C-35C of FIG. 35. It is understood that the present invention may apply to any of the embodiments disclosed in the incorporated by reference '741 patent.

FIGS. 35A, 35B and 35C each reveal the internal complexity of terminal pin connector 16. As previously disclosed, the polymeric insulating material preferably does not enter through the open distal housing end 69 of the terminal pin connector 16, for example, to the throughbore 74 of the clip 68 or in and about the prongs 70, which, after curing, would unremovably secure terminal pin 18' therewithin. As a result, rework and/or replacement of a defective ICD circuit board 106 would be precluded, which can be prohibitively costly. In a preferred embodiment, the uncured polymeric insulating material 353 or 354, with and without nanoparticle fill, respectively, is or is not dispensed as indicated by the location markers 358, 359, or 360 and then cured to form the solid polymeric insulating material 379 or 378. Accordingly, FIG. 35A illustrates a proximal end view of the terminal pin connector 16 having the cured nanoparticle-filled insulating polymeric material 379 on the surface of the proximal housing end 80, which corresponds to the left side of the terminal pin connector 16 of FIG. 35B. Location markers 360 show where there should not be any cured insulating polymeric material of any kind. FIG. 35C illustrates a distal end view of the terminal pin connector 16 having the cured nanoparticle-filled insulating polymeric material 379 on the surface of the distal housing end 69, which corresponds to the right side of the terminal pin connector 16 of FIG. 35B. The location marker 360 shows where there should not be any cured insulating polymeric material of any kind. FIG. 35B is a cross-sectional view of the terminal pin connector 16 illustrating the cured nanoparticle-filled insulating polymeric material 379 on all external connector surfaces except the external connector surface 93, which has no cured nanoparticle-filled insulating polymeric material 379 so that the terminal pin connector 16 can be mounted to a circuit board land 104 (not shown). Location markers 360 show where there should not be any cured insulating polymeric material of any kind. In summary, it is undesirable to have any polymeric insulating material in the areas indicated by location markers 360, as any polymeric insulating material in these areas can compromise the removability of a defective AIMD circuit board 106 from feedthrough active and/or ground terminal pins 18, 18'gnd. It is understood that either an open or closed distal housing end 69 may be used in the terminal pin connector 16 embodiments of the present invention. Closed distal housing ends 69 prevent the dispensed polymeric insulating material from entering into the body of a connector housing 66 of the terminal pin connectors 16 and 16gnd, thereby ensuring terminal pin connector removability.

FIGS. 36, 36A, 36B, 36C are the same as FIGS. 35, 35A, 35B, 35C, respectively, except now the polymeric insulating material 378 does not contain any nanoparticle fill.

Figure 37A:
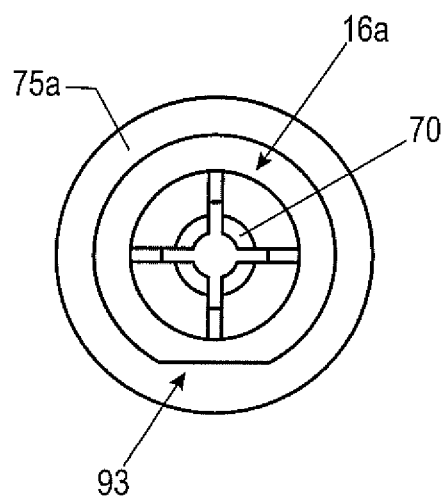
FIGS. 37A and 37B illustrate novel embodiments of terminal pin connectors that have a connector housing planar surface for mounting to a circuit board.
Figure 37C:
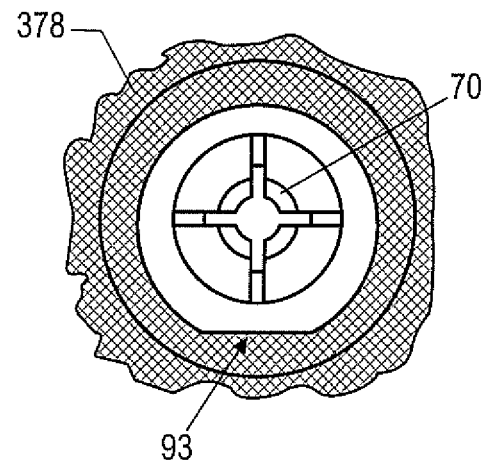
FIGS. 37C and 37D illustrate respectively embodiments of the terminal pin connectors of FIGS. 37A and 37B coated with insulating material.
Figure 37B:
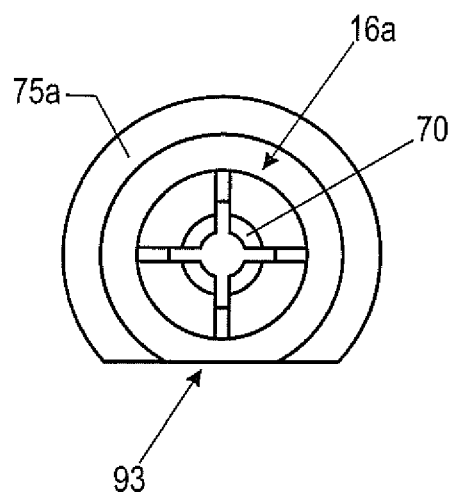

FIGS. 37A and 37B illustrate embodiments of terminal pin connectors 16a where at least a portion of the connector housing 66 (not labelled) has a planar surface 93 for mounting to an AIMD active electronic circuit board 106 (not shown). The connector housing of FIG. 37A illustrates a complete round flange 74a, while FIG. 37B shows the round flange 75a and the connector housing having planar surfaces 93.

Figure 37D:
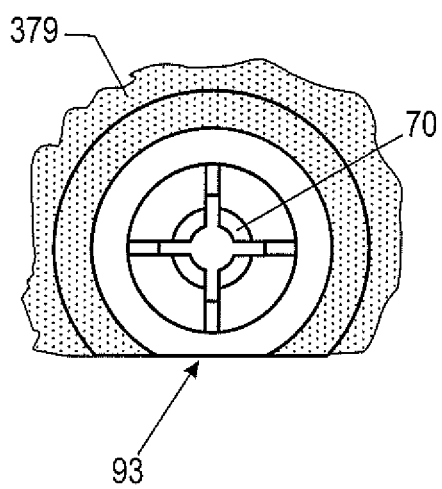

FIGS. 37C and 37D illustrate the embodiments of FIGS. 37A and 37B, respectively, coated with a polymeric insulating material. The embodiment of FIG. 37C is coated with a polymeric insulating material without insulating nanoparticle fill 378. The embodiment of FIG. 37D is coated with a nanoparticle-filled polymeric insulating material 379.

Figure 38A:
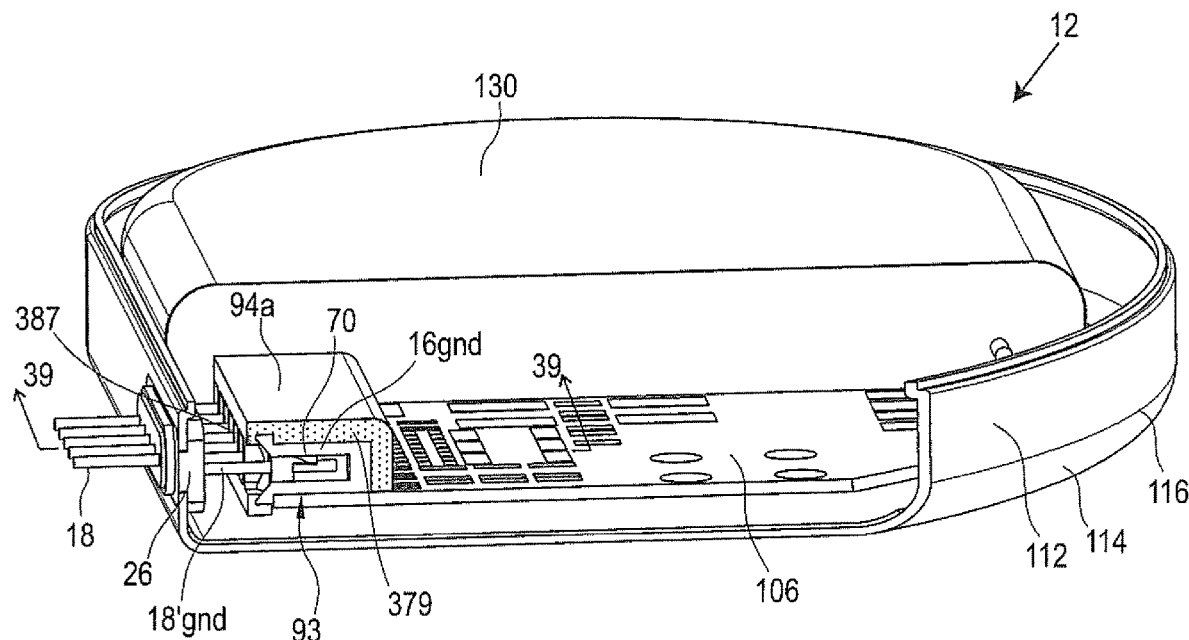
FIG. 38A is a pictorial view of a novel pre-molded high-voltage connector molded insulating block into which the circuit board connectors of FIG. 35 are inserted.

FIG. 38A illustrates the present invention applied to a prior art ICD 12I. The cutaway view of FIG. 38A reveals the ICD battery 130, the ICD circuit board 106, and a cross-section of one of two ICD ground terminal pin connectors 16gnd including the connector molded insulating block 94a. The molded insulating block is made with a nanoparticle-filled polymeric insulating material 379. The adjacent active terminal pins 18 plug into corresponding active terminal pin connectors 16 in a very similar manner, except that they pass through the ferrule 26 in an insulative relationship. The cross-sectional view of the ground terminal pin connector 16gnd shows that the ground terminal pin 18'gnd is electrically connected to the prong 70 of the ground terminal pin connector 16gnd. The nanoparticle-filled connector molded insulating block 94a, 379 has individual connector molded insulating block openings 393, in which each terminal pin connector 16 and 16gnd is embedded.

Figure 38B:
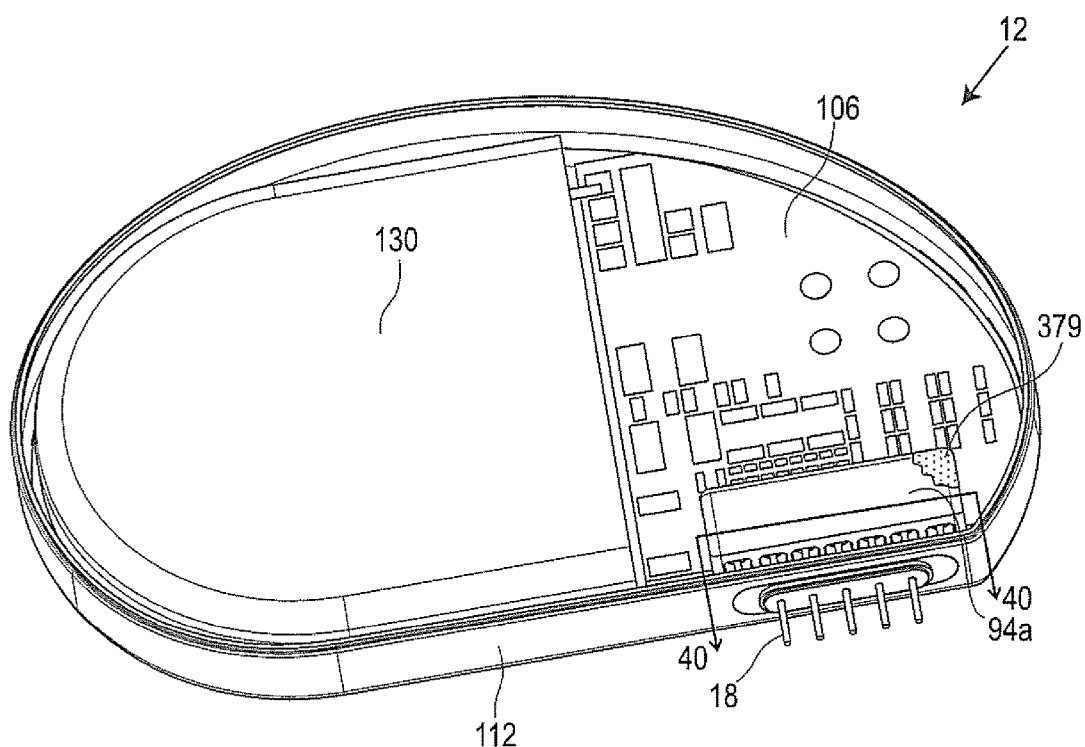
FIG. 38B is a pictorial view of FIG. 38A rotated to show that the connector molded insulating block has openings to expose the connector attachment surface for subsequent electrical connection to AIMD circuit board landing pads.

FIG. 38B is an isometric cutaway view similar to FIG. 38A, however, the drawing is rotated to show a top view of the terminal pin connector 16 with the molded nanoparticle-filled insulating connector block 94a, 379 electrically attached to the AIMD circuit board 106.

Figure 39:
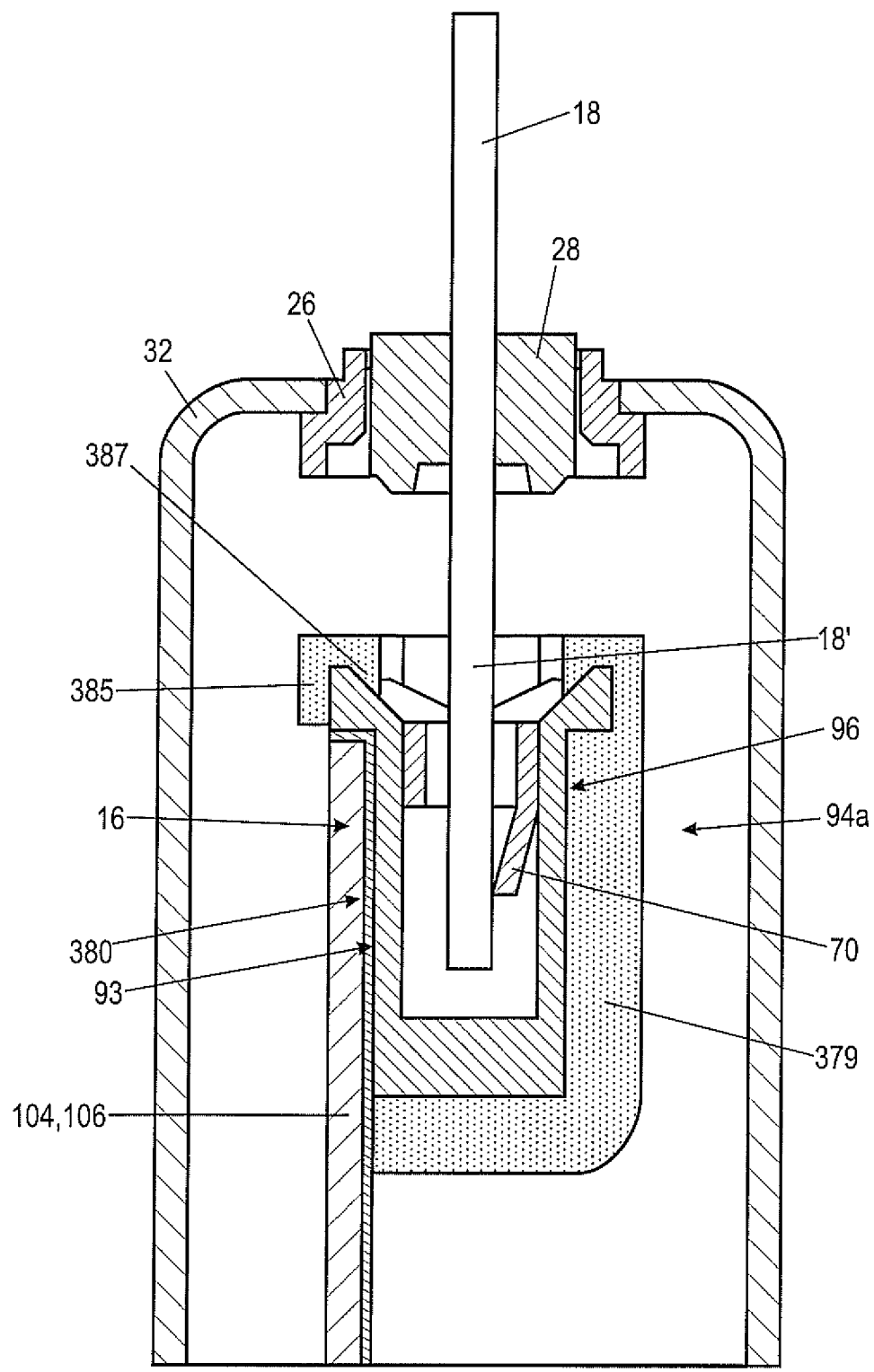
FIG. 39 is a cross-sectional end view of the connector molded insulating block covering a terminal pin connector electrically connected to a terminal pin.

FIG. 39 is a cross-sectional end view of the nanoparticle-filled 379 molded insulating connector block 94a within which an active terminal pin connector 16 is visible. The active terminal pin connector 16 is electrically connected to an active terminal pin 18'. A flowable or dispensable insulating material 380, such as a thermal-setting nonconductive epoxy or a thermal-setting insulative polyimide, is shown. This insulating material 380 is first dispensed before seating the molded insulating connector block 94a so that there are no air gaps between the terminal pin connector and the land (not shown) of the active electronic circuit board 106. It is very important that no air gaps are present between adjacent active and ground terminal pin connectors. Accordingly, it is understood that the insulating material 380 is also placed on surfaces adjacent the connector pins 16 before the molded insulating connector block 94a is seated. Ideally, the molded insulating block connector 94a is inserted or embedded into the layer of insulating material 380. In an embodiment, the insulative material 380 may comprise a nanoparticle-filled polymeric insulating material 379 (not shown).

Figure 40:
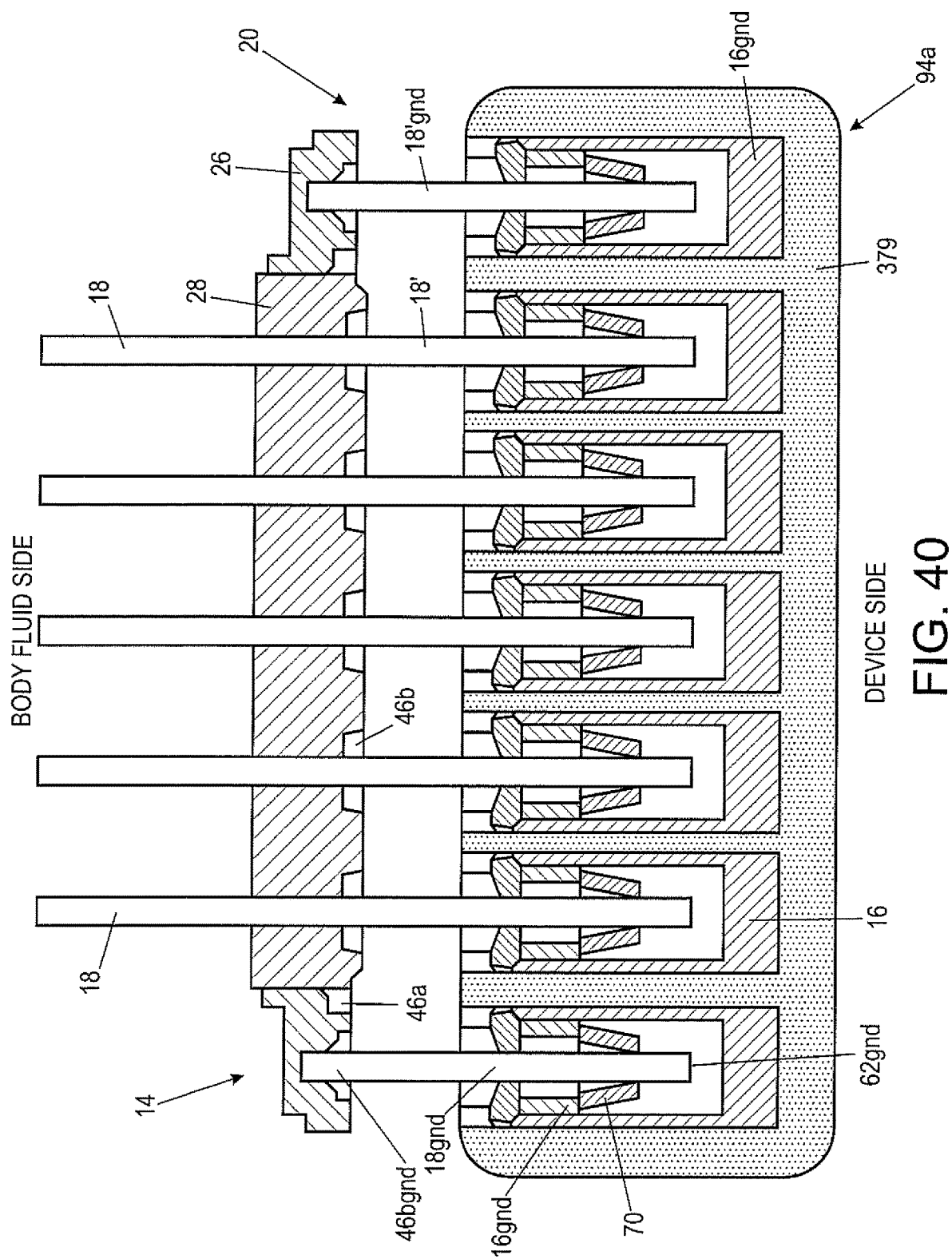
FIG. 40 is a cross-sectional view taken along lines 40-40 of FIG. 38B showing the novel connector molded insulating block covering the terminal pin connectors electrically connected to a terminal pins of a feedthrough.

FIG. 40 is a cross sectional view taken along section line 40-40 of FIG. 38B showing the connector molded insulating block 94a covering the terminal pin connectors 16, 16gnd of FIG. 39. The individual molded nanoparticle-filled insulating connector block openings 393 are more clearly understood by examining FIG. 40. Depending on the terminal pin connector design, the molded insulating connector block 94a can be over-molded with a nanoparticle-filled polymeric insulating material 379 embedding the terminal pin connectors 16 therein or pre-molded and then subsequently inserted onto the terminal pin connectors 16. The individual terminal pin connectors 16 and 16gnd are each separated by the molded polymeric columns of the molded nanoparticle-filled insulating connector block 94a, 379. The molded nanoparticle-filled insulating connector block 94a, 379 is more clearly understood by examining FIGS. 41A and 41B.

Figure 41A:
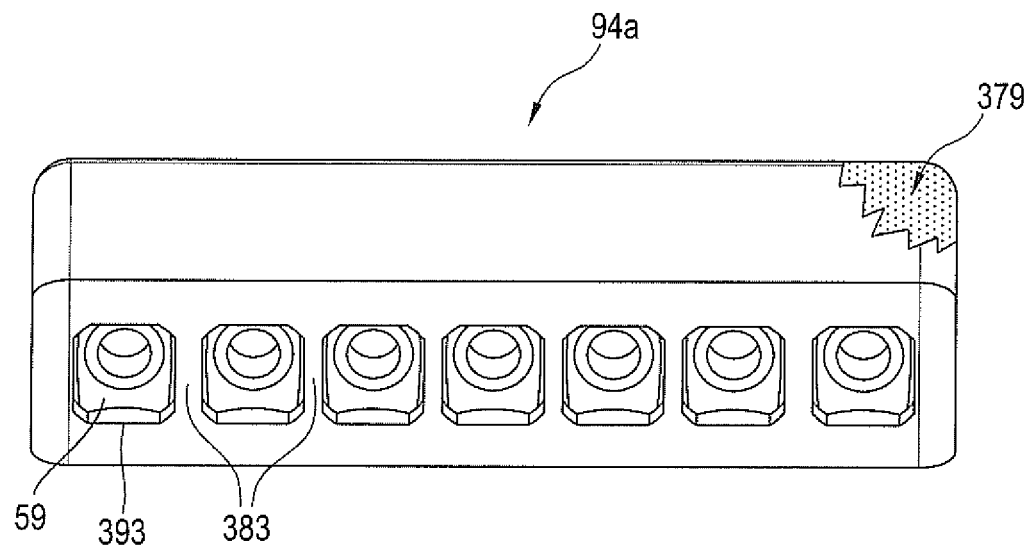
FIG. 41A is a pictorial view of a pre-molded high-voltage connector molded insulating block.
Figure 41B:
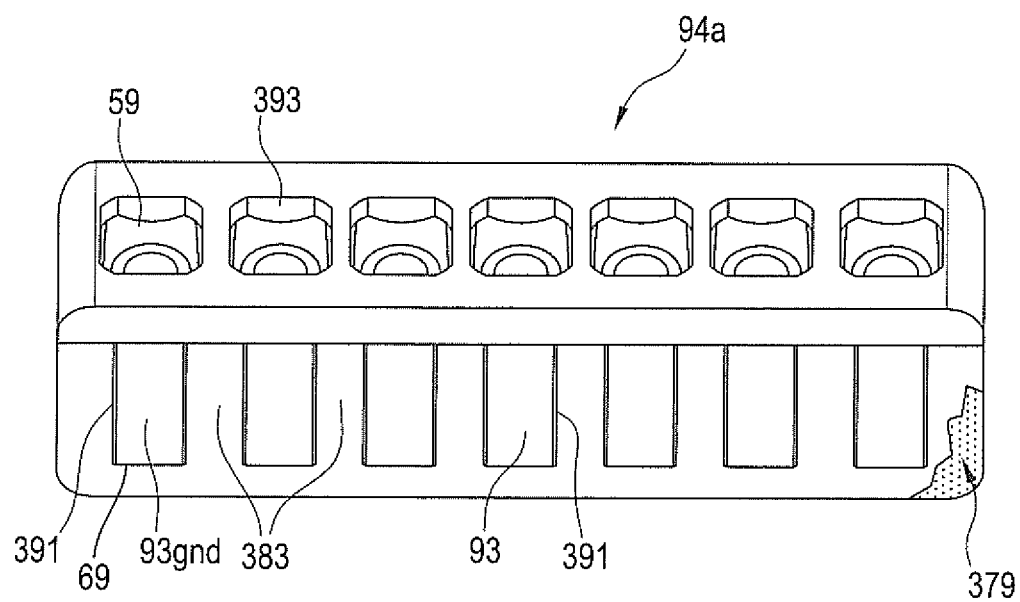
FIG. 41B is a pictorial view of the pre-molded high-voltage connector molded insulating block of FIG. 38 rotated to show that the connector molded insulating block has openings to expose a surface of a terminal pin connector for subsequent attachment to AIMD circuit board landing pads.

FIGS. 41A and 41B show that the molded insulating connector block 94a is a monolithic construct (i.e., a common housing) made of a nanoparticle-filled polymeric insulating material 379. Each terminal pin connector 16 is separated by a molded polymeric column 383, which insulates each terminal pin connector 16 one from another. The molded polymeric column 383 is formed monolithically with the molded nanoparticle-filled insulating connector block 94a, 379. Particularly visible in FIG. 41B is that the molded nanoparticle-filled insulating connector block 94a, 379 is configured with molded insulating connector block openings 393 for either inserting terminal pin connectors 16 therewithin, if pre-molded, or exposing the proximal connector housing ends 59 of the terminal pin connectors 16, if over-molded. The molded nanoparticle-filled insulating connector block 94a, 379 further embodies a molded insulating block L-shaped ledge 385, which is best shown by FIG. 39, for positioning against the edge of the AIMD circuit board 106. The molded L-shaped ledge 385 thus properly aligns the molded nanoparticle-filled insulating connector block 94a, 379 with the terminal pin connectors 16 and 16gnd therewithin over the circuit board lands 104, 104gnd (not shown). It is anticipated that the molded insulating block ledge 385 of the molded nanoparticle-filled insulating connector block 94a, 379 can be shaped into any particular ledge structure as required by the specific design of the terminal connectors 16.

Referring now to FIGS. 41A and 41B, perspective views of an unattached connector molded insulating block 94a with nanoparticle insulting fill 379 are illustrated. FIG. 41A shows that the molded insulating connector block 94a monolithically covers the terminal pin connectors 16, 16gnd. The proximal connector housing ends 59 of each terminal pin connector 16, 16gnd are visible through the molded insulating connector block openings 393. FIG. 41B is rotated to show that the planar surfaces 93, 93gnd of the terminal pin connectors 16, 16gnd within the molded insulating connector block 94a are exposed for mounting to circuit board lands 104 (not shown). The proximal connector housing ends 59 of each terminal pin connector 16, 16gnd are also visible through the molded insulating connector block openings 393. FIG. 41B also illustrates that the planar surfaces 93, 93gnd of the terminal pin connector 16, 16gnd is flush with the surface of the molded insulating connector block 94a, ready for mounting. Each terminal pin connector 16, 16gnd thereby resides within its own molded insulating block cavity 391 and is separated from an adjacent one by the molded polymeric insulating material 383 between each terminal pin connector 16, 16gnd.

Referring once again to FIGS. 41A and 41B, it is understood that the entire molded insulating connector block 94a comprises uniformly distributed insulating nanoparticle fill 379. The dots in the breakout sections 379 are representative of the insulating nanoparticle fill.

Referring back to FIG. 38A, it is noted that the illustrated insulating molded nanoparticle-filled insulating connector block 94a, 379 is an over-molded connector block. The L-shape of the molded insulating ledge 385 has a hook-like feature 387, which is best seen in FIG. 39, that captures and secures each terminal pin connector 16, 16gnd in place. Depending on the elasticity of the polymeric material used to form the molded insulating connector block 94a, 379, the hook-like feature 387 is optional. A higher elasticity nanoparticle-filled insulating material is able to stretch more so that, during insertion, the connector block openings 393 can stretch about the terminal pin connectors 16 until they are fully inserted. The hook-like feature 387 emerges about the proximal housing end 380 to clasp its cone-shaped countersink-like opening upon full insertion. Lower elasticity materials do not have as much relative stretchability, hence, molded insulating connector blocks 94a may not have the hook-like feature 387 of FIG. 37, but may optionally have a rounded or curved molded insulating connector block ledge 385 to facilitate terminal pin connector capture and locking. For both the over-molded and the pre-molded nano-particle filled insulating connector blocks 94a, 379, the connector housing 16gnd is electrically connected to their respective circuit board lands 104, 104gnd (not shown) using an electrical connection material 107'. The molded insulating connector block 94a comprises a polymeric material selected from any of the suitable electrically insulating materials previously disclosed.

Figure 42A:
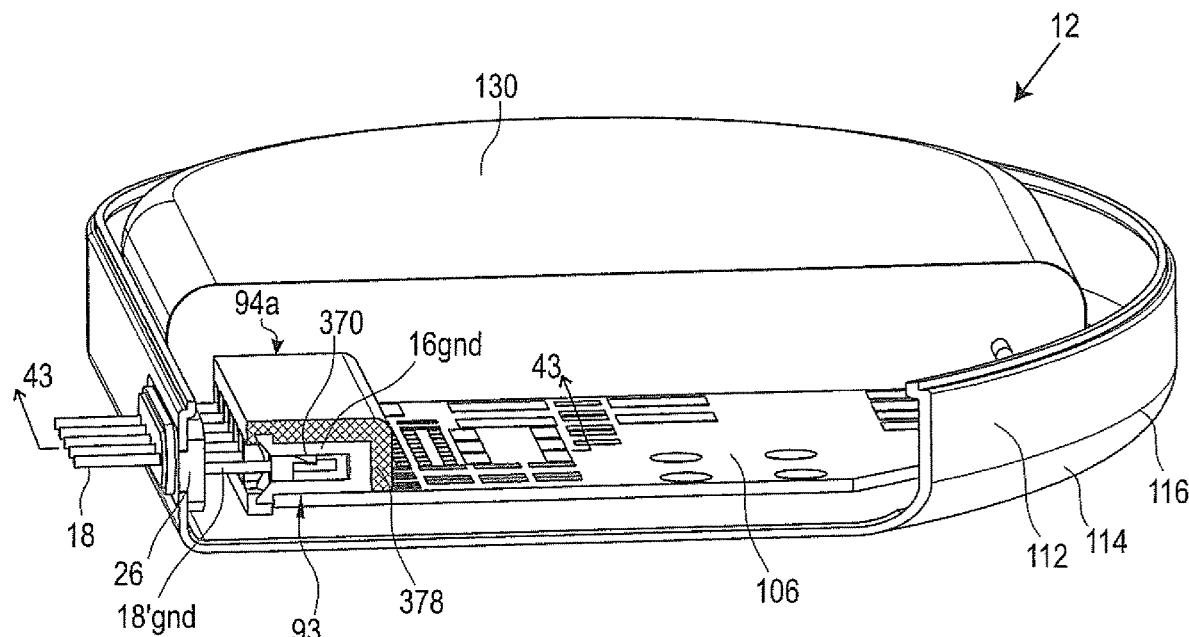
FIG. 42A is the same pictorial view of the pre-molded high-voltage connector molded insulating block of FIG. 38A FIG. 42B FIG. is the same rotated pictorial view of FIG. 38B, except now the connector molded insulating block is not filled with insulating nanoparticles.
Figure 42B:
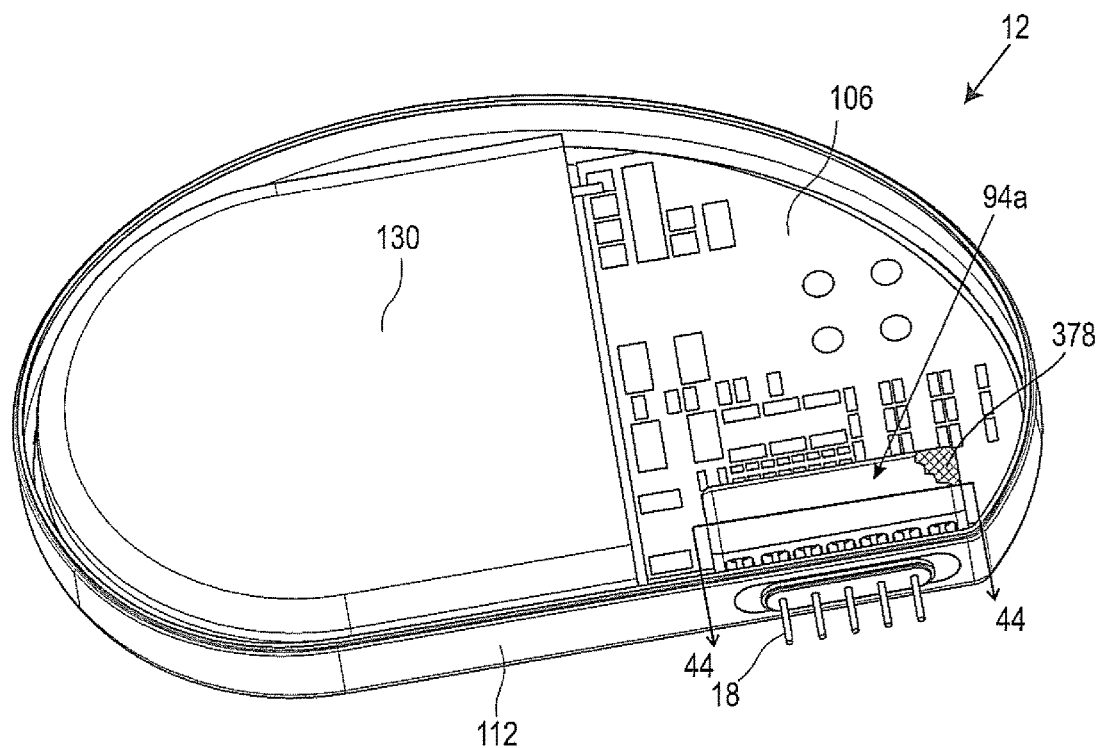

FIGS. 42A and 42B are similar to FIGS. 38A and 38B, respectively, except that the molded insulating connector block 94a is made of a polymeric material 378 that does not have an insulating nanoparticle fill.

Figure 43:
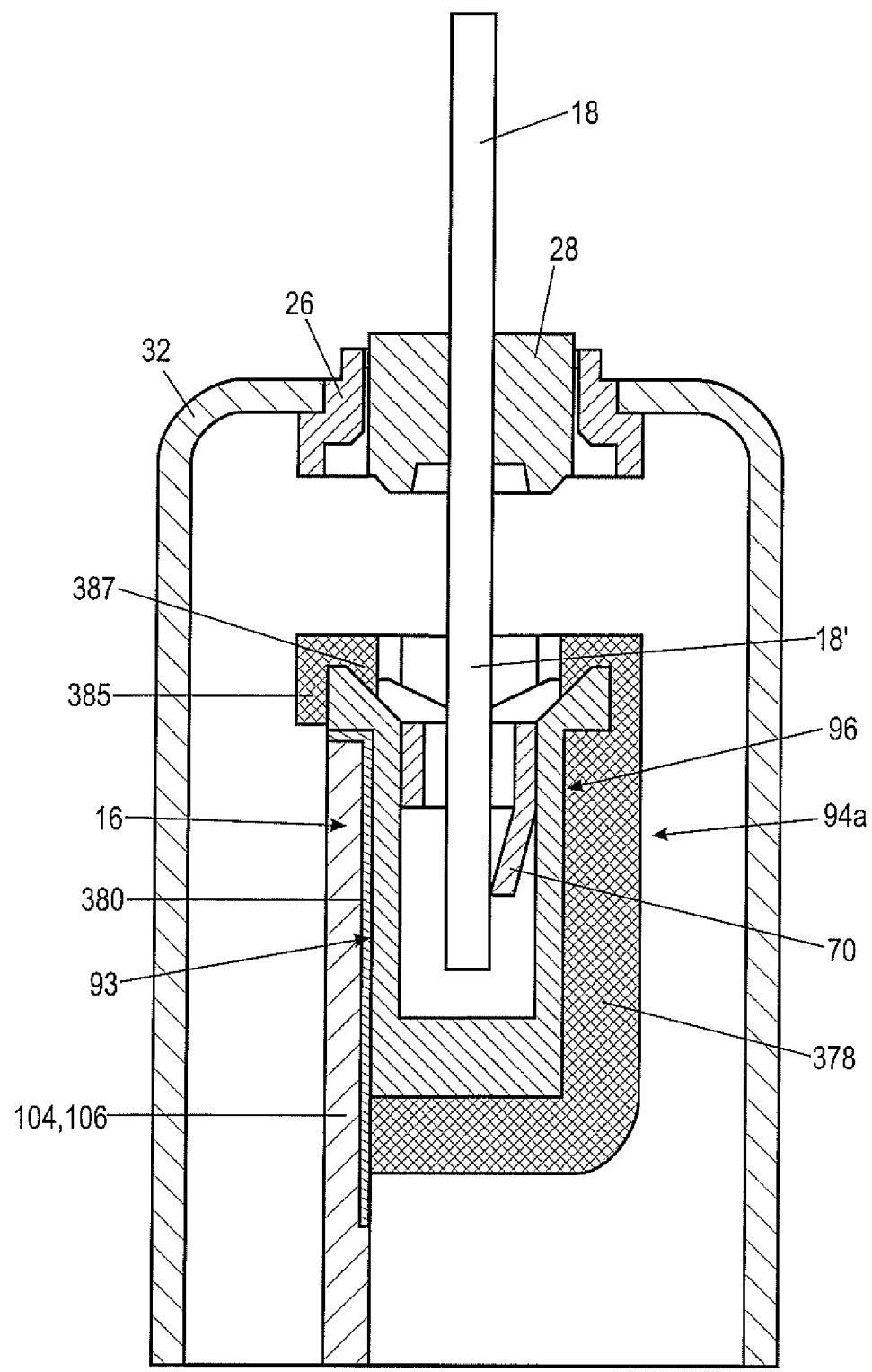
FIG. 43 is the same cross-sectional end view of FIG. 39, except now the connector molded insulating block is not filled with insulating nanoparticles.
Figure 44:
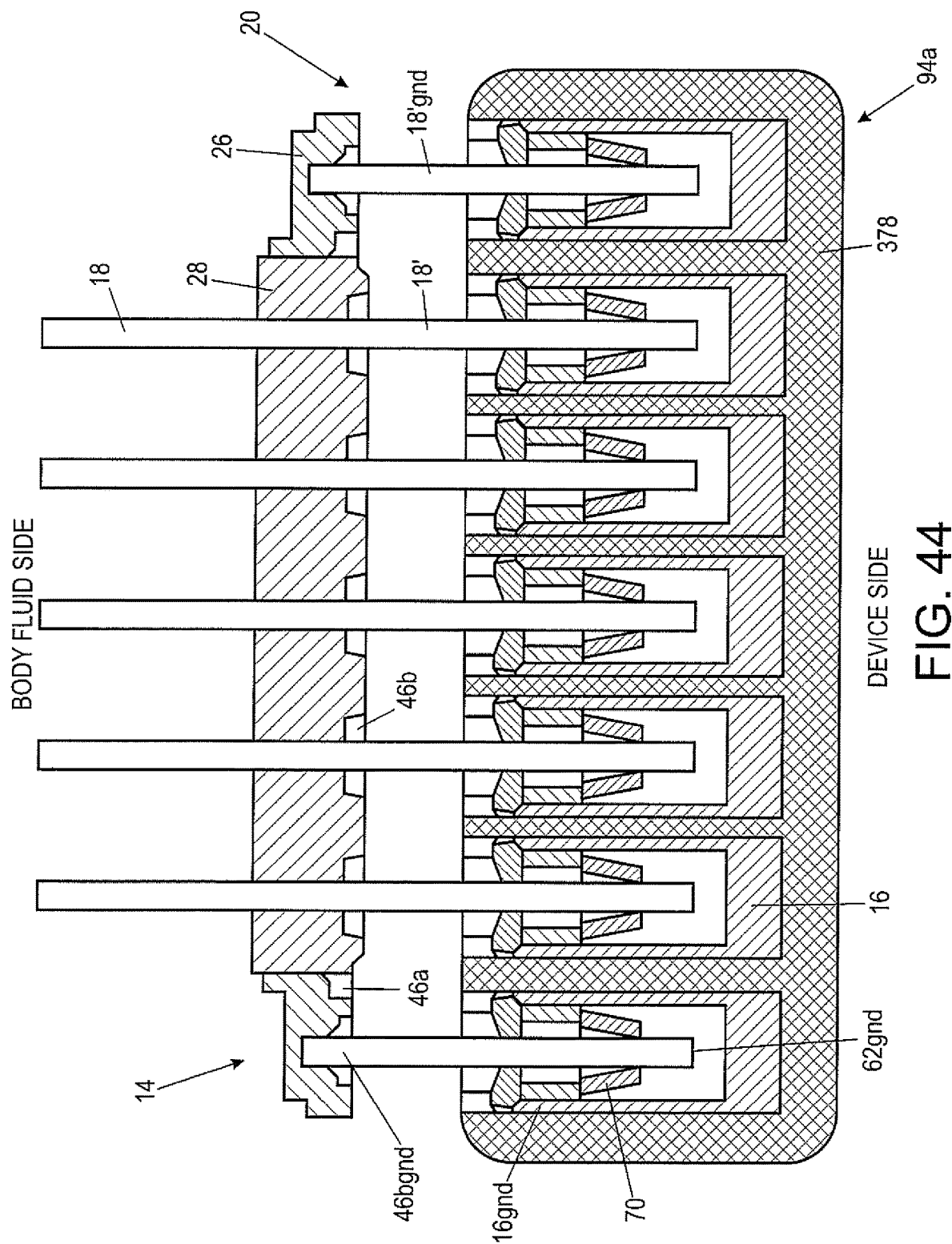
FIG. 44 is taken along lines 44-44 of FIG. 42B, which is the same cross-sectional view of FIG. 40, except that now the connector molded insulating block is not filled with insulating nanoparticles.

FIGS. 43 and 44 are similar to FIGS. 39 and 40, respectively, except that the molded insulating connector block 94a is made of a polymeric material 378 that does not have an insulating nanoparticle fill.

Figure 45A:
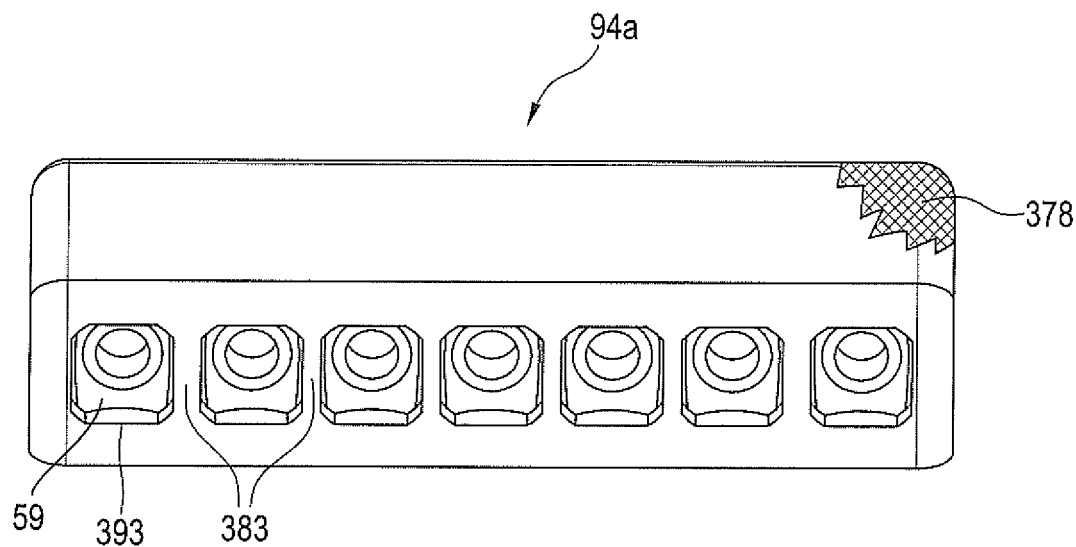
FIGS. 45A and 45B are the same pictorial views of FIGS. 41A and 41B, except now the connector molded insulating blocks are not filled with insulating nanoparticles.
Figure 45B:
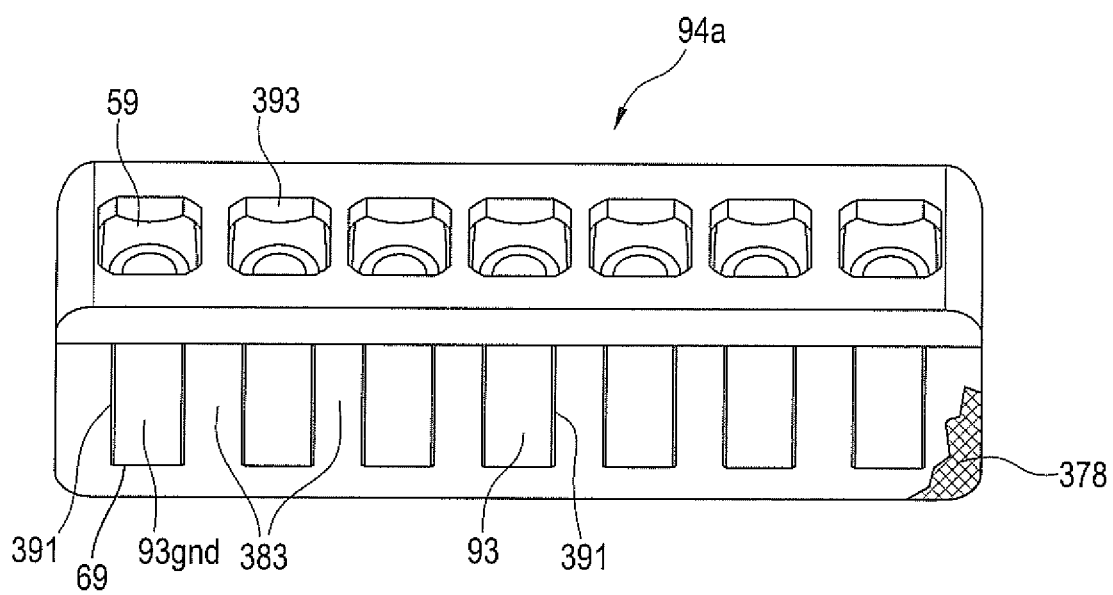

FIGS. 45A and 45B are similar to FIGS. 41A and 41B, respectively, except that the molded insulating connector block 94a is made of a polymeric material 378 that does not have an insulating nanoparticle fill.

Further regarding the insulating block 94a of the present invention (in other words, the common insulating connector housing), in addition to polymers with or without insulating nanoparticles, suitable moldable insulating materials include, for example, a moldable polymer, plastic, ceramic, glass-ceramic, or composite materials. Moldable polymeric insulating materials for making the molded insulating connector block 94a of the present invention comprise polymer-based materials, copolymers, thermosetting plastics, thermoplastics, epoxies, or elastomers. The filler insulating nanoparticles may be configured as particulates, short fibers, long fibers, spheres, flakes, submicron fibers, which are isotropically dispersed within the moldable insulating materials.

Suitable moldable electrically insulative polymeric, plastic, or composite materials for making the molded insulating connector block 94a include acrylics, phenolics, polyimides, and fluoropolymers. For example, the electrically insulative material may be selected from the group consisting of silicone, polyurethane, polyester, polyethylene, polypropylene, polyimide, polyamide, synthetic polyamide, acrylic, polyacrylates, perfluoroalkoxy (PFA), fluorinated ethylene-propylene (FEP), polyetheretherketone (PEEK), polyamide imide (PAI), polyphenylsulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), and combinations thereof. The molded insulating connector block 94a may be molded by one of injection molding, compression molding or thermoforming. Depending on the solid block design, rotational, blow molding and extrusion molding may also be used. It is appreciated that the molded insulating connector block 94a may alternatively be made by a 3D printing process such as stereolithography, digital light processing, two-photon polymerization processes, or other commercially available polymerization reaction processes. Additionally, any of the suitable moldable electrically insulating ceramics, glass-ceramic or composite materials disclosed below can be used in combination with the above named moldable electrically insulative polymeric, plastic, or composite materials for making the molded insulating connector block 94a.

Suitable moldable ceramics, glass-ceramic or composite materials for making the molded insulating connector block 94a may also be made of an insulating ceramic material instead of an insulating polymeric material. Suitable ceramic materials include alumina, baria, calcia, ceria, magnesia, silica, strontia, titania, and zirconia ceramic families. Non-limiting examples of some nano-scale metal oxides that can be used include: $Al_2O_3$, $BaO$, $CaO$, $CeO_2$, $MgO$, $ZrO_2$, $SiO_2$, $TiO_2$, $Al_2SiO_{53}$, $BaTiO_3$, $SrTiO_3$, and combinations thereof. Various stabilized or partially stabilized zirconia may be used including zirconia toughened alumina (ZTA) and alumina toughened zirconia (ATZ), yttrium stabilized zirconia (YSZ), yttrium-toughened zirconia (YTZP), and combinations thereof. Additionally, some nitrides may also be used, such as, AlN, $Si_3N_4$, BN, and combinations thereof. Additionally, the moldable electrically insulating ceramics, glass-ceramic or composite materials disclosed above may be used in combination with any of the suitable moldable electrically insulative polymeric, plastic, or composite materials disclosed in the previous paragraph for making the molded insulating connector block 94a. The insulating ceramic material may be a green (pre-sintered) ceramic that is machined or similarly formed by other applicable techniques to make the ceramic connector block 94a. The ceramic connector block 94a can also be formed by a molding process, for example, injection molding or compression molding, among others, or by a 3D-printing process, such as, selective laser sintering, selective laser melting, laminated object manufacturing, fused deposition modeling, among others.

While particular aspects of the present inventive subject matter have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the scope of the subject matter described herein. Furthermore, while this specification contains many specifics, these should not be construed as limitations on the scope of what may be claimed, but rather as descriptions of particular embodiments of the subject matter. Certain features that are described in this specification in the context of separate embodiments can also be implemented in combination in a single embodiment. Conversely, various features that are described in the context of a single embodiment can also be implemented in multiple embodiments, separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A circuit board connector assembly, comprising:
    a) a circuit board comprising at least a first electrical circuit;
    b) a first terminal pin connector, comprising:
        i) a first connector housing comprising an electrically conductive first sidewall having a first connector housing sidewall interior surface spaced from an exterior surface, the first connector housing sidewall interior surface defining a first housing opening extending along a first longitudinal axis, wherein the first connector housing exterior surface has at least one first planar exterior surface that is electrically connected to the first electrical circuit of the circuit board; and
        ii) an electrically conductive first compliant structure supported by the first connector housing sidewall interior surface; and
    c) an insulative material coating at least a portion of the first connector housing sidewall exterior surface, wherein the insulative material does not coat the at least one first planar exterior surface that is electrically connected to the at least one electrical circuit of the circuit board.

2. The circuit board connector assembly of claim 1, wherein the insulative material is selected from silicone, polyurethane, polyester, polyethylene, polypropylene, polyimide, polyamide, synthetic polyamide, acrylic, polyacrylates, perfluoroalkoxy (PFA), fluorinated ethylene-propylene (FEP), polyetheretherketone (PEEK), polyamide imide (PAI), polyphenylsulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), and combinations thereof.

3. The circuit board connector assembly of claim 2, wherein the insulative material includes nanoparticles selected from $Al_2O_3$, BaO, CaO, $CeO_2$, MgO, $ZrO_2$, $SiO_2$, $TiO_2$, $Al_2SiO_5$, $BaTiO_3$, $SrTiO_2$, ZnO, $Si_3N_4$, zirconia toughened alumina (ZTA), alumina toughened zirconia (ATZ), Yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof.

4. The circuit board connector assembly of claim 1, wherein the insulative material is selected from an epoxy, a liquid silicone rubber, a polycarbonate, a polyester, a polyether, a polyurethane, a polyimide, or a polyamide, and wherein the insulative material include a nanoparticle material selected from $Al_2O_3$, aluminum nitride (AlN), boron nitride (BN), and mixtures thereof.

5. The circuit board connector assembly of claim 3, wherein the nanoparticles range in size from greater than about 100 nanometers (0.1 microns) to about 40,000 nanometers (40 microns).

6. The circuit board connector assembly of claim 3, wherein a nanoparticle loading in the polymeric insulating material ranges from >0% to about 40%, by weight.

7. The circuit board connector assembly of claim 1, wherein the electrically conductive first compliant structure supported by the first connector housing sidewall interior surface is selected from at least two prongs angled from the first connector housing interior surface toward the first longitudinal axis in the first housing opening, a first wavy tine, and a first spring clip.

8. The circuit board connector assembly of claim 1, wherein the first connector housing of the first terminal pin connector comprises a first clip base supported by the first connector housing sidewall interior surface in the first housing opening, and wherein the first clip base supports at least two first connector prongs as the first compliant structure, the at least two connector prongs being angled inwardly toward the first longitudinal axis of the first housing opening.

9. The circuit board connector assembly of claim 1, further comprising:
a) the circuit board comprising at least a second electrical circuit;
b) at least a second terminal pin connector, comprising:
i) a second connector housing comprising an electrically conductive second sidewall having a second connector housing sidewall interior surface spaced from an exterior surface, the second connector housing sidewall interior surface defining a second housing opening extending along a second longitudinal axis, wherein the second connector housing exterior surface has at least one second planar exterior surface that is electrically connected to the second electrical circuit of the circuit board; and
ii) an electrically conductive second compliant structure supported by the second connector housing sidewall interior surface, and
iii) wherein, with the first and second planar exterior surfaces of the first and second connector housings being electrically connected to the respective first and second electrical circuits, the first and second connector housings are in a side-by-side arrangement mounted on the circuit board with respective first and second exterior portions of the first and second exterior surfaces facing each other,
c) wherein the insulative material coats the first and second connector housing sidewall exterior surfaces including the facing first and second exterior portions, but does not coat the first and second planar exterior surfaces that are electrically connected to the first and second electrical circuits of the circuit board.

10. The circuit board connector assembly of claim 1, wherein a first alignment flange extends outwardly from the first planar exterior surface electrically connected to the at least one electrical circuit of the circuit board, and wherein the first alignment flange contacts an edge of the circuit board.

11. The circuit board connector assembly of claim 10, wherein the first alignment flange comprises a first inwardly tapering surface extending into the first housing opening defined by the first connector housing sidewall interior surface.

12. The circuit board connector assembly of claim 10, wherein the first alignment flange resides between two first planar exterior surfaces of the first connector housing exterior surface.

13. The circuit board connector assembly of claim 12, wherein the two first planar exterior surfaces are oriented normal to each other.

14. An active implantable medical device (AIMD), comprising:
a) an AIMD housing;
b) a circuit board contained inside the AIMD housing, the circuit board comprising at least one electrical circuit;
c) a terminal pin connector contained inside the AIMD housing, the terminal pin connector comprising:
i) a connector housing comprising an electrically conductive connector housing sidewall having a connector housing sidewall interior surface spaced from an exterior surface, wherein the connector housing sidewall interior surface defines a housing opening extending along a longitudinal axis, and wherein the connector housing exterior surface has at least one planar exterior surface that is electrically connected to the at least one electrical circuit of the circuit board;
ii) an electrically conductive compliant structure supported by the connector housing sidewall interior surface; and
iii) an insulative material coating at least a portion of the connector housing sidewall exterior surface, but not the at least one planar exterior surface that is electrically connected to the at least one electrical circuit of the circuit board;
d) a feedthrough, comprising:

i) an electrically conductive ferrule comprising a ferrule opening, wherein the ferrule is sealed in an opening in the AIMD housing;

ii) an insulator hermetically sealed to the ferrule in the ferrule opening, wherein the insulator has an insulator body fluid side opposite an insulator device side, the insulator body fluid and device sides residing outside and inside the AIMD housing, respectively;

iii) at least one insulator passageway extending through the insulator; and iv) an electrically conductive terminal pin hermetically sealed to the insulator in the insulator passageway, wherein the terminal pin extends outwardly beyond the insulator device side, e) wherein, with the terminal pin connector mounted on the circuit board adjacent to the insulator device side, the terminal pin connector is configured to allow multiple insertions and retractions of the feedthrough terminal pin into and out of the electrically conductive compliant structure supported by the connector housing sidewall interior surface being accordingly contacted to and uncontacted from the terminal pin of the feedthrough.

15. The AIMD of claim 14, wherein the insulative material is selected from an epoxy, a liquid silicone rubber, a polycarbonate, a polyester, a polyether, a polyurethane, a polyimide, and a polyamide, and mixtures thereof, and wherein the insulative material include a nanoparticle material selected from $Al_2O_3$, aluminum nitride (AN), boron nitride (BN), and mixtures thereof.

16. The AIMD of claim 15, wherein the nanoparticle material ranges in size from greater than about 100 nanometers (0.1 microns) to about 40,000 nanometers (40 microns).

17. The AIMD of claim 15, wherein the nanoparticle material has a loading in the polymeric insulating material that ranges from >0% to about 40%, by weight.

18. The AIMD of claim 14, wherein the connector housing of the terminal pin connector comprises a clip base supported by the connector housing sidewall interior surface in the connector housing opening, and wherein the clip base supports at least two connector prongs as the compliant structure, the at least two connector prongs being angled inwardly toward the longitudinal axis of the connector housing opening.

19. The AIMD of claim 14, wherein the electrically conductive compliant structure supported by the connector housing sidewall interior surface is selected from at least one prong angled from the connector housing interior surface toward the longitudinal axis in the housing opening, a wavy tine, and a spring clip.

20. The AIMD of claim 14, wherein an alignment flange extends outwardly from the at least one planar exterior surface that is electrically connected to the at least one electrical circuit of the circuit board, and wherein the alignment flange contacts an edge of the circuit board.

21. The AIMD of claim 20, wherein the alignment flange comprises an inwardly tapering surface extending into the connector housing opening defined by the connector housing sidewall interior surface.

22. The AIMD of claim 20, wherein the alignment flange resides between two exterior planar surfaces of the connector housing exterior surface.

23. The AIMD of claim 14, further including a feedthrough capacitor comprising at least one active electrode plate interleaved in a capacitive relationship in a capacitor dielectric with and at least one ground electrode plate, wherein the active electrode plate is electrically connected to the feedthrough terminal pin and the at least one ground electrode plate is electrically connected to the ferrule.

24. A circuit board connector assembly for an active implantable medical device (AIMD), the circuit board connector assembly comprising:

a) a circuit board comprising a circuit board land connected to at least one electrical circuit;

b) a terminal pin connector, comprising:

i) a connector housing comprising an electrically conductive sidewall having a connector housing sidewall interior surface spaced from an exterior surface, the connector housing interior surface defining a housing opening extending along a longitudinal axis, wherein the connector housing exterior surface has at least one planar exterior surface that is electrically connected to the at least one electrical circuit of the circuit board; and ii) at least one electrically conductive connector prong supported by the connector housing sidewall interior surface in the housing opening, wherein the connector prong is angled toward the longitudinal axis;

c) an electrical connection material connecting the at least one planar exterior surface of the connector housing exterior surface to the circuit board land; and d) an insulative material coating at least a portion of the connector housing sidewall exterior surface and the electrical connection material, wherein the insulative material does not coat the at least one planar exterior surface that is electrically connected to the at least one electrical circuit of the circuit board.

25. The circuit board connector assembly of claim 24, wherein the electrical connection material is selected from a braze, a conductive adhesive, a conductive epoxy, a solder, a laser weld, and combinations thereof.

26. The circuit board connector assembly of claim 24, wherein the insulative material is selected from an epoxy, a liquid silicone rubber, a polycarbonate, a polyester, a polyether, a polyurethane, a polyimide, and a polyamide, and mixtures thereof, and wherein the insulative material includes a nanoparticle material selected from $Al_2O_3$, aluminum nitride (AlN), boron nitride (BN), and mixtures thereof.

27. The circuit board connector assembly of claim 9, wherein the first and second connector housings are connected to first and second active electrical circuits of the circuit board, or the first connector housing is connected to an active electrical circuit and the second connector housing is connected to a ground electrical circuit of the circuit board.

28. The circuit board connector assembly of claim 9, wherein the first connector housing is connected to an active electrical circuit and the second connector housing is connected to a ground electrical circuit of the circuit board, and wherein the insulative material is configured to prevent flashover, avalanche discharge, carbon tracking, catastrophic failure, and microcoulomb discharge between the first and second connector housings.

* * * * *